(12) United States Patent
Ho et al.

(10) Patent No.: US 9,440,063 B2
(45) Date of Patent: Sep. 13, 2016

(54) METHODS FOR REDUCING DISCOMFORT DURING ELECTROSTIMULATION, AND COMPOSITIONS AND APPARATUS THEREFOR

(75) Inventors: Johnson Ho, Glen Cove, NY (US); Preet Minhas, Richmond Hill, NY (US); Marom Bikson, Brooklyn, NY (US); Abhishek Datta, New York, NY (US); Varun Bansal, Edison, NJ (US); Jinal Patel, Boston, MA (US); Dan Steingart, New York, NY (US); Jorge Vega, Jackson Heights, NY (US); Lucas Parra, New York, NY (US)

(73) Assignee: RESEARCH FOUNDATION OD THE CITY UNIVERSITY OF NEW YORK, New York, NY (US)

( * ) Notice: Subject to any disclaimer, the term of this patent is extended or adjusted under 35 U.S.C. 154(b) by 933 days.

(21) Appl. No.: 13/142,140

(22) PCT Filed: Dec. 30, 2009

(86) PCT No.: PCT/US2009/069843
§ 371 (c)(1),
(2), (4) Date: Sep. 14, 2011

(87) PCT Pub. No.: WO2010/078441
PCT Pub. Date: Jul. 8, 2010

(65) Prior Publication Data
US 2011/0319975 A1 Dec. 29, 2011

Related U.S. Application Data

(60) Provisional application No. 61/141,469, filed on Dec. 30, 2008.

(51) Int. Cl.
*A61N 1/04* (2006.01)
*A61N 1/36* (2006.01)

(52) U.S. Cl.
CPC .......... *A61N 1/0408* (2013.01); *A61N 1/0456* (2013.01); *A61N 1/0472* (2013.01); *A61N 1/0496* (2013.01); *A61N 1/36014* (2013.01)

(58) Field of Classification Search
CPC ............ A61N 1/0456; A61N 1/0472; A61N 1/36025; A61N 1/0484; A61N 1/048; A61N 2/006; A61N 2/02; A61H 2201/1604; A61H 2201/02; A61B 5/6801; A61B 5/416; A61B 5/6811; A61B 5/6812; A61B 5/0478; A61B 5/0408; A61B 5/0492; A61B 5/6814; A61B 5/04085; A61B 5/6803; A61B 2562/16; A61B 2562/14; A61B 2562/04; A61B 2562/164
USPC ......................................... 600/383; 607/139
See application file for complete search history.

(56) References Cited

U.S. PATENT DOCUMENTS

| | | |
|---|---|---|
| 4,537,198 A | 8/1985 | Corbett |
| 4,920,979 A | 5/1990 | Bullara |

(Continued)

FOREIGN PATENT DOCUMENTS

| | | | | |
|---|---|---|---|---|
| WO | WO2009061920 A1 * | 5/2009 | ........... | A61B 5/0478 |
| WO | WO2009128810 A1 * | 10/2009 | ............... | A61N 1/36 |

*Primary Examiner* — Christopher D Koharski
*Assistant Examiner* — Jeremiah Kimball
(74) *Attorney, Agent, or Firm* — Hoffman & Baron, LLP

(57) ABSTRACT

An electrode assembly for neuro-cranial stimulation includes an electrode, a conductive gel, and an adapter including an interior compartment for positioning the electrode relative to the adapter and for receiving and retaining the conductive gel. The conductive gel contacts the electrode along an electrode-gel interface. An orifice at one end of the interior compartment and adjacent to a positioning surface of the adapter for positioning the electrode assembly against a skin surface of a user enables the conductive gel is able to contact the skin surface of the user to define a gel-skin interface, such that a minimum distance between the electrode-gel interface and the gel-skin interface is maintained between 0.25 cm and 1.3 cm. An electrode assembly mounting apparatus is provided for adjustably positioning a plurality of electrode assemblies against target positions on the cranium.

43 Claims, 37 Drawing Sheets

(56) References Cited

U.S. PATENT DOCUMENTS

| | | |
|---|---|---|
| 5,344,440 A | 9/1994 | Stephen |
| 5,540,736 A * | 7/1996 | Haimovich et al. ............ 607/46 |
| 6,052,609 A | 4/2000 | Ripoche et al. |
| 6,276,054 B1 | 8/2001 | Cartmell et al. |
| 6,567,702 B1 * | 5/2003 | Nekhendzy et al. ........... 607/46 |
| 2002/0029005 A1 * | 3/2002 | Levendowski ...... A61B 5/0478 600/545 |
| 2004/0199042 A1 * | 10/2004 | Riehl et al. ...................... 600/9 |
| 2006/0094924 A1 * | 5/2006 | Riehl ................ 600/9 |
| 2006/0122454 A1 * | 6/2006 | Riehl et al. ...................... 600/9 |
| 2006/0259094 A1 * | 11/2006 | Naisberg et al. ............... 607/45 |
| 2007/0225585 A1 * | 9/2007 | Washbon et al. ............. 600/393 |
| 2010/0274152 A1 * | 10/2010 | McPeck et al. ............. 600/544 |
| 2011/0144716 A1 * | 6/2011 | Bikson et al. ................. 607/45 |

* cited by examiner

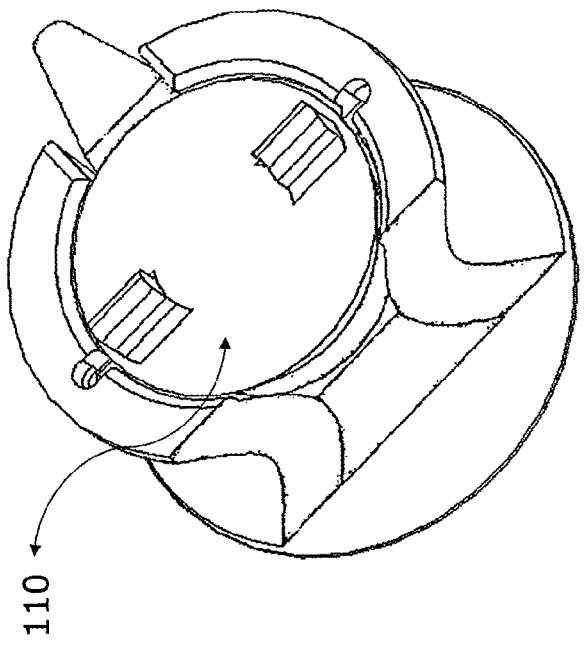
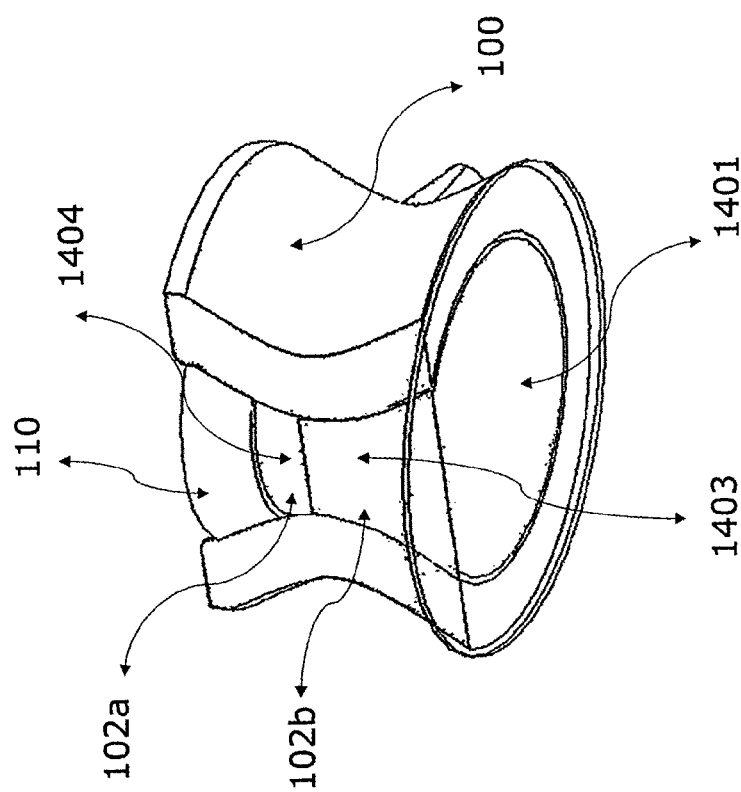
Fig. 14(a)
Fig. 14(b)

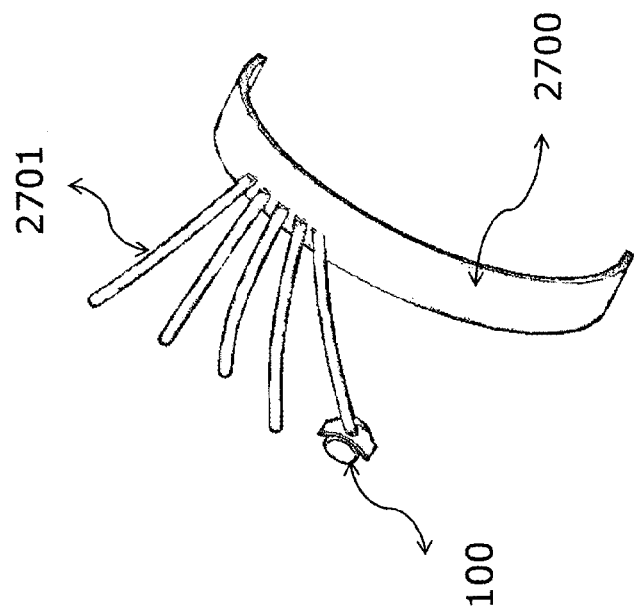
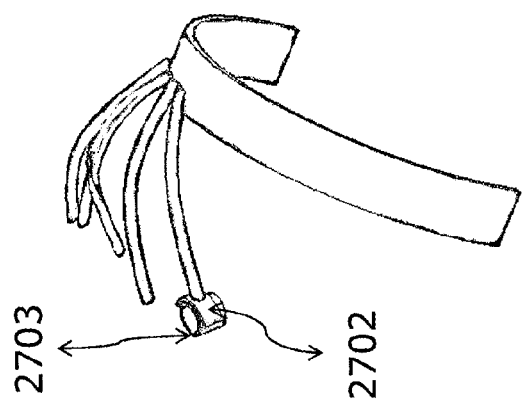
Fig. 27(b)
Fig. 27(a)

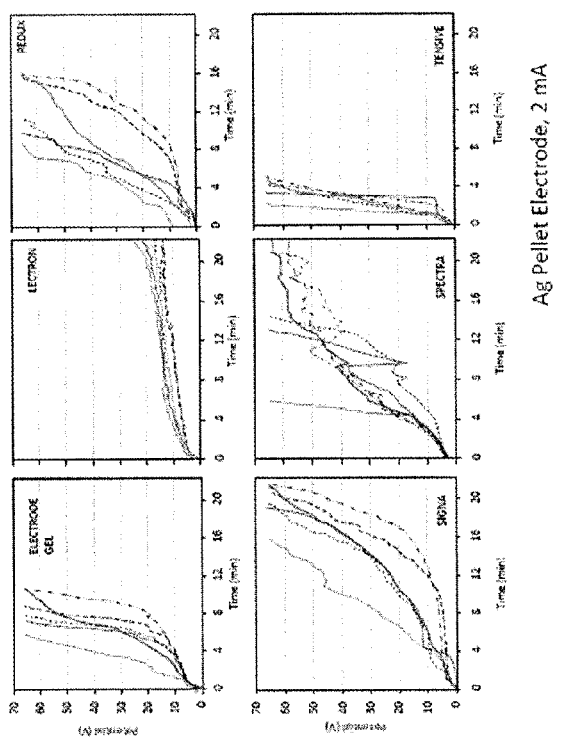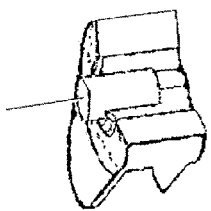
Fig. 29

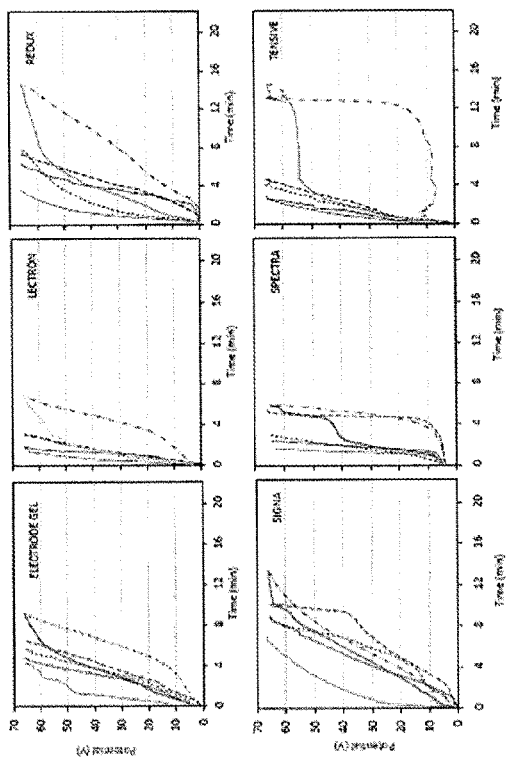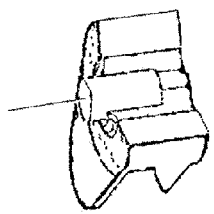
Fig. 30

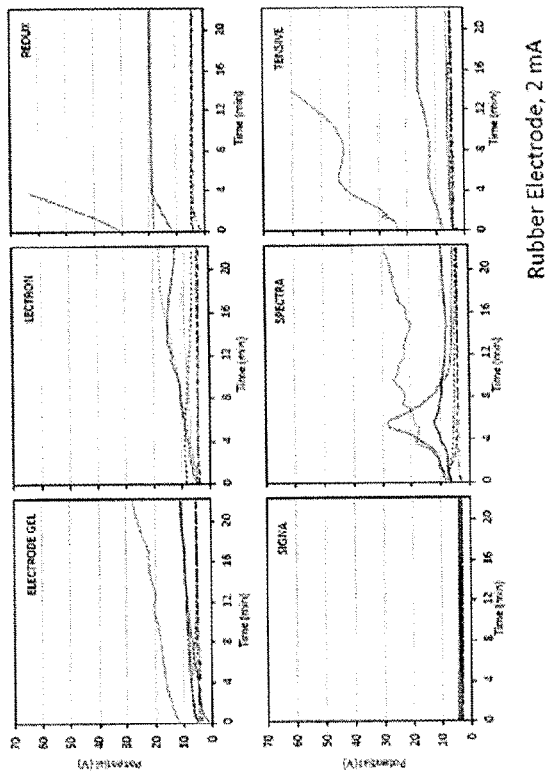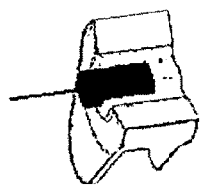
Fig. 31

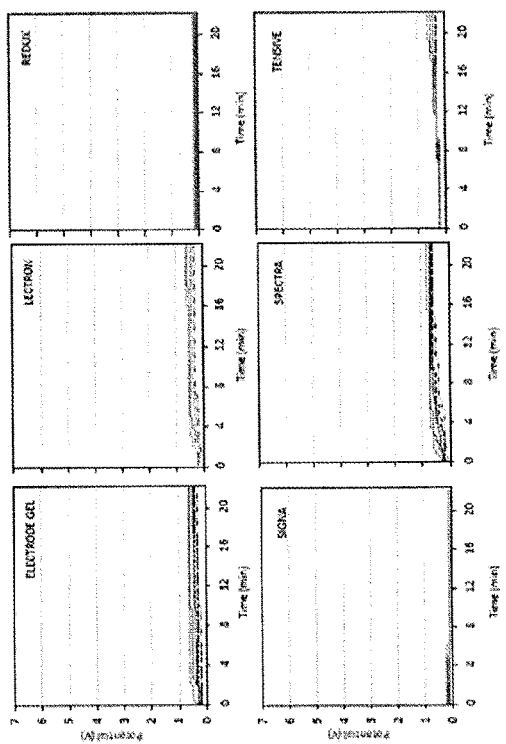
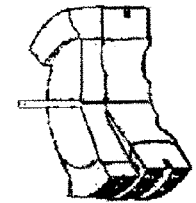
Fig. 32

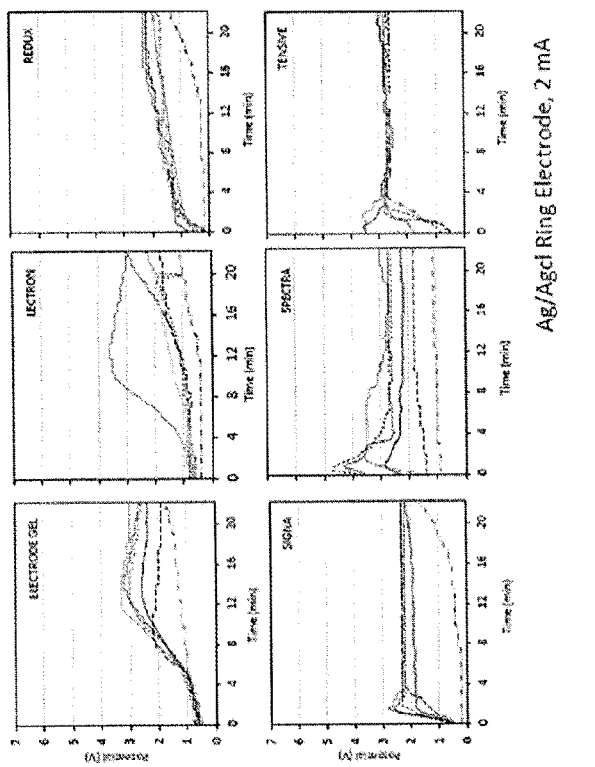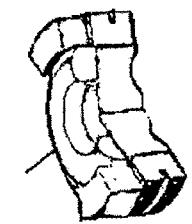
Fig. 33

| Anodal | | | | | | | | | | | | | | | |
|---|---|---|---|---|---|---|---|---|---|---|---|---|---|---|---|
| Electrode | Ag Pellet | | | Ag/AgCl Pellet | | | Rubber Pellet | | | Ag/AgCl Ring | | | | | |
| Gel | Sigma | Lectron | CCNY | Sigma | Lectron | CCNY | Sigma | Lectron | CCNY | Sigma | Lectron | CCNY | | | |
| Pain Score High | 3.5 ± 0.7 | 4.5 ± 0.7 | 3.7 ± 0.5 | 3.2 ± 0.9 | 4.5 ± 0.9 | 3.4 ± 1.9 | 3.6 ± 1.4 | 4.8 ± 1.1 | 3.3 ± 1.5 | 3.0 ± 1.0 | 3.5 ± 0.9 | 3.1 ± 1.2 | | | |
| Pain Score Avg. | 2.5 ± 0.5 | 3.9 ± 1.2 | 2.4 ± 1.0 | 2.4 ± 1.0 | 4.2 ± 1.0 | 2.7 ± 1.6 | 2.9 ± 1.6 | 4.3 ± 1.1 | 2.5 ± 1.5 | 2.0 ± 0.4 | 3.0 ± 1.0 | 2.0 ± 0.9 | | | |
| Withdraw % | 0 | 50 | 0 | 0 | 50 | 20 | 33.3 | 50 | 20 | 0 | 25 | 0 | | | |
| Skin Blisters | 0 | 16.6 | 0 | 17 | 16.6 | 0 | 16.6 | 16.6 | 20 | 16.6 | 0 | 0 | | | |
| ΔT (C) | 1.9 ± 1.3 | 1.1 ± 0.8 | 4.1 ± 2.1 | 2.0 ± 1.5 | 3.3 ± 2.8 | 4.5 ± 0.9 | 0.1 ± 0.2 | 0.2 ± 0.2 | 0.05 ± 0.1 | 0.05 ±0.1 | 0.05 ± 0.1 | 0.05 ± 0.1 | | | |
| ΔpH | 5.9± 0.0 | 6.0 ± 0.0 | 5.9 ± 0.0 | 5.9 ± 0.0 | 6.0 ± 0.0 | 5.9 ± 0.0 | 1.5 ± 0.5 | 6.0 ± 0.0 | 1.2 ± 0.7 | 5.9 ± 0.0 | 6.0 ± 0.0 | 5.9 ± 0.0 | | | |

| Cathodal | | | | | | | | | | | | | | | |
|---|---|---|---|---|---|---|---|---|---|---|---|---|---|---|---|
| Electrode | Ag Pellet | | | Ag/AgCl Pellet | | | Rubber Pellet | | | Ag/AgCl Ring | | | | | |
| Gel | Sigma | Lectron | CCNY | Sigma | Lectron | CCNY | Sigma | Lectron | CCNY | Sigma | Lectron | CCNY | | | |
| Pain Score High | 3.4 ± 0.7 | 3.6 ± 0.7 | 4.1 ± 0.5 | 4.4 ± 0.8 | 4.6± 1.6 | 4.0 ± 1.4 | 4.1 ± 0.5 | 4.3 ± 0.8 | 3.2 ± 1.6 | 3.2 ± 1.6 | 3.8 ± 0.9 | 3.2 ± 1.3 | | | |
| Pain Score Avg. | 2.4 ± 0.5 | 3.3 ± 1.2 | 3.1 ± 1.6 | 3.5 ± 1.6 | 3.7 ± 1.4 | 2.4 ± 1.5 | 3.0 ± 1.3 | 3.7 ± 1.2 | 3.2 ± 1.6 | 1.7 ± 0.7 | 3.0 ± 1.0 | 2.4 ± 1.5 | | | |
| Withdraw % | 0 | 16.6 | 50 | 50 | 50 | 40 | 16.6 | 50 | 40 | 0 | 25 | 20 | | | |
| Skin Blisters | 83 | 67.6 | 0 | 33.3 | 33.3 | 20 | 83.3 | 67.6 | 0 | 0 | 75 | 20 | | | |
| ΔT (C) | 0 | 0 | 0 | 0 | 0 | 0 | 0 | 0 | 0 | 0 | 0 | 0 | | | |
| ΔpH | 12.5 ±0.7 | 6.0 ± 0.0 | 13.5 ± 0.4 | 5.9 ± 0.0 | 6.0 ± 0.0 | 5.9 ± 0.0 | 12.5 ±1.0 | 5.9 ± 0.1 | 12.7 ± 0.7 | 5.9 ± 0.0 | 6.0 ± 0.0 | 5.9 ± 0.0 | | | |

Fig. 37

METHODS FOR REDUCING DISCOMFORT DURING ELECTROSTIMULATION, AND COMPOSITIONS AND APPARATUS THEREFOR

CROSS-REFERENCE TO RELATED APPLICATION

This application is a national phase filing under 35 U.S.C. §371 of International application number PCT/US2009/069843, filed Dec. 30, 2009, which claims the benefit of and priority to U.S. Provisional patent application No. 61/141,469, filed on Dec. 30, 2008 and entitled "A Method for Reducing Discomfort During Electrostimulation & Electrodes Therefor." The entire content of the prior applications are incorporated herein by reference in their entirety.

FIELD OF THE INVENTION

The present invention generally relates to methods, apparatus and compositions for administering neurocranial stimulation, and more particularly to methods, apparatus and compositions for applying neuro-cranial stimulation to particularized areas of the cranium with reduced discomfort and pain.

BACKGROUND OF THE INVENTION

Non-invasive neuro-cranial stimulation is an application of current through one or more electrodes on the neck or head for the purpose of changing function of nervous system. The purpose may be therapeutic including the treatment of neuropsychiatric diseases, epilepsy, depression, Parkinson's disease, Alzheimer's Disease, neuro-degenerative disorders, obesity, and Obsessive-Compulsive-Disorder. The purpose may also be to enhance or accelerate cognitive performance, learning, or perception related tasks.

Non-invasive neuro-cranial stimulation (NINCS) inherently involves passing current through an electrode into or across the skin. Transcranial direct current stimulation (tDCS) is an example of non-invasive neurocranial stimulation in which direct current is applied directly to the scalp in order to pass current to specific brain regions. NINCS can lead to a wide range of discomfort in the subject receiving electrical stimulation. Discomfort can include any perception of tingling, pain, burning, or an otherwise undesirable sensation. Additionally, skin irritation may occur, with such manifestations as flaking, redness, inflammation, burns, or any change in skin properties. Discomfort and irritation may occur together or separately. They typically occur just under or around the electrode, but may occur between electrodes or elsewhere. Discomfort is typically experienced during or immediately after stimulation, but may be felt at longer time points after stimulation has been ceased. Irritation is most pronounced during or right after stimulation, but may be manifested a while after stimulation.

Irritation and discomfort are not desired during NINCS for several reasons. Irritation and discomfort cause pain or discomfort to the subject, complicate the desired effect of stimulation, and can lead to adverse health effects. Further, irritation and discomfort may prevent optimal application of NINCS and reduce a subject's desire to receive NINCS.

Conventional tDCS (a type of NINCS) employs the passage of a constant direct current (nominally 260 uA-3 mA) between an anode and cathode electrode, at least one of which is placed over the scalp. The spatial focality (targeting) of tDCS is considered pivotal for efficacy and safety. Decreasing electrode scalp contact area is considered to improve spatial focality. But for a given electrode current, reducing contact area increases current density, which in turn may increase hazards.

From the perspective of tDCS safety, it is important to consider 1) injurious effects of electrical currents on the brain; and 2) pruritic, painful, or injurious effects of electrical currents on the skin. Brain injury and skin effects are not necessarily linked, and therefore should be considered independently. For example, stimulation causing skin irritation may not have any adverse effect on brain function, and brain injury may not be concomitant with skin irritation.

The prior art electrodes fail to address minimizing skin irritation and pain during electro-stimulation activities like NINCS, particularly tDCS. It is an object of the invention to optimize electrode parameters to minimize skin irritation and pain, with a specific focus on engineering small, more focal electrodes.

SUMMARY OF THE INVENTION

According to a first aspect of the invention, there is provided an electrode assembly for neuro-cranial stimulation comprising:

an adapter including a receiver for attachment of an electrode, and a holder for use with an electrode and conductive gel or paste having a holder reservoir for storing the gel or paste, the holding reservoir having rigid or semi-rigid wall restricting the flow of the gel or paste; and attaching means for attachment of the holder to the scalp of a subject.

According to a second aspect of the invention, there is provided a method to reduce irritation, sensation, discomfort, injury, burns, perception, inflammation, pain, or redness during neurocranial stimulation comprising a neurocranial stimulation device and electrode apparatus detailed in the present invention.

According to a third aspect of the invention, there are provided compositions for neurocranial stimulation gels that reduce or prevent irritation, sensation, discomfort, injury, burns, perception, inflammation, pain, or redness.

According to a fourth aspect of the invention, there is provided a method to reduce irritation, sensation, discomfort, injury, burns, perception, inflammation, pain, or redness during cranial neurostimulation comprising selecting an appropriate combination of (1) gel and (2) solid conductor which support, control, or limit electrolyte depletion or formation at the cathode or anode.

According to a fifth aspect of the invention, there are provided specific combinations of (1) gel and (2) solid conductor of the electrode that allow for the reduction or prevention of irritation, sensation, discomfort, injury, burns, perception, inflammation, pain, or redness during cranial neurostimulation.

According to a sixth aspect, there is provided a method to reduce irritation, sensation, discomfort, injury, burns, perception, inflammation, pain, or redness during neurocranial stimulation comprising the steps of:

selecting a suitable electrode-skin contact area;
selecting a suitable metal electrode material;
selecting an electrode shape;
selecting a rigid or semi-rigid holder;
selecting an appropriate gel;
selecting a chemical to apply to the gel or the skin;
selecting a temperature for the gel/skin;

combining the electrode and gel in the holder, wherein said holder determines the shape and volume of the gel, the position of the electrode relative to the gel, and the portion of skin exposed to the gel;

preparing the skin;

attaching the assembly to the head of an individual with suitable attachment means;

checking the electrode properties such as resistance; and/or selecting a conditioning electrical waveform to apply to the skin;

According to an seventh aspect, there is provided an apparatus for applying transcranial current through the scalp using a plurality of electrodes, each electrode comprising:

at least one rigid or semi-rigid shell with a distal end contacting the scalp and a proximal end with a portion of the shell encompassing a portion of a gel, at least one electrical stimulation electrode with a proximal end and a distal end, the distal end making contact with a portion of the gel, and gel or paste contacting the scalp and containing no electrolytes, minimal electrolytes, or one or more electrolytes, and a cap or mesh positioned on the scalp and connected to the semi-rigid shell.

According to an eighth aspect, there is provided an apparatus for applying transcranial current through the scalp using a plurality of electrodes, each electrode comprising:

at least one semi-rigid shell with a distal end contacting the scalp and a proximal end with a portion of the shell encompassing a portion of the secondary gel;

at least one electrical stimulation electrode with a proximal and distal end making contact with a portion of the primary gel containing no electrolytes, minimal electrolytes, or one or more electrolytes;

a secondary gel contacting a portion of the primary gel and the scalp; wherein the secondary gel may contain no electrolytes or one or more electrolytes.

According to a ninth aspect, there is provided an apparatus for applying transcranial current through the scalp using a plurality of units, each unit comprising:

at least one semi-rigid shell with a distal end contacting the scalp and proximal end;

a electrode mount with one portion contacting the semi-rigid shell and one portion contact the electrical stimulation electrode;

at least one electrical stimulation electrode with a proximal and distal end making contact with a portion of the gel;

and a gel or paste contacting the scalp and containing no electrolytes or one or more electrolytes.

According to a tenth aspect, there is provided a transcranial stimulation electrode comprising: an electrically conductive backing and an electrically conductive hydrogel matrix coated thereupon, said matrix being adapted to make contact with the skin of the patients and being sufficiently flexible to conform to the contours of the body.

In a different field, electroencephalography uses small head electrodes and involves measuring brain potentials rather than applying brain-stimulating electrical currents. These small electrodes have not been used or discussed before for neurocranial stimulation, because it was considered that the application of desired neurocranial stimulation current levels with small head electrodes would result in current densities sufficiently high to cause significant pains and/or discomfort. As a result of extensive experimentation described further herein, applicants discovered that the small head electrodes disclosed in the prior art could be modified for effective use in neurocranial stimulation, under particular design conditions which form a part of their invention as described herein. Applicants incorporate by reference herein the following patents which describe prior art electroencephalography electrodes: U.S. Pat. Nos. 6,640,122, 6,574,513, 6,445,940, 6,201,982, 6,175,753, 6,161,030, 4,171,696, 4,537,198, 4,683,892, 5,357,957, 5,479,934, 5,511,548, 5,630,422, 5,730,146, 5,740,812, 5,800,351, 6,047,202, 6,067,464, 537,198, 4,632,120, 4,709,702, 4,770,180, 4,836,219, 4,967,038, 5,038,782, 5,273,037, 5,291,888, 5,293,867, 5,348,006, 5,357,957, 5,404,875, 5,479,934, 5,564,433, 5,740,812, 5,800,351, 5,813,993, 6,067,464, 6,161,030, 6,167,298, 6,175,753, 6,201,982, 6,301,493, 6,381,481, 4,683,892, 4,709,702, 5,038,782, 5,479,934, 6,067,464, 6,155,974, 4,067,321, 4,632,120, 4,709,702, 4,936,306 and 5,222,498.

Other electrodes have been used for the purpose of drug delivery through the skin (transdermal drug delivery). These electrodes have not generally been used for electrical stimulation, electrotherapy, or neurocranial stimulation, but may also be suitable when modified according to principles of the present invention for neuro-cranial stimulation. Applicants incorporate by reference herein the following patents which describe this prior art: U.S. Pat. Nos. 4,177,817, 4,196,737, 5,282,843, 4,736,752, 3,817,252, 4,503,863, 4,535,779, 7,392,096, 6,343,226, 4,736,752, 4,367,755 and 7,421,299.

DEFINITIONS

The following words and terms used herein shall have the meaning indicated:

Unless specified otherwise, the terms "comprising" and "comprise", and grammatical variants thereof, are intended to represent "open" or "inclusive" language such that they include recited elements but also permit inclusion of additional, un-recited elements.

As used herein, the term "about", in the context of concentrations of components of the formulations, typically means +/−20% of the stated value, more typically +/−10% of the stated value, more typically +/−5% of the stated value, more typically, +/−2% of the stated value, even more typically +/−1% of the stated value, and even more typically +/−0.5% of the stated value. Throughout this disclosure, certain embodiments may be disclosed in a range format. It should be understood that the description in range format is mainly for convenience and brevity and should not be construed as an inflexible limitation on the scope of the disclosed ranges. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

BRIEF DESCRIPTION OF DRAWINGS

The foregoing and other features of the present invention will be more readily apparent from the following detailed description and drawings of illustrative embodiments of the invention, in which:

FIGS. 14(a) and 14(b) illustrate the adapter of FIG. 1 with a preloaded gel, electrode, shield and cap.

FIGS. 27(a)-28 illustrate electrode assembly mounting apparatus according to the present invention that include flexible arms that receive and position the electrode assemblies.

FIGS. 29 and 30 illustrate electrode potential results for trials employing electrode assemblies having pellet type electrodes.

FIG. 31 illustrates electrode potential results for trials employing electrode assemblies having rubber-type electrodes according to the present invention.

FIG. 32 illustrates electrode potential results for trials employing electrode assemblies having Ag/AgCl disc electrodes according to the present invention.

FIG. 33 illustrates electrode potential results for trials employing electrode assemblies having Ag/AgCl Ring electrodes according to the present invention.

FIG. 37 presents tables showing electrochemical behavior and summary of time and pain performance using a variety of gels and variety of electrodes according to the present invention.

Like reference numerals are used in the drawing figures to connote like elements of the invention.

DETAILED DESCRIPTION OF THE INVENTION

Figure 1:
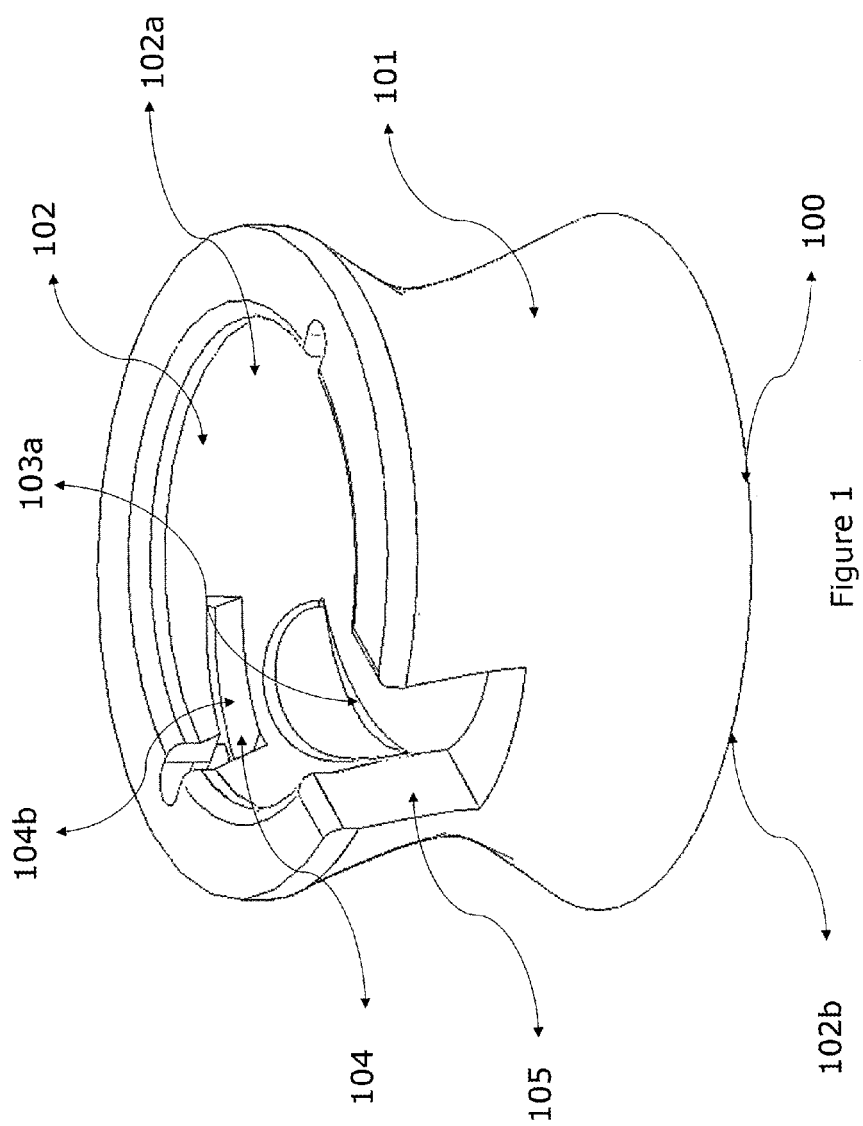
FIG. 1 illustrates an adapter element of an electrode assembly in accordance with the present invention.

Medical electrodes have, in the past, taken many shapes and forms. Electrodes used in monitoring apparatuses, such as EKG and EEG, where little or no current is passed across the electrodes, have commonly round contact surfaces, whereas electrodes used in stimulation apparatus devices tend to be larger and have rectangular surfaces. For example, electrodes for transcranial direct current stimulation have taken the form or large square sponges. High current densities at specific areas on the head are desirable for efficacy of the electrical stimulation protocol, and current electrodes do not optimize these parameters. Small electrodes are ideal for the attainment of that efficacy and advancement of the field. However, it has commonly been believed that the use of small electrodes, or specifically higher current densities, would result in skin pain and injury.

We discovered that using appropriately designed small electrodes, high currents (high current densities) could be applied to the skin safely and comfortably. This discovery challenges conventional perceptions widely held by experts in the field.

The objective of this invention as accomplished herein is a practical small medical electrode suitable for neurocranial electrical stimulation and, in a preferred embodiment, transcranial direct current stimulation. The main goal is the ability to deliver desired levels of current in a way that is safe and comfortable for the patient. Previous electrode designs are unsuitable for several reasons. Large electrodes must be made flexible to accommodate the curvature of the skin. This results in poor control of the skin interface, for example the amount of gel or other material between the metal electrode and skin. This has shown to result in current hot-spots and injury. Small electrodes have been attempted, but previous designs of small electrodes were unsuitable for various reasons. In some designs a flexible (adhesive) back is used, which does not strictly regulate the metal skin distance. And in other previous designs, a "low profile" configuration results in insufficient distance between the metal and the skin. In the invention contained herein, electrodes are presented which fix the electrode position relative to the skin, maintain a minimum distance between metal and skin, and are able to improve and replicate the functionality of large electrodes in a safe and effective way.

According to a first aspect of the invention, there is provided an electrode assembly for neuro-cranial stimulation comprising:

an adapter including a receiver for attachment of an electrode and a holder for use with an electrode and conductive gel or paste having a holder reservoir for storing the gel or paste, the holding reservoir having rigid or semi-rigid wall restricting the flow of the gel or paste; and attaching means for attachment of the holder to the scalp of a subject.

In order to ensure skin safety and comfort during transcranial stimulation, electrodes must be designed properly as described in this invention. It is also necessary to ensure electrode voltages do not increase to too high a level. This design requires the balance of several engineering factors. We have found three properties which are critical for effective, safe electrode apparatuses.

First, gel-skin contact area should be within a desired range. The area should be minimized as to localize the location of current entry, and in order to practically control the uniformity of contact. However, the area should be maximized in order to reduce discomfort by distributing the current, and the area may be maximized in relation to (scaled by) the amount of current that will be passed.

Second, the distance between the nearest components of electrode and skin should be maximized, while the overall head-gear and electrode profile is not too high (i.e. standing far off of the head) that it is not practical. Classical electrodes used on the head, for example those used for EEG, lie directly on or very close to the surface of the scalp. However, when applying large currents to the scalp, such as in neurocranial stimulation, there is a potential hazard from direct contact of the electrode with the skin. Therefore, it is of critical importance that electrodes and their holders be designed so that there is sufficient separation between the scalp and electrode. Additionally, one must also consider that the skin is not flat but rather flexible and so will protrude into the electrode assembly to a varying degree depending on the size of the opening. The desired apparatus, and those holders described in this invention, therefore have a specific depth which physically positions the electrode away from the skin by utilizing a holder that a) holds the electrode at a certain height and b) keeps the skin from protruding into the electrode area. Note that (b) can be done by either limiting the area of the electrode (pellet) or using fins (ring). The reasons for maintaining this distance are several fold including buffering electrochemical products, preventing contact between electrode and skin, and allow current to distribute evenly throughout the gel.

Third, the contact area between the metal electrode and the gel should be maximized within the given constraints of the holder volume and electrode size. If the electrode contacts only one surface of the gel material, the electrode-gel interface is an essentially a 2-dimensional interface. However, if the metal electrode is immersed in the gel, this becomes a 3-D interface, thus greatly increasing surface area. For example, a pellet electrode can be fit into a small diameter cylindrical plastic holder. The plastic holder has a small skin contact area, but its depth allows the use of longer pellets with increased surface area. Though, in our ring design the electrode contact area is actually less than the skin contact area.

Specific examples of electrodes embodying these important concepts necessary to optimize voltage and safety, and the descriptive embodiments mentioned below, are illustrated in the drawing figures. In essence, the electrode holder is a rigid or semi-rigid material exposed at two ends, which is able to hold a volume of gel and an electrode.

In one embodiment, the electrode holding reservoir is cylindrical, conical, square, rectangular, circular, or a more complex permutation of these shapes. In a preferred embodiment, the holder is a cylinder or hyperboloid of a suitable volume for holding both the electrode and gel material.

The material out of which the holder is made can be any rigid or semi-rigid material suitable to hold in place both a gel and an electrode. In one embodiment, the holder is made out of a material selected from the group consisting of, but not limited to, plastic, sponge, or ceramic. In a preferred embodiment, the holder is made out of semi-rigid plastic.

For example, FIG. 1 illustrates an adapter 100 of an electrode assembly according to the present invention. The adapter 100 comprises a body 101 including an interior compartment 102 having an interior surface that is substantially hyperbolical. The interior compartment 102 includes a first compartment 102a for positioning an electrode of the electrode assembly, and a second compartment 102b for receiving a conductive gel of the electrode assembly. The compartments 102a, 102b are in fluid communication with one another, thereby permitting the conductive gel provided in the second compartment 102b to flow into the first compartment 102a for the purpose of coming into physical contact with the electrode.

Figure 2:
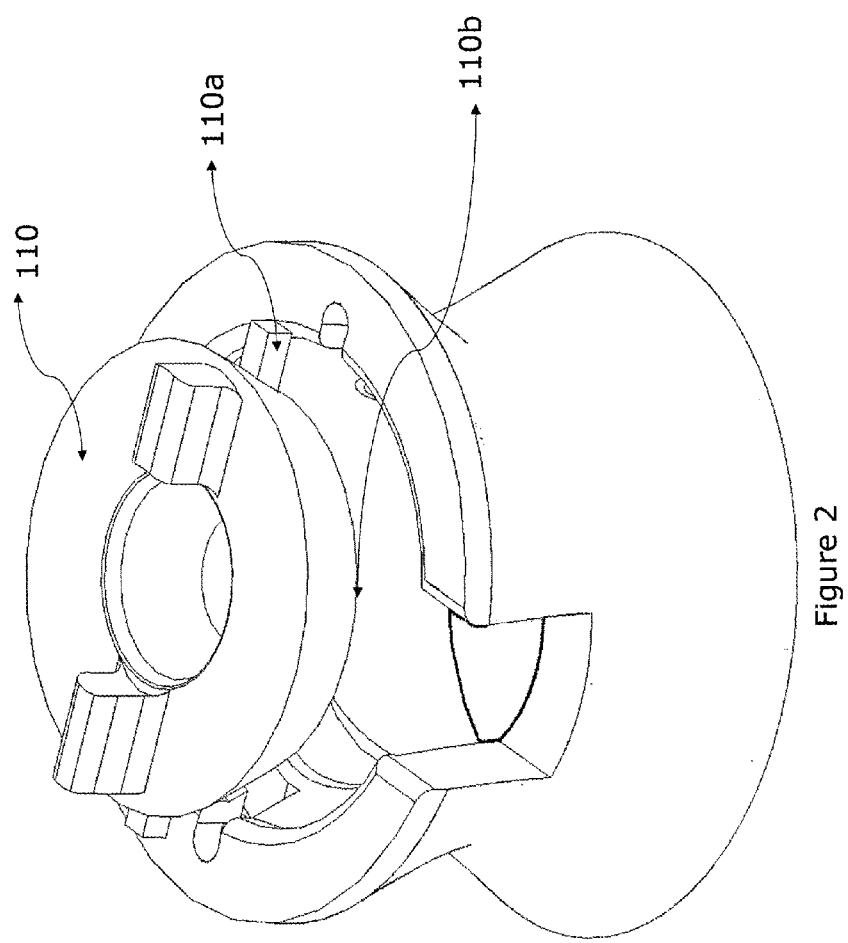
FIG. 2 illustrates the adapter of FIG. 1 in combination with a cap element provided in an unlocked position.

The first compartment 102a further comprises indentations 103 each including a land surface 103a for carrying a bottom surface of the electrode, grooves 104 for receiving tabs 110a of a cap 110 as illustrated in FIG. 2, and a channel 105 that defines a passageway through which an electrical conductor of the electrode may extend away from the first compartment 102a.

Figure 3:
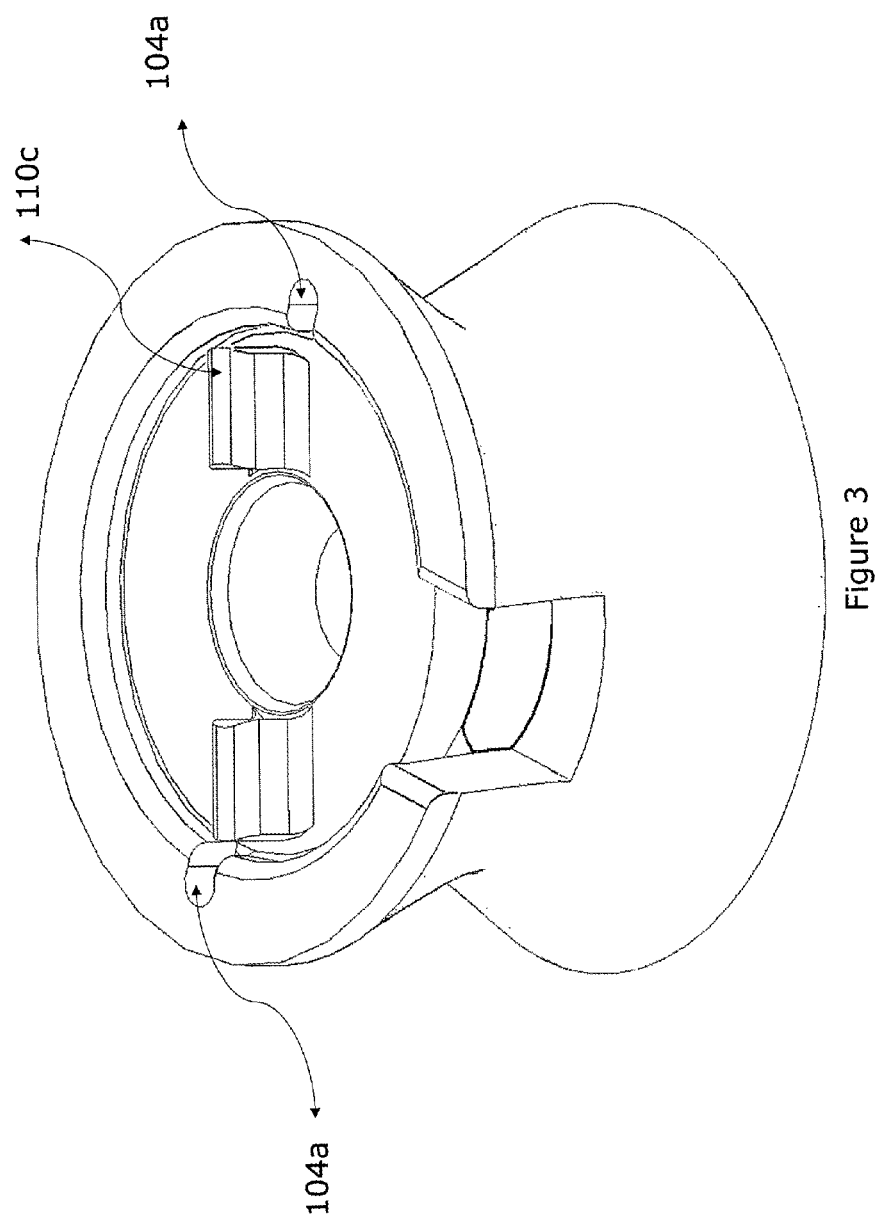
FIG. 3 illustrates the adapter of FIG. 2 with the cap element provided in a locked position.
Figure 4:
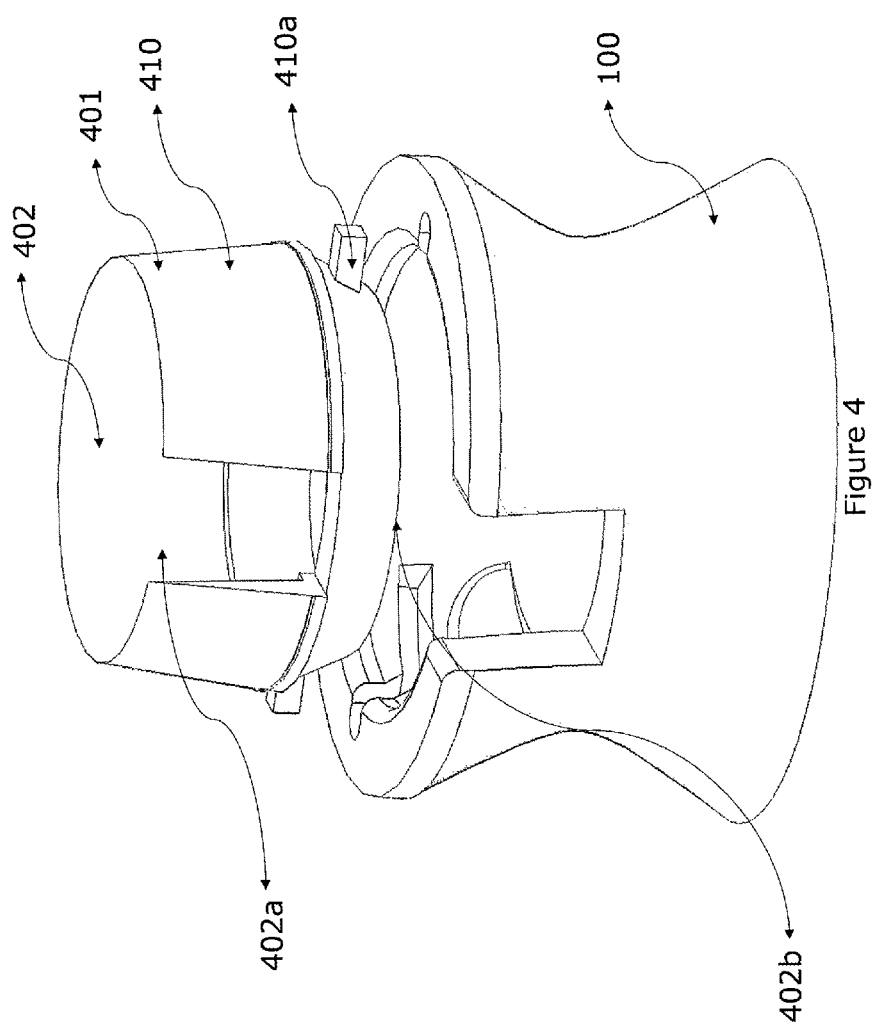
FIG. 4 illustrates the adapter of FIG. 1 in combination with an accessory element.
Figure 5:
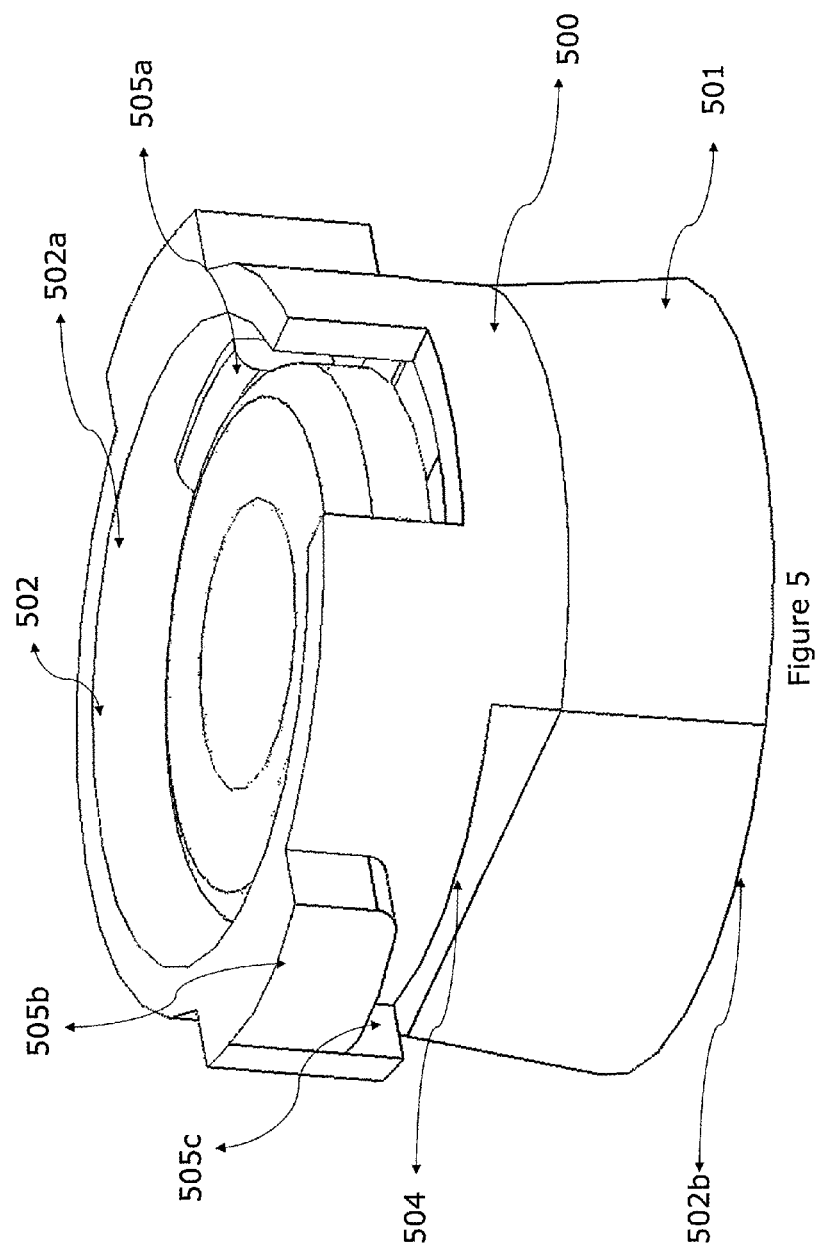
FIG. 5 illustrates another adapter of an electrode assembly in accordance with principles of the present invention.

As illustrated in FIG. 3, each tab 110a of the cover 110 may be inserted into a vertical portion 104a of a corresponding groove 104 to enable the cap 110 to be sealably positioned within a top portion of the first compartment 102a. The cap 110 includes a surface 110b which is shaped to conformally and sealably contact a corresponding surface portion of the top portion of the first compartment 102a upon insertion into the first compartment 102a. As illustrated in FIGS. 1 and 3, upon insertion into the first compartment 102a, tabs 110c may be manipulated to rotate the cap 110 so that the tabs 110a move outwardly along horizontal portions 104b of the grooves 104 toward a closed position of the cap 110. As can be seen with reference to FIG. 1, the portions 104b extend slightly downwardly along the horizontal direction so that, as the tabs 110a move outwardly along the portions 104b, the surface 110b is pressed against the corresponding surface portion of the top portion of the first compartment 102a to generate a reciprocal force that effectively fixes or locks the cap 110 to the body 101 in the closed position. FIG. 4 illustrates an accessory 410 to be mounted on to the adapter 100. Each tab 410a of an accessory 410 may be inserted into a vertical portion 104a of a corresponding groove 104 to enable the accessory 410 to be locked on to the adapter 100. The accessory 410 comprises a body 401 including an interior surface 402. The interior surface 402 is divided into a first compartment 402a for positioning an electrode of the electrode assembly, and a second compartment 402b for receiving the conductive gel of the electrode assembly. The compartments 402a, 402b and 102a are in fluid communication with one another. FIG. 5 illustrates an adapter 500 of an electrode assembly according to the present invention. The adapter 500 comprises a body 501 including an interior surface 502 having two compartments: a first compartment 502a for positioning an electrode of the electrode assembly, and a second compartment 502b for receiving a conductive gel of the electrode assembly. Compartments 502a and 502b are divided by an indentation 503 from the surface 501. These indentations 503 form a land surface 504 on the interior surface 502 for carrying a bottom surface of electrode. Two protrusions 505a are designed for holding of the electrode at a distance from the side surface of electrode. In this case, the electrode can be mounted from the top so that the bottom surface of electrode sits on land surface 504 while protrusions 505a isolate the electrode from any movement from two opposite sides. Protrusions 505b and 505c are shaped to conformally and sealably lock a cap 510 as illustrated in FIG. 6 onto the adapter 500.

Figure 6:
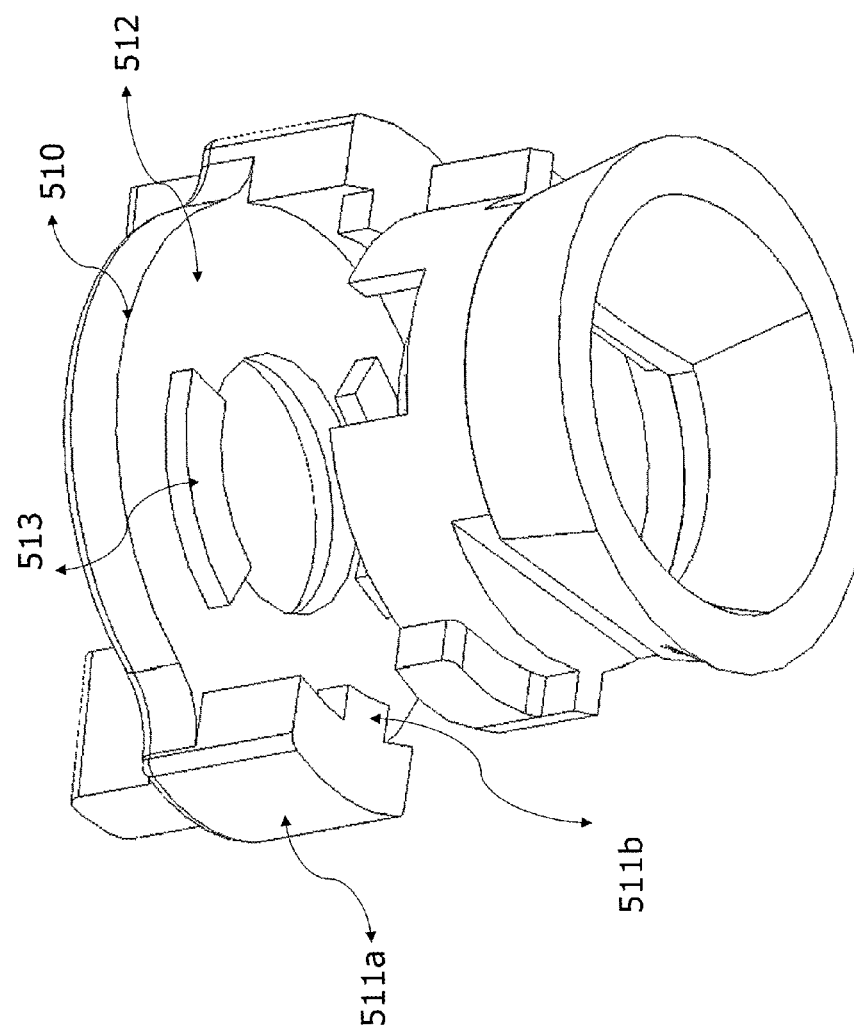
FIG. 6 illustrates the adapter of FIG. 5 in combination with another cap element provided in an unlocked position.

The cap in FIG. 6 has protrusions 511. Two vertical extruded bars 511a and horizontal extrusions 511b are positioned underneath protrusions 505b during locking of the cap 510 on adapter 500.

Figure 7:
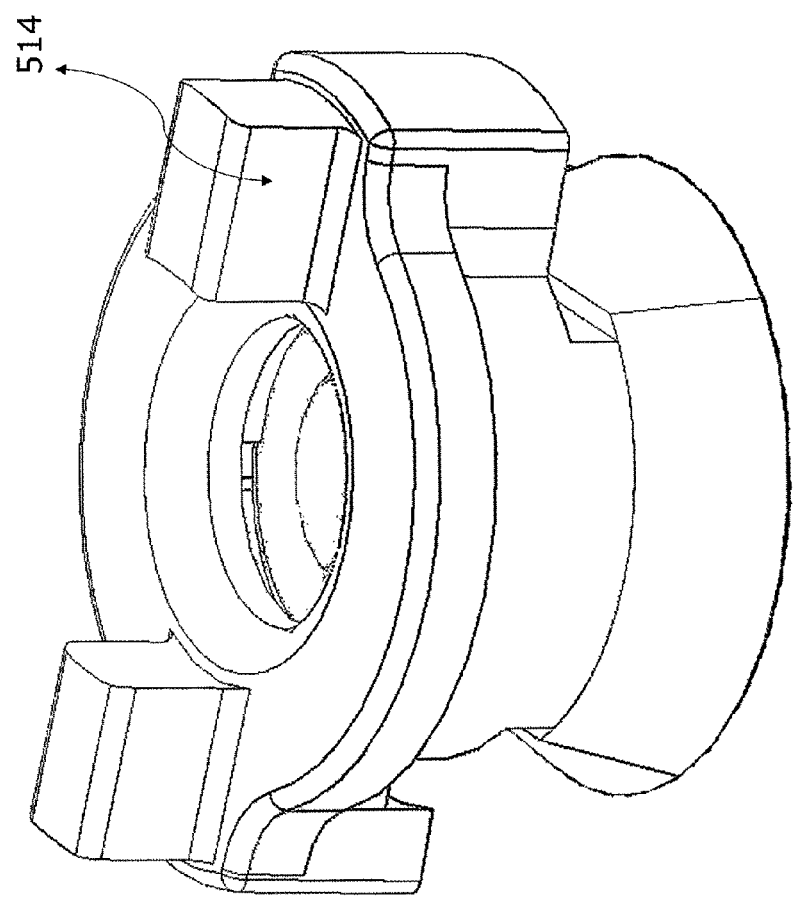
FIG. 7 illustrates the adapter and cap of FIG. 6 with the cap provided in a locked position.

As illustrated in FIGS. 5-7, each extrusion 511b of the cap 510 may be inserted underneath a protrusion 505b to enable the cap 510 to be securely and tightly positioned on an upper portion of first compartment 502a. The cap 510 includes a surface 513 which is shaped to conformally and sealably contact a corresponding surface portion of the top portion of the first compartment 502a upon insertion into the first compartment 502a. As illustrated in FIGS. 6 and 7, upon insertion into the first compartment 502a, tabs 514 may be manipulated to rotate the cap 510 so that the tabs 510a move outwardly along horizontal protrusions 505b of the extrusion 505 toward a closed position of the cap 510. As can be seen with reference to FIG. 6, the protrusions 505b extend slightly downwardly along the horizontal direction so that, as the tabs 511b move outwardly along the protrusions 505b, the surface 513 is pressed against the corresponding surface portion of the top portion of the first compartment 502a to generate a reciprocal force that effectively fixes or locks the cap 510 to the body 501 in the closed position.

Figure 8:
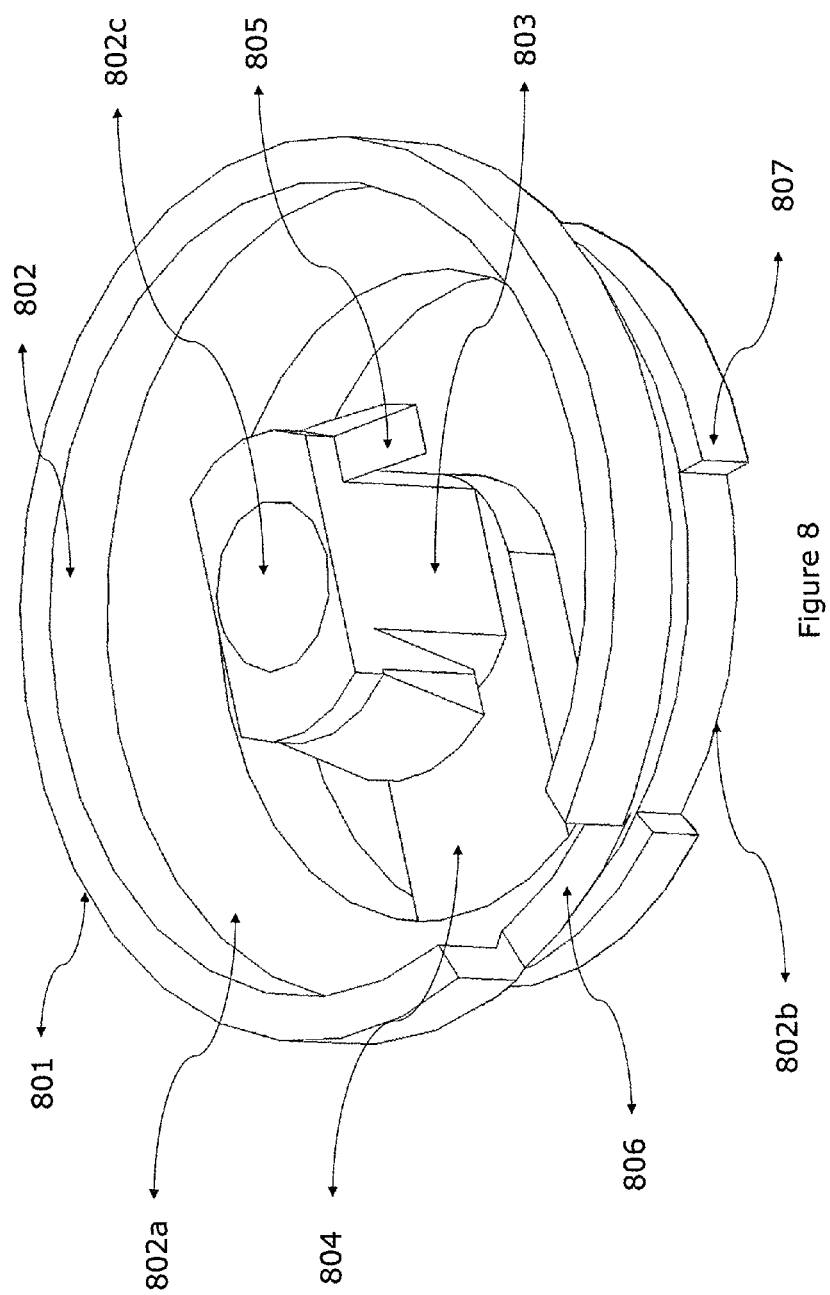
FIG. 8 illustrates another adapter of an electrode assembly in accordance with principles of the present invention.

FIG. 8 illustrates an adapter 800 of an electrode assembly according to the present invention. The adapter 800 comprises a body 801 including an interior surface 802 that has 2 large compartments upper compartment 802a with large radius for the positioning of electrode and a lower compartment 802b with small radius for receiving conductive gel. The compartment 802a, 802b are in fluid communication with one another, thereby permitting the conductive gel provided in the second compartment 802b to enter the first compartment 802a for the purpose of coming into physical contact with the electrode.

From the inner surface of 802, a horizontal extrusion 804 extends into the center of upper compartment 802a. A vertical extrusion 803 extends from horizontal extrusion 804 and includes a compartment 802c. Compartments 802c and 802b are in fluid communication with one another. A bottom surface of an electrode sits on the top surface of 804. Outward angular extrusions 805 extend from the extruded body 803 for tightening and holding the electrode at a central hole of electrode. The extrusions 805 move inwardly in response to the push of the electrode onto the body 803 to tightly hold the electrode in position.

Figure 9:
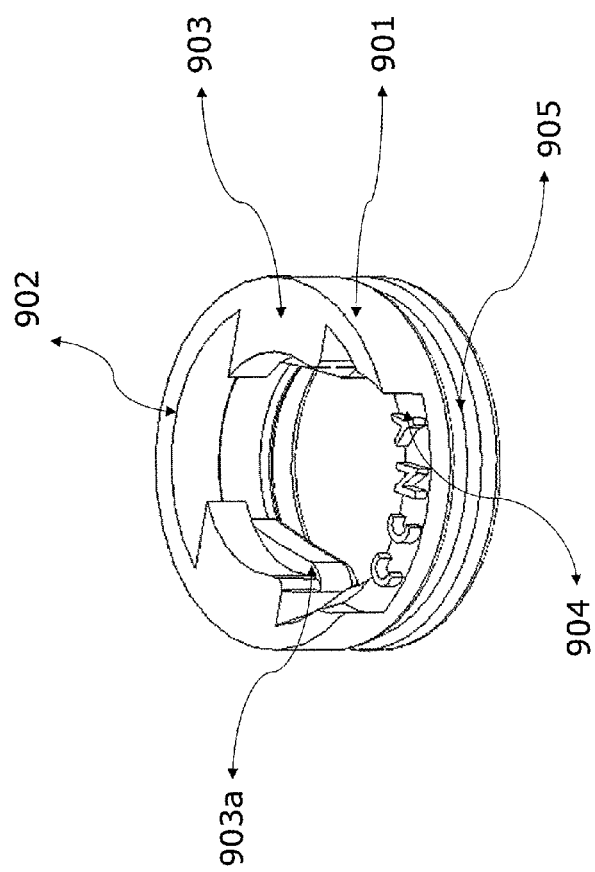
FIG. 9 illustrates another adapter of an electrode assembly in accordance with principles of the present invention.

FIG. 9 illustrates an adapter 900 of an electrode assembly according to the present invention. The adapter 900 comprises a body 901 including an interior cylindrical surface 902. The cylindrical surface 902 defines a first compartment 902a for positioning an electrode of the electrode assembly, and a second compartment 902b for receiving a conductive gel of the electrode assembly. The compartments 902a, 902b are in fluid communication with one another, thereby permitting the conductive gel provided in the second compartment 902b to enter the first compartment 902a for the purpose of coming into physical contact with the electrode.

The first compartment 902a further comprises indentations 903 each including a land surface 903a for carrying a bottom surface of the electrode and a channel 904 that defines a passageway through which an electrode may be inserted into the first compartment 902a. Alternatively, the electrode in the adapter 900 may be mounted from top portion of 902a. A groove 905 on the outer wall of adapter 900 may be used to hold the adapter 900 tightly in position within a mounting apparatus.

Figure 10:
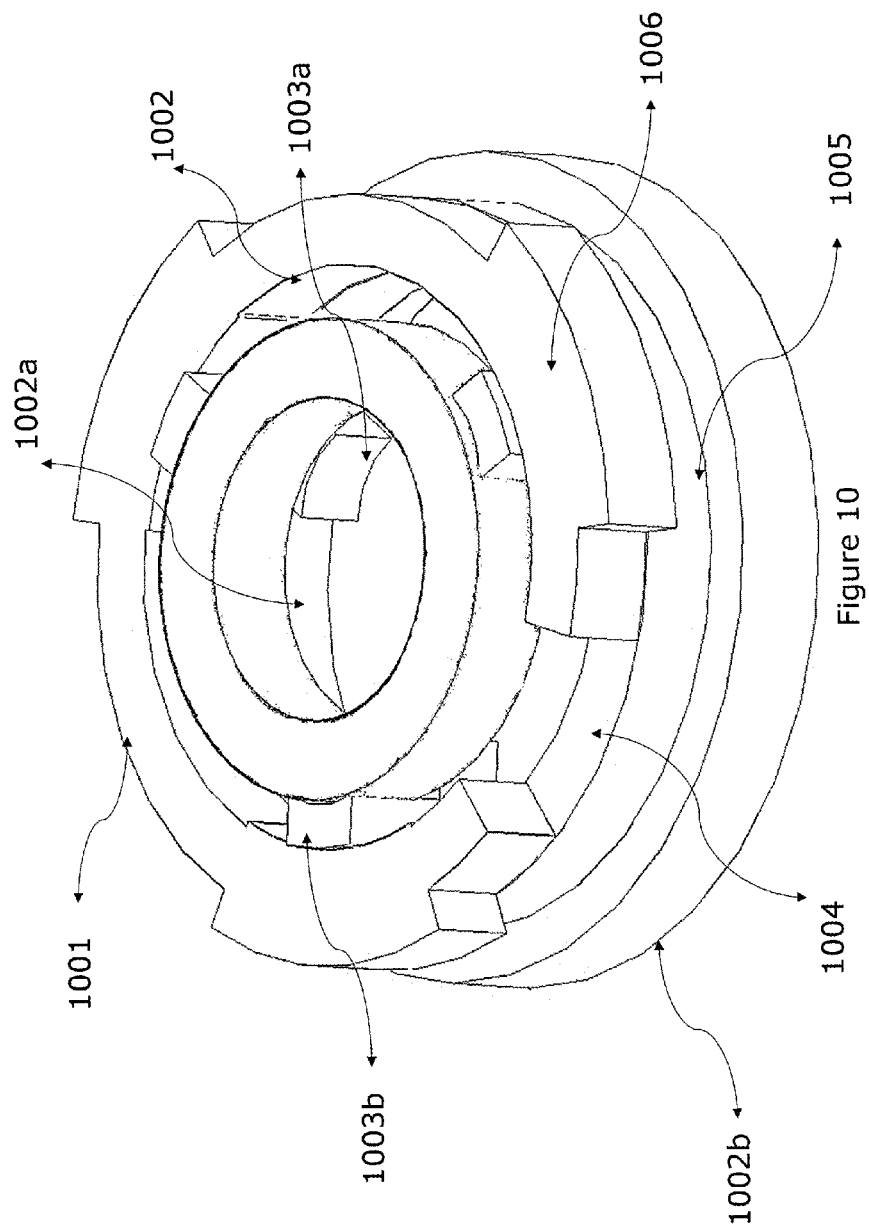
FIG. 10 illustrates another adapter of an electrode assembly in accordance with principles of the present invention.

FIG. 10 illustrates an adapter 1000 of an electrode assembly according to the present invention. The adapter 1000 comprises a body 1001 including an interior cylindrical surface 1002. The cylindrical surface 1002 defines a first compartment 1002a for positioning an electrode of the electrode assembly, and a second compartment 1002b for receiving a conductive gel of the electrode assembly. The compartments 1002a, 1002b are in fluid communication with one another, thereby permitting the conductive gel provided in the second compartment 1002b to enter the first compartment 1002a for the purpose of coming into physical contact with the electrode.

The first compartment 1002a further comprises extrusions 1003 each including a land surface 1003a for carrying a bottom surface of the electrode and vertical bars 1003b for holding electrode in position. A channel 1004 defines a passageway through which an electrical conductor of the electrode may extend away from the first compartment 1002a. An electrode in the adapter 1000 may be mounted from top portion of first compartment 1002a. A groove 1005 on the outer wall of adapter 1000 includes 3 flap like extrusions 1006 on the top which assist in mounting of adapter 1000 on a mounting apparatus.

Figure 11:
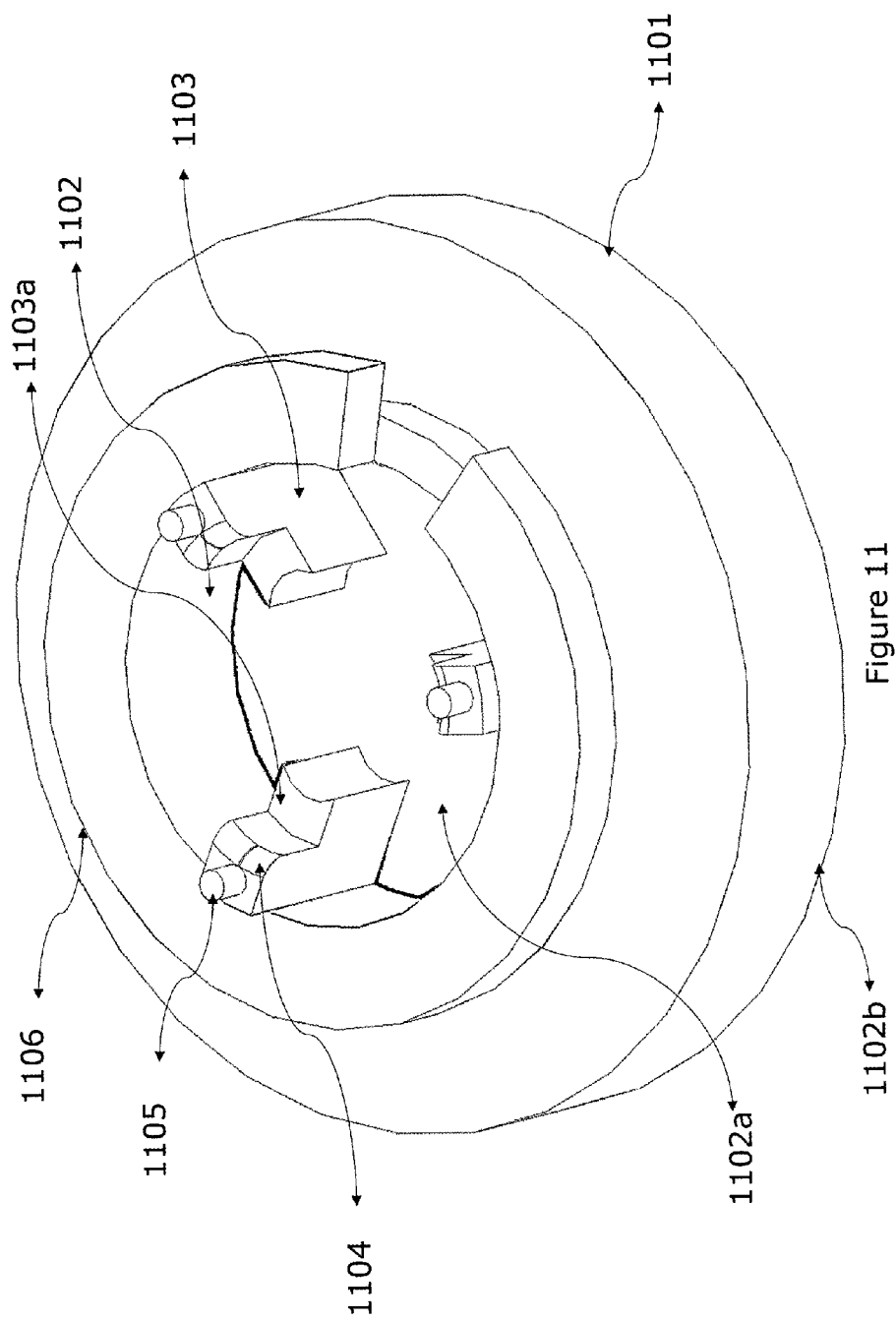
FIG. 11 illustrates another adapter of an electrode assembly in accordance with principles of the present invention.

FIG. 11 illustrates an adapter 1100 of an electrode assembly according to the present invention. The adapter 1100 comprises a body 1101 including an interior cylindrical surface 1102. The cylindrical surface 1102 defines a first compartment 1102a for positioning an electrode of the electrode assembly, and a second extended wide compartment 1102b for receiving a large volume of conductive gel and of the electrode assembly. The compartments 1102a, 1102b are in fluid communication with one another, thereby permitting the conductive gel provided in the second compartment 1102b to enter the first compartment 1102a for the purpose of coming into physical contact with the electrode.

Figure 12:
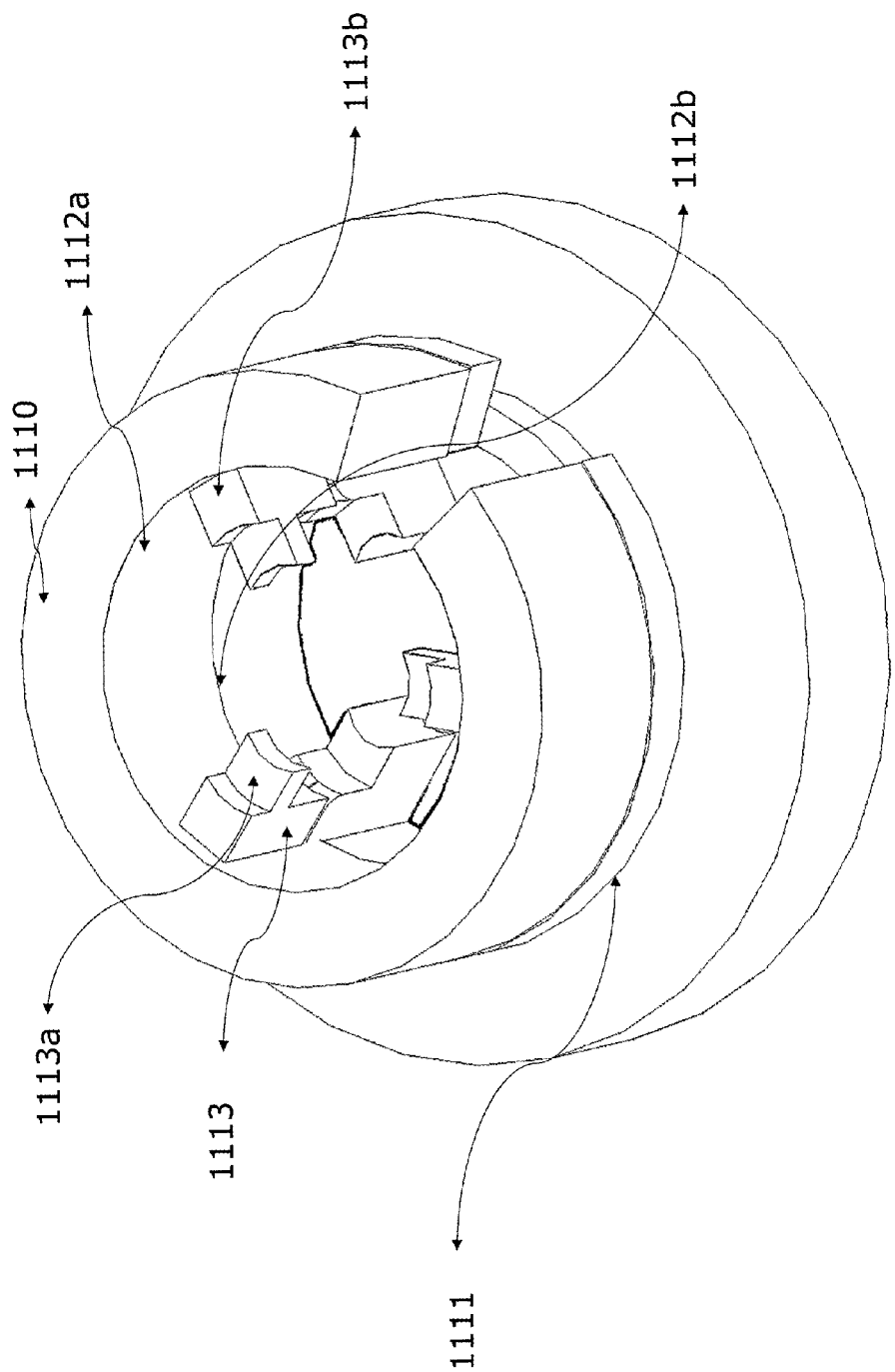
FIG. 12 illustrates the adapter of FIG. 11 in combination with an accessory element.

The first compartment 1102a further comprises indentations 1103 each including a land surface 1103a for carrying a bottom surface of the electrode and bars 1104 for holding the electrode Tabs 1105 protrude from a top part of bars 1104 for holding an accessory element 1110 as illustrated in FIG. 12. A bottom portion 1111 of the accessory 1110 fits on the top portion 1106 of adapter 1100.

As illustrated in FIG. 12, accessory 1110 includes an interior cylindrical surface 1112 with extrusions 1113 that includes a horizontal extrusion 1113a for positioning another electrode and vertical bars 1113b for holding electrodes. The cylindrical surface 1112 defines a first compartment 1112a for positioning an electrode of the electrode assembly, and a second compartment 1112b for receiving conductive gel. The compartments 1102a, 1112b and 1112a are in fluid communication with one another, thereby permitting the conductive gel provided in the second compartment 1112b to enter the first compartment 1112a and 1102a for the purpose of coming into physical contact with both of the electrode.

Figure 13:
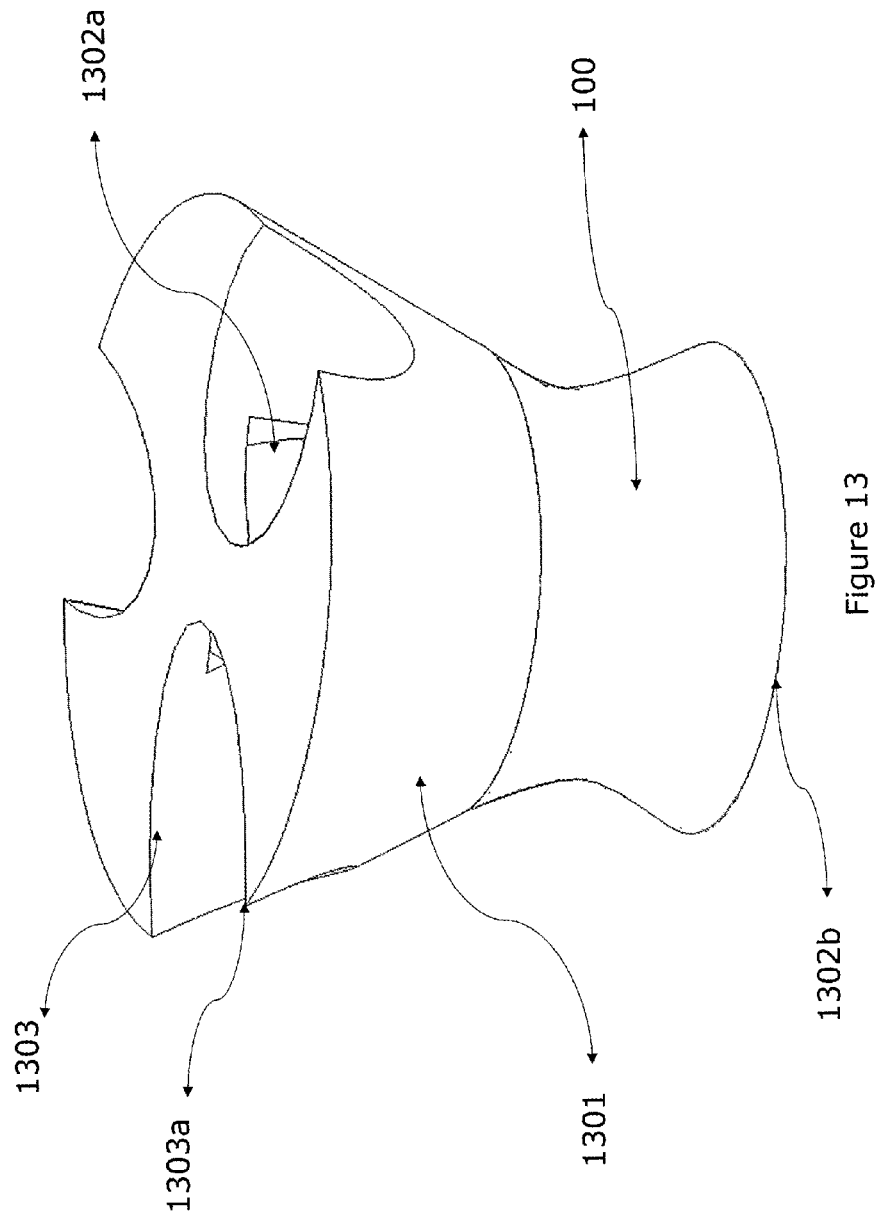
FIG. 13 illustrates an adapter of an electrode assembly in combination with another accessory element.

FIG. 13 illustrates an adapter 1300 of an electrode assembly according to the present invention. The adapter 1300 comprises two different bodies: a lower body 100 and an upper body 1301. An inner surface 1302 defines a first compartment 1302a for positioning three different electrodes of the electrode assembly, and a second compartment 1302b for receiving a conductive gel of the electrode assembly. The compartments 1302a, 1302b are in fluid communication with one another, thereby permitting the conductive gel provided in the second compartment 1302b to enter the first compartment 1302a for the purpose of coming into physical contact with the electrode.

The first compartment 1302a further comprises three slots 1303 each including a land surface 1303a for carrying a bottom surface of the electrode. Electrodes can be mounted from the top of the accessory 1300 into each of three slots 1303.

FIGS. 14(a) and 14(b) illustrate an adapter 1400 of an electrode assembly according to the present invention. The adapter 1400 comprises an adapter 100 in which compartment 102b is prefilled with the conductive gel 1403 and covered with a removable plastic shield 1401 on the bottom surface of 100. The compartment 102a of adapter 100 is preloaded with an electrode 1404 and covered with a tightening holder cap 110 on the top portion of compartment 102a.

Figure 15:
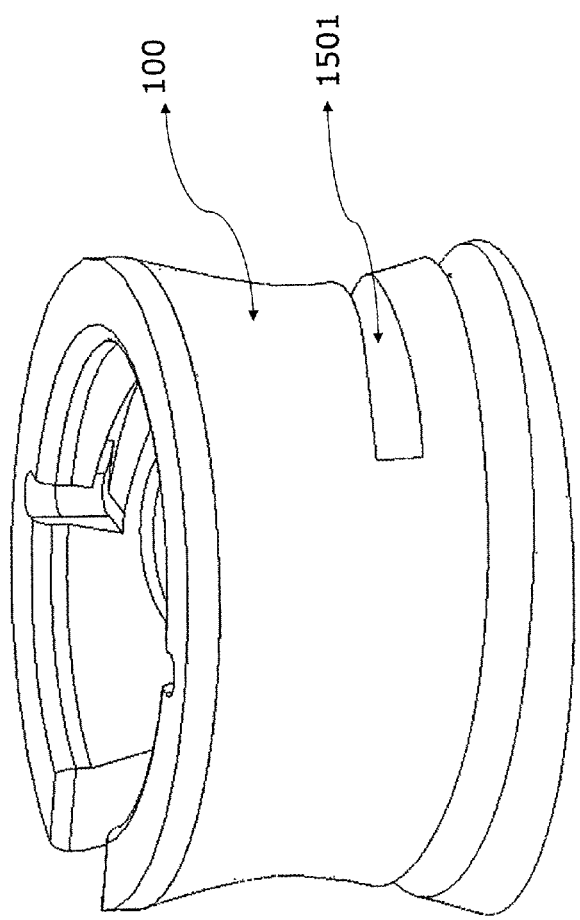
FIG. 15 illustrates another adapter of an electrode assembly in accordance with principles of the present invention.

FIG. 15 illustrates an adapter 1500 of an electrode assembly according to the present invention. The adapter 1500 comprises an adapter 100 in which outer surface 101 has a spiral groove 1501. The groove 1501 is designed to attach the adapter 100 within an associated aperture in a mounting apparatus be rotating the adapter 1500 clockwise or anti-clockwise within the aperture.

Figure 16B:
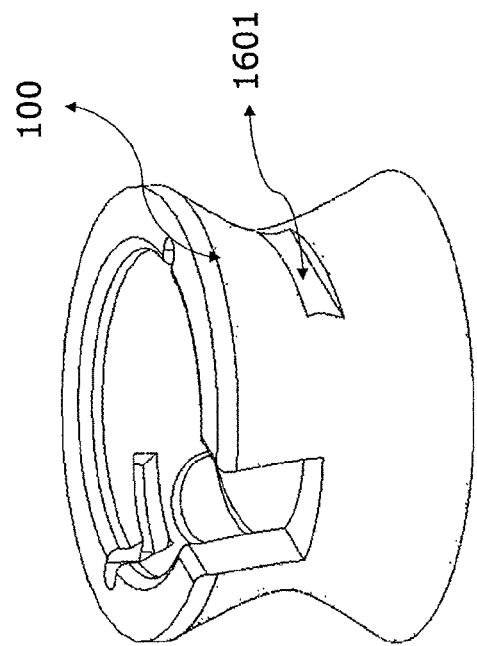
FIGS. 16(a) and 16(b) illustrate another adapter of an electrode assembly in accordance with principles of the present invention.
Figure 16A:
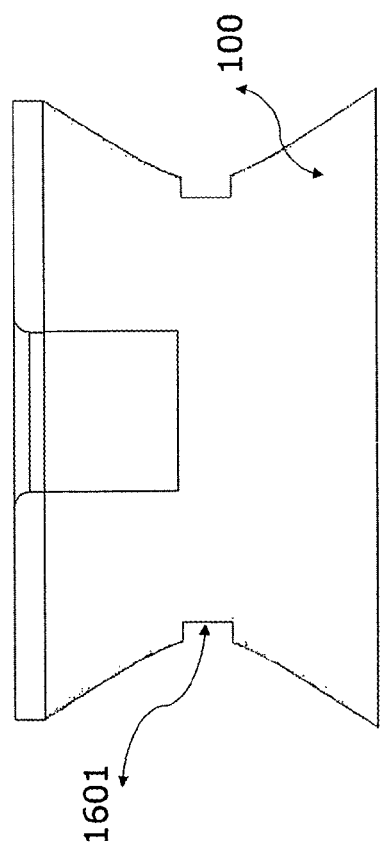

FIGS. 16(a) and 16(b) illustrate an adapter 1600 of an electrode assembly according to the present invention. The adapter 1600 comprises an adapter 100 in which outer surface 101 comprises two grooves 1601 on each side of the surface 101 for sliding into an associated aperture in a mounting apparatus.

Figure 17:
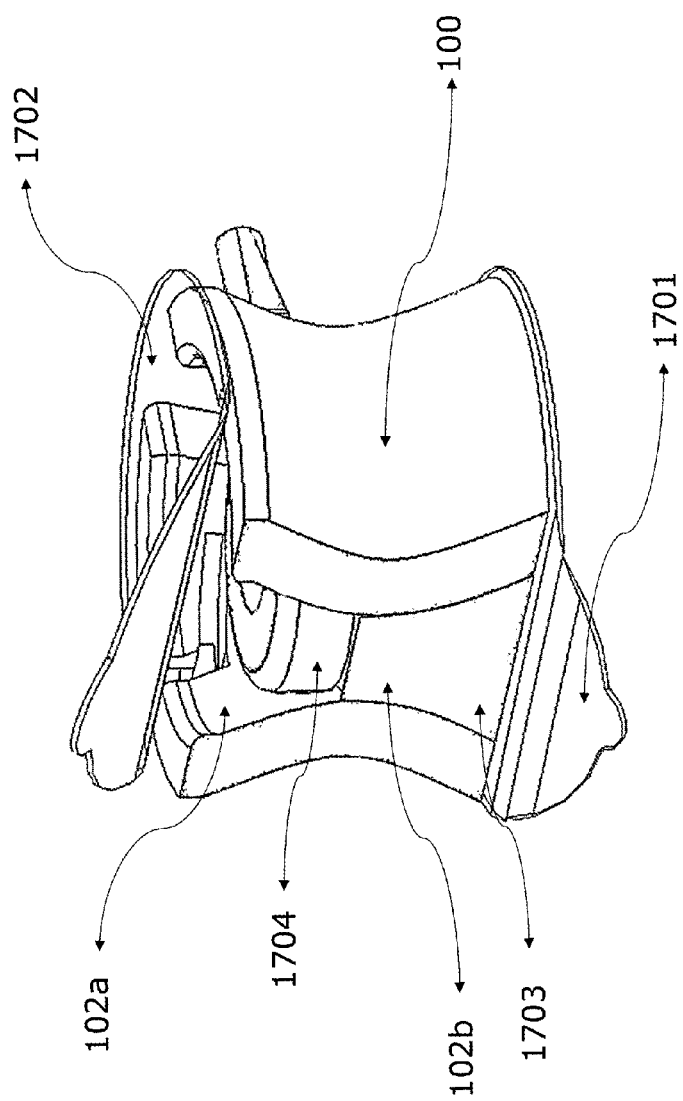
FIG. 17 illustrates the adapter of FIG. 14 without the cap and with an additional shield.

FIG. 17 illustrates an adapter 1700 of an electrode assembly according to the present invention. The adapter 1700 comprises an adapter 100 in which compartment 102b is prefilled with the conductive gel 1703 and covered with a removable plastic shield 1701 on the bottom surface of 100. The compartment 102a of adapter 100 is in addition preloaded with the electrode 1704 and covered with a removable plastic shield 1702 on the top portion of compartment 102a.

Figure 18:
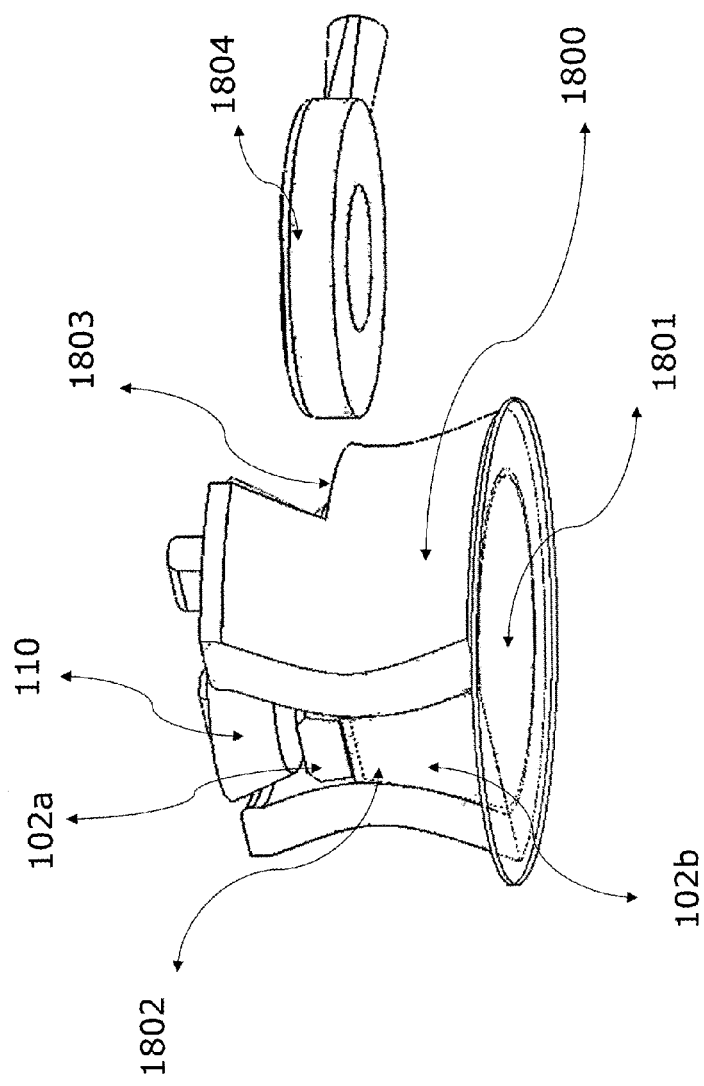
FIG. 18 illustrates the adapter of FIG. 14 with an additional shield.

FIG. 18 illustrates an adapter 1800 of an electrode assembly according to the present invention. The adapter 1800 comprises an adapter 100 in which compartment 102b is prefilled with the conductive gel 1802 and covered with a removable plastic shield 1801 on the bottom surface of 100. The compartment 102a of adapter 100 is covered with a tightening holder cap 110 and the side surface 101 of adapter body 100 is also covered with a removable plastic shield 1803 from where the electrode 1804 can be slid into the holder 100 from the side.

It may be practical for certain adapters to be added for additional functionality. For instance, large electrodes can suffer from gel or salt solution leaking outside of the electrode area, or from drying during stimulation. This partly results from the fact that large electrodes must be flexible. Therefore, specific adapters may be added to the electrode holder for containment of the components or to fix the position of the components.

In one embodiment, a firm plastic inset, placed firmly against the scalp, prevents this leakage. In another embodiment, an adapter is made which is a cap to be placed on top of the plastic holder. In a preferred embodiment, the adapter locks in place by fitting with tabs on the two components. In a particularly preferred embodiment, the tabs are on the adapter, and the electrode holder is engineered with grooves on its inner surface in order to lock the adapter in place. In an alternate embodiment, the tabs are located on the outer surface of the electrode holder, and the grooves are located in the adapter.

In order to fit the given electrode holder in the gel volume and hold it in place, various methods have been engineered into the holder to practical access and control over electrode position. In one embodiment, the electrode is pushed from the top of the holder into a set of ridges at a defined distance. In another embodiment, the electrode adapter has a side opening at the level of the ridges, and the electrode may be slid into place from the side.

In order to affix the electrode holder to the body, cranium, or scalp, a head-gear may be used as discussed below. To attach the electrode holder to the head-gear the electrode holder may be modified to allow secure attachment to the head-gear. This includes the use of lock mechanisms, snap mechanisms, and screw mechanisms. In addition, the hardware for securing the electrode holder to the head-gear may be designed such that when the electrode holder is secured it is modified or functionally activated to allow stimulation. In one embodiment, gel is sealed in the electrode holder and a seal is punctured when the electrode holder is attached to the head-gear.

As mentioned above, the size of the optimal electrode holder depends on the ranges of values that are optimal for gel-scalp contact area and the distance between the electrode and the skin. In one embodiment, the gel-scalp contact area is less than 7 $cm^2$ and greater than 0.07 $cm^2$. In a preferred embodiment, the area is less than 3 $cm^2$ and greater than 1 $cm^2$. The dimensions of the orifice at the bottom of the electrode holder follow logically from the above dimensions, and are constructed as exposing the same area as the gel-scalp contact surface area.

The safety objectives of the invention additionally necessitate that the holder be built high enough (i.e. in a large enough distance along the axis normal to the scalp) that it allows an optimal distance between the electrode and the skin. In one embodiment, the distance between the electrode and the skin is between 0.25 cm and 1.3 cm. In a preferred embodiment, the distance is between 0.5 cm and 0.8 cm.

Therefore, the total volume of the optimal holder is determined by the ideal area of the gel-skin contact orifice, the distance (height) needed to accommodate the ideal distance between the electrode and the skin, and the inner contour and shape of the holder. The dimensions of the inner holder should be such that they can also accommodate a suitable volume of the gel to be used during stimulation. In one embodiment, the volume of the gel is between 0.1 ml and 10 ml. In a preferred embodiment, the volume of the gel is between 0.5 mL and 5 mL, and preferably between 0.5 mL and 1.5 mL.

As noted above we discovered that small electrodes can pass significant currents with minimal voltage and sensation. However, the electrodes must also be bigger than a minimum size for both pain and voltage considerations. In moving from a smaller to larger electrode design, we observed dramatic improvements in the voltage capacity of the electrodes, and the increase in voltage capacity was not related to the gel-skin contact area but rather the metal-gel contact area. Therefore, methods to increase the metal-gel interface area have been employed in the electrode assemblies of the invention.

In one embodiment, the properties of the metal electrode are specifically considered. The electrode can be a ring, disk, pellet, or other shape. In a preferred embodiment, the electrode is a ring, designed to have the optimal surface area for taking up a defined space in the electrode holder. Along these lines, one can envision a more convoluted permutation of the electrode to increase electrode-to-gel surface area contact, thereby making use of the insights of this invention. In one embodiment, the metal-gel contact area is greater than 50% of the gel-skin contact area. In another embodiment, the metal-gel contact area is greater than 100% of the gel-skin contact area. In a preferred embodiment, the metal-gel contact area is increased relative to the gel-skin contact area by increasing the exposed vertical projection of the metal in the gel.

In one preferred embodiment, the increased vertical projection takes the form of the pellet electrode design. In another preferred embodiment, the maximal vertical dimension of the metal is greater than 3 times the horizontal diameter. In another preferred embodiment, the maximum electrode vertical dimension is less than the maximum horizontal dimension.

In another preferred embodiment, the electrode metal gel contact area includes the top and bottom of said metal electrode thereby approximately doubling the contact area between the metal and gel (compared to a metal electrode sitting on top of a gel). In another embodiment, the surface of the metal electrode is convoluted to increase the metal-gel contact area including the use of ridges, spikes, roughening, and curves. In a still preferred embodiment, the metal-gel contact area is increased through the process of sintering. In a still preferred embodiment, AgCl is used in the sintering process.

In another preferred embodiment, the center of the electrode is hollow to increase gel-metal contact area. Such an embodiment is also described here as the ring electrode. In another preferred embodiment, the hollow electrode is built into the wall of the electrode holder.

In another embodiment, the electrode holder is constructed such that it allows maximal electrode surface area exposed to the gel by allowing multiple electrodes. In one preferred embodiment, the adaptor has an extra accessory "sleeve" that allows for two electrodes to be used concurrently in the same holder, doubling surface area exposure. In another preferred embodiment, an adapter is constructed with three openings to allow three separate electrodes to fully contact the gel in a single holder, thus increasing surface area exposure three-fold.

FIGS. 19(a)-21 depict several exemplary electrodes according to the present invention.

Figure 19B:
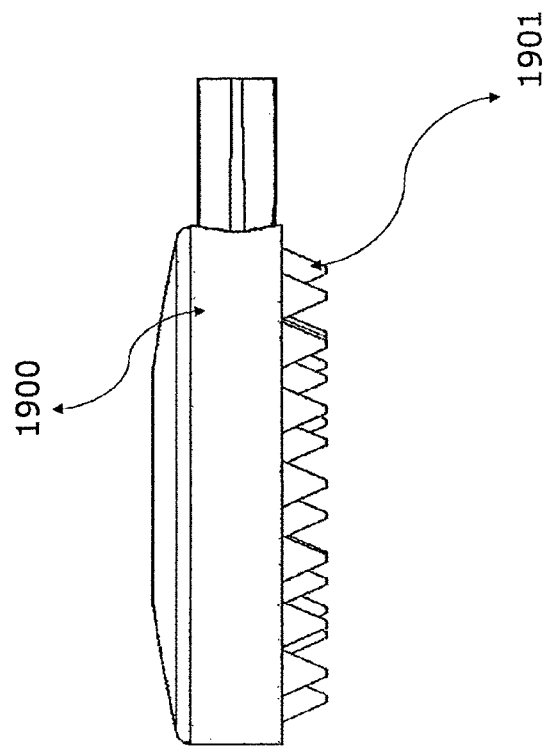
FIGS. 19(a) and 19(b) illustrate an electrode according to the present invention.
Figure 19A:
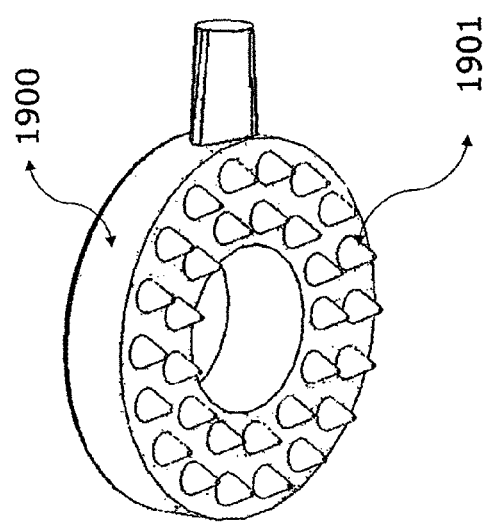

FIGS. 19(a) and 19(b) illustrates an electrode 1900 according to the present invention. The electrode 1900 comprises triangular spikes 1901 on the bottom surface to increase the metal surface area in contact with the gel.

Figure 20:
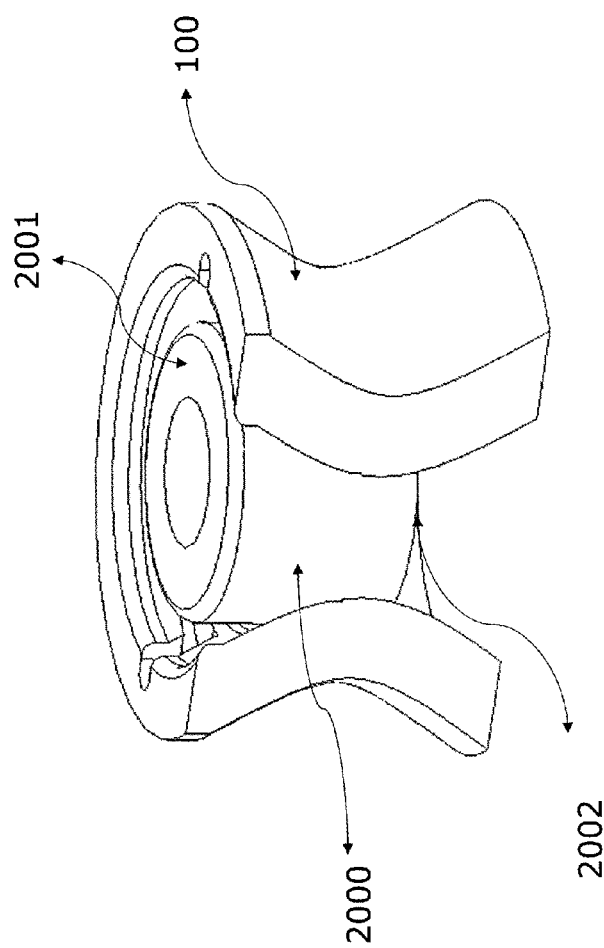
FIG. 20 illustrates an electrode according to the present invention.

FIG. 20 illustrates an electrode 2000 with its height increased for example by a factor of 3 to increase the gel to metal contact surface area. Electrode 2000 is mounted in the electrode adapter 100. Electrode 2000 has the same top 2001 and bottom 2002 surface area.

Figure 21:
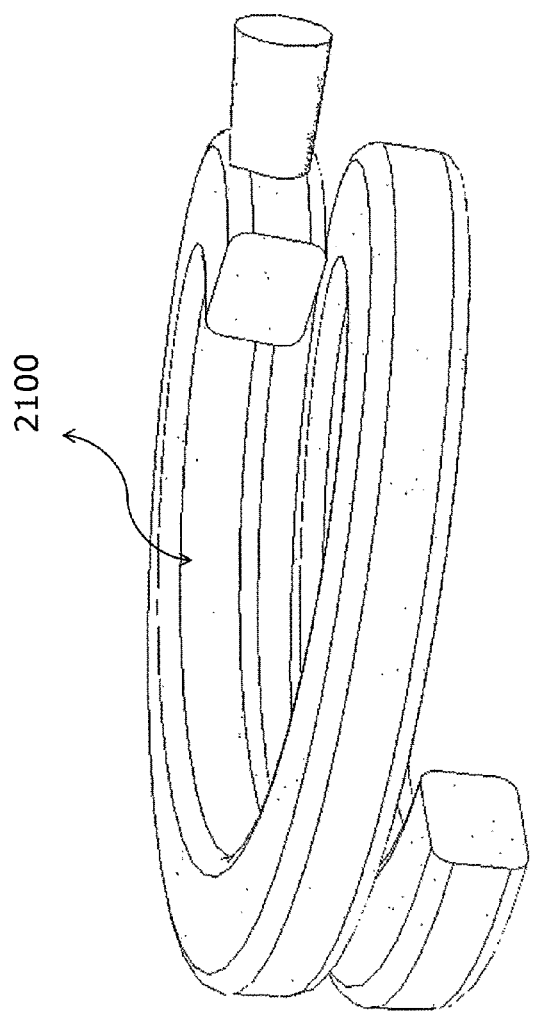
FIG. 21 illustrates an electrode according to the present invention.

FIG. 21 illustrates an electrode 2100 designed in a spiral shape to increase the overall surface area in contact with the gel. The electrode 2100 is configured to be immersed completely into the gel compartment 102b.

The designs described above imply a single compartment for the gel and subsequently immersed electrode. However, it may be desirable to have multiple gels, for conductance purposes or for more complex management of pH, temperature, or potential build-up. As such, another embodiment of the invention entails a holder reservoir that has multiple compartments which may contain different gels.

It is appreciated that different electrode materials can have different physicochemical effects during stimulation, and therefore some may be more desirable than others for both minimizing voltage build-up and pain sensation. Therefore, the solid conductor of the electrode may be metal, rubber, conductive rubber, Ag/AgCl, Ag, Gold.

In a preferred embodiment the solid-conductor is sintered Ag/AgCl.

Thus, in a particularly preferred embodiment, the electrode assembly of the invention includes a cylindrical, semi-rigid plastic electrode holder that exposes roughly 2 $cm^2$ of surface area to the scalp, combined with a sintered AgCl ring electrode that is inserted by guided ridges roughly 0.5 cm above the scalp orifice into the side of the electrode holder, and fully submerged in 1 ml gel of the preferred composition discussed in a later aspect below.

To obtain reliable stimulation, and thus a consistent safety profile during neurocranial stimulation, the connection between the electrode and the scalp should be sufficiently secure such that the electrode gel maintains contact with the metal electrode and with the scalp. The former is achieved by a plastic holder, as discussed in detail above. The latter requires a connection of the electrode assembly, or preferably multiple electrode assemblies, to the head. The most practical method for this use is a type of "head gear" to hold the plastic assemblies in place on the scalp. The technology to hold the plastic inset to the head is thus critical and as discussed herein may be optimized for the most practical use.

In some measurement devices such as EEG, a flexible cap, with fixed position holes, is used to position an array of electrodes in fixed positions of the head. In fact, with such measurement, the use of pre-defined fixed positions across subjects is preferred. In contrast, while one could envision the use of pre-set (EEG) positions for stimulation, it is preferred for both stimulation efficacy and safety to have the ability to place the electrodes in various specific positions on the scalp, depending on the specific stimulation application. This is necessary to ensure specific targeting of brain regions, as well as to account for variations in head size and contour between individuals. The head (mounting) gear described here is designed to fit with the plastic holders described in this invention, although is applicable to electrodes and holders not described herein.

In one embodiment, multiple electrode assemblies are attached by a flexible band that wraps either from front-to-back or side-to-side across the head. This band contains both individual spaces for electrode assemblies, as well as slots for connection of sub-bands to splay across the rest of the head, each with their own places for electrode assemblies at fixed distances along the band.

In a preferred embodiment, the main band is wrapped completely around the head and connected with a clasp.

Figure 26:
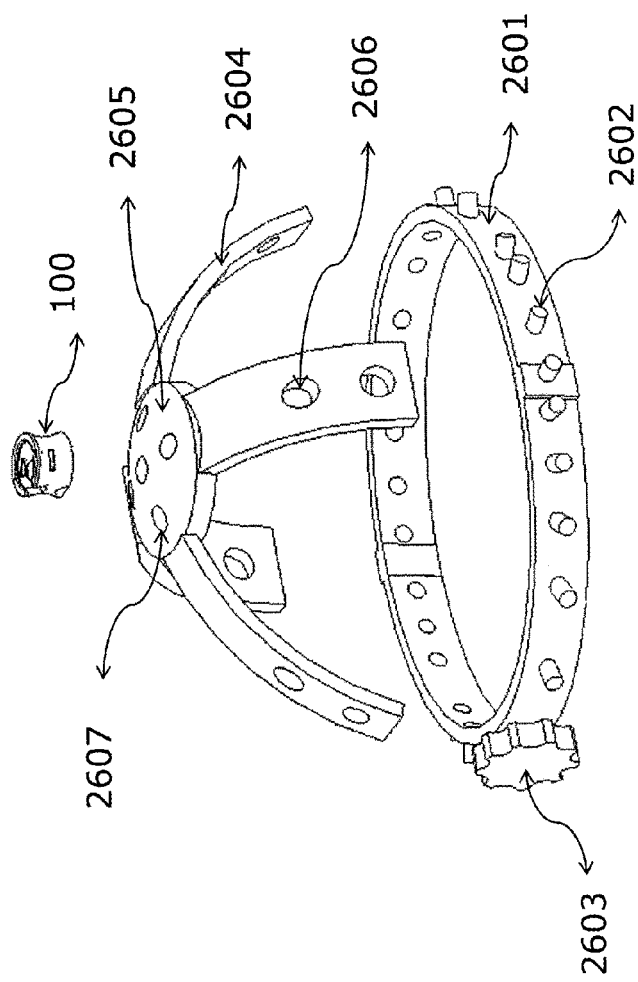
FIG. 26 illustrates a circular band design for an electrode assembly mounting apparatus according to the present invention.

FIG. 26 depicts an exemplary circular band design for an electrode assembly mounting apparatus according to the present invention.

A head gear 2600 includes an adjustable plastic head band 2601 and fabric C shaped cross band 2604 which also include a circular fabric disc shaped area 2605 on the inter-section of 2604 bands. A circular knob 2603 is preferably provided to increase or decrease the length of head band. All around the length of the head band 2601 there are protrusions 2602 to hold the cross bands 2604 in proper position. Cross band 2604 includes holes 2606 on a marginal end of each band that fit with the protrusions 2602 of the head band 2601. A disc shaped section 2605 has holes 2607 to accommodate electrode adapters (for example, adapters 100, 800, 1300, 1400, 1500, 1700 or 500 as previously described). The cross bands 2604 can be adjusted along different protrusions 2602 of the head band 2601 to accurately position the disc shaped area 2605 on head.

Figure 23:
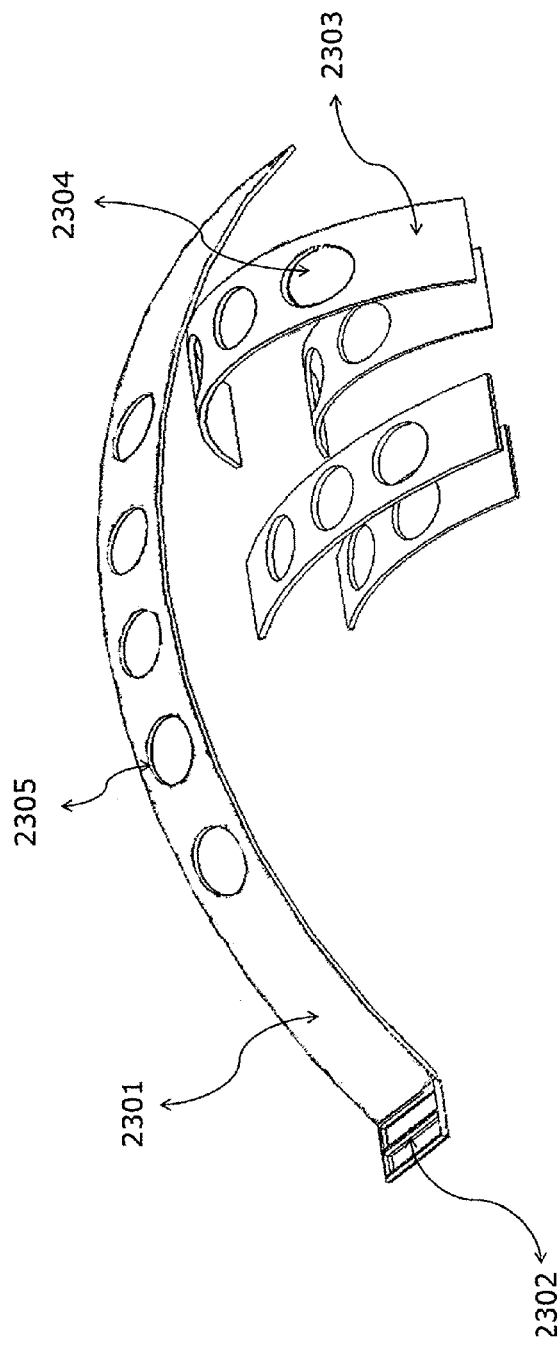
FIGS. 23 and 24 illustrate semi-circular band for electrode assembly mounting apparatus according to the present invention.
Figure 24:
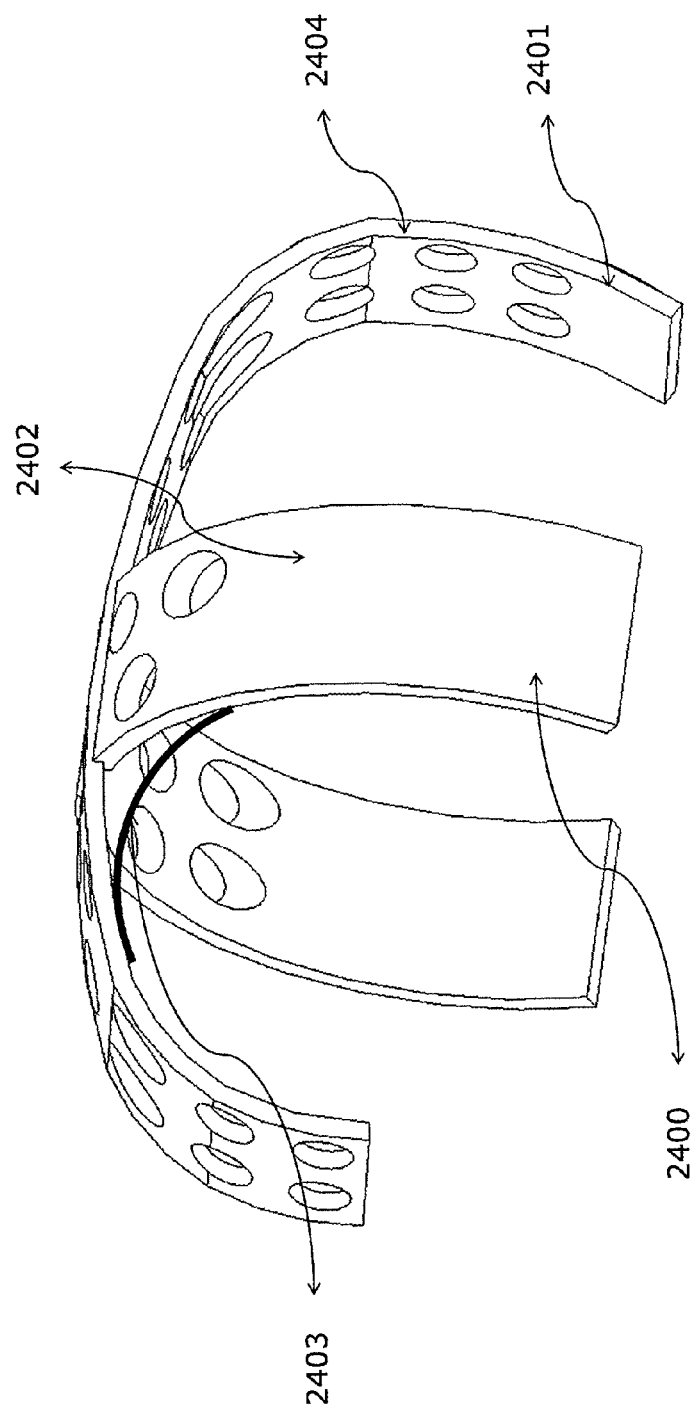

In another preferred embodiment, the band is in a semicircle shape, fixed on the head by bands diverging from the central main band FIGS. 23 and 24 depict exemplary semi-circular band designs for electrode assembly mounting apparatus according to the present invention.

For example, FIG. 23 illustrates a flexible head band 2301 with the webbing buckle 2302 on one end, to adjust the length of the band on the head. Various sub-band attachments 2303 may preferably be attached on to the holes 2305 of the band 2301 for modular positioning of the electrode adapters (for example, adapters 100, 800, 1300, 1400, 1500, 1700 or 500 as previously described). The adapters may be mounted on to different holes 2305 of the head band or of sub-bands 2304.

FIG. 24 illustrates a plastic "double C configuration" cross band 2400. An extra flexible band 2403 may be attached between two main bands of the cross band 2400. The cross band 2400 has numerous holes 2404 all along the surface for mounting of different kinds of electrode adapters (for example, adapters 100, 800, 1300, 1400, 1500, 1700 or 500 as previously described). Electrodes may effectively be positioned anywhere on the head using different holes 2404 on cross band 2400.

In another preferred embodiment, two main bands form a "cross" on top of the head, the ends of each movable arm of the cross containing movable electrode holders.

Figure 25:
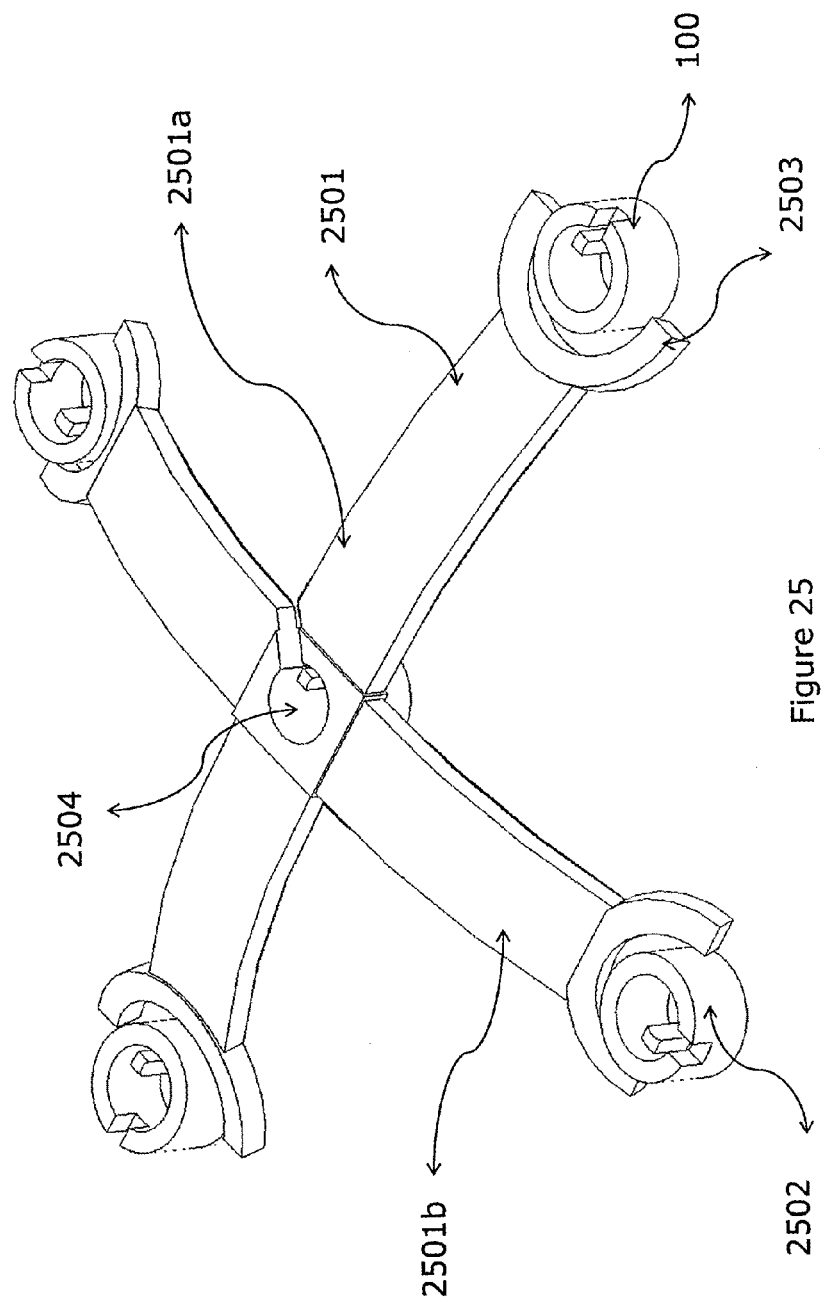
FIG. 25 illustrates a cross band design for an electrode assembly mounting apparatus according to the present invention.

FIG. 25 depicts an exemplary cross band design for a head-fixing means according to the present invention. A plastic cross band 2501 comprises two plastic arms 2501a and 2501b crossing each other at the center. Two arms 2501a and 2501b can be moved along the center. A center portion of the two arms 2501a and 2501b provides a receptacle 2504 to attach an additional electrode adapter (for example, adapters 100, 800, 1300, 1400, 1500, 1700 or 500 as previously described).

At the marginal end of each arm 2501a and 2501b there are movable C shaped plastic holders 2503 to hold another plastic attachment 2502. Electrode adapters (for example, adapters 100, 800, 1300, 1400, 1500, 1700 or 500 as previously described) may be mounted on the plastic attachment 2502.

In another embodiment, the head-fixing means entails a "mounting plate" design, which contains two bands to hold the unit in place, and 2 or more plates, each with specific flexible or predefined spaces for electrode assemblies, diverging from the main bands. The plates are connected to each other by hinges, therefore allowing for adjustment of individual plates to accommodate head size and contour to allow precise positioning. In a particularly preferred embodiment, there are three plates connected to the central bands.

Figure 22:
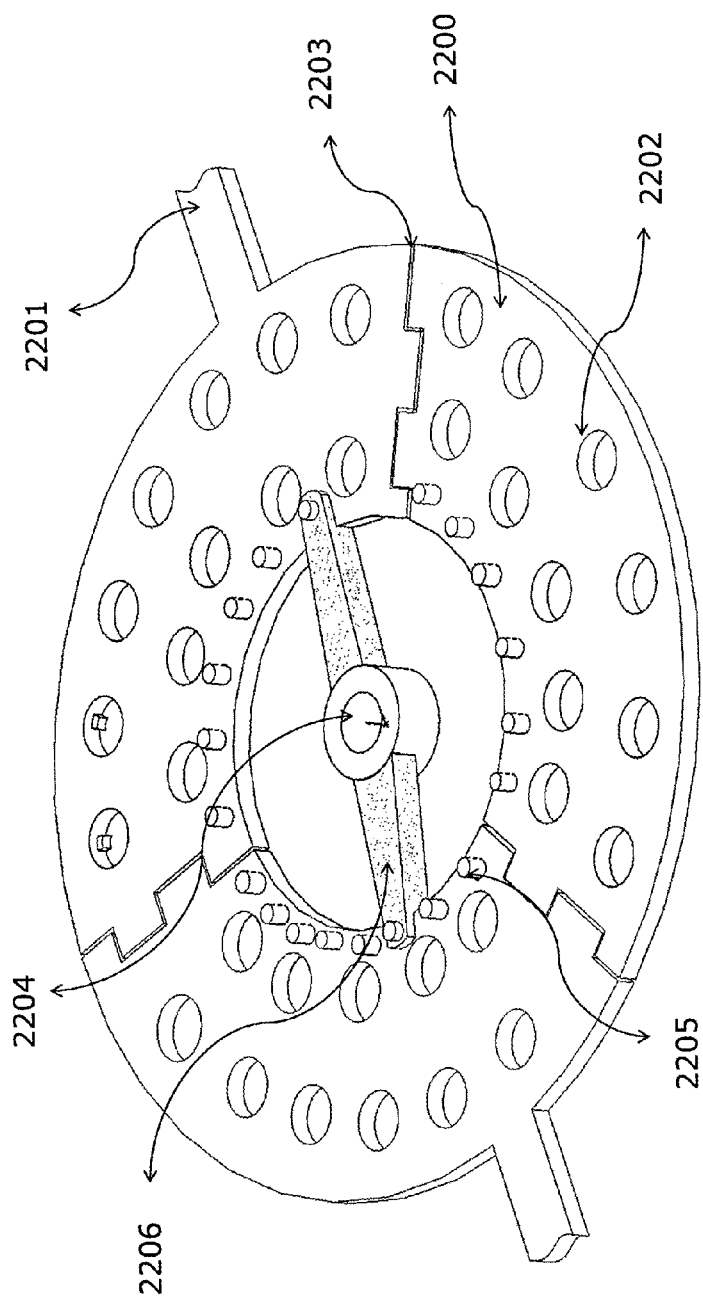
FIG. 22 illustrates a mounting plate for an electrode assembly mounting apparatus according to the present invention.

FIG. 22 depicts an exemplary mounting plate design for an electrode assembly mounting apparatus according to the present invention For example, FIG. 22 illustrates a circular plastic plate 2200 with numerous holes 2202 for modular positioning of the electrodes. The electrode plate is preferably made of three or more different parts attached to each other by hinge joints 2203, which allow a free movement of different plates 2200. Flexible band 2201 is also attached with the plate for holding of the plate across the head. The plate has an orifice at the center 2207 to attach a small flexible band 2206. The small flexible band has holes on the marginal end to attach with the tabs 2205 along the internal margin of the orifice 2207 of the plate 2200.

Figure 28:
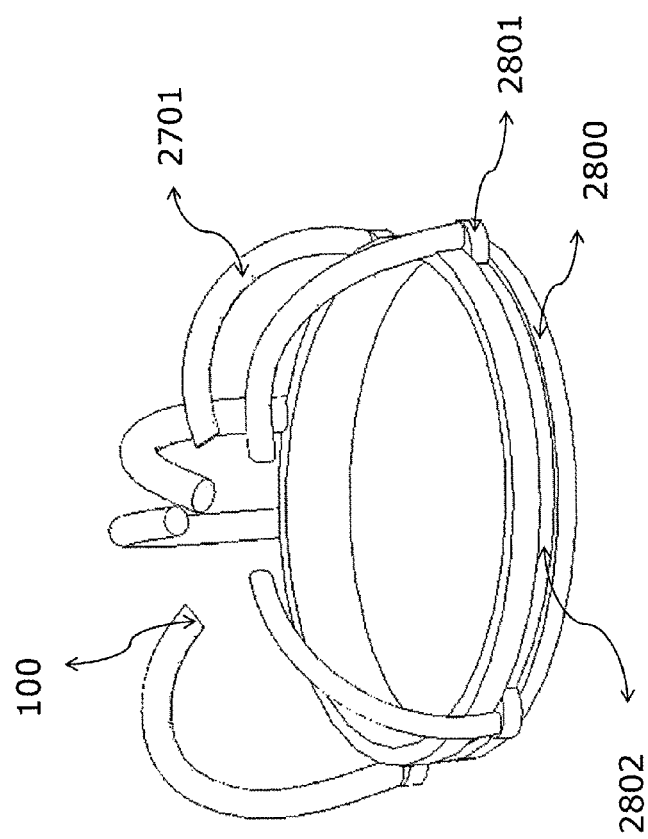

FIGS. 27(a)-28 depict variants of the semi-circular and circular band designs, respectively, in which the sub bands are replaced by flexible arms that are each attached to the semi-circular or circular band at a proximal end, receive an electrode assembly at a distal end and may be manipulated to flexibly position the electrode assemblies on the cranial skin surface of a user.

FIGS. 27(a) and 27(b) illustrate a plastic semicircular head band 2700 with 5 flexible and movable arms 2701 radiating from the upper surface 2700a of the head band 2700. Each of the arms has a C shaped plastic cup 2702, which holds another plastic piece 2703. Each plastic piece 2703 holds an electrode adapter (for example, any of the adapters 100, 800, 1300, 1400, 1500, 1700 or 500 previously described). By moving different arms 2701 electrodes can be positioned on any location of the head.

FIG. 28 illustrates a circular adjustable plastic head band 2800 with a groove 2802 all along the length of the head band 2800. Small plastic slider 2801 tabs protrude from the groove 2802 and can be manipulated to slide protruding flexible arms within the groove 2802. Each of the arms preferably have a C shaped plastic cup 2702, that holds another plastic piece 2703. Each plastic piece 2703 holds an electrode adapter (for example, any of the electrode adapters 100, 800, 1300, 1400, 1500, 1700 or 500 previously described). By moving different arms 2701 within the groove 2802, the electrodes can be positioned on any location of the head.

In another embodiment, a flexible EEG cap is modified to allow arbitrary electrode positioning. In a preferred embodiment, a sub-band is placed at specific points on a flexible EEG cap.

In yet another embodiment, the electrode is attached to the scalp using a tape, glue, a clip or a ridge.

We describe head-gear formed of bands and apertured regions, suitable for positioning of electrode assemblies for neuro-cranial electrodes. It is possible to use the described method for Neurocranial stimulation with other techniques for brain stimulation known to those in the art, while making necessary modifications to the Neurocranial system or the other stimulation techniques as necessary. Other such brain stimulation techniques include Transcranial Magnetic Stimulation, Transcranial Direct Current Stimulation, Deep Brain Stimulation, Vagus Nerve Stimulation, Epicranial Stimulation, Transcutaneous Electrical Stimulation, and Transcranial Electrical Stimulation. In a separate embodiment, one may also actively combine Neurocranial stimulation with stimulation with electrodes positioned on the cranium or elsewhere on the body, such as extra-cephalic electrodes. In one particular embodiment, a power source is connected to one Neurocranial electrode and other electrode on the body. The additional electrode on the body may take on a range of forms known to those in the art or may adopt the technologies developed for Neurocranial stimulation.

According to a second aspect of the invention, there is provided a method to reduce irritation, sensation, discomfort, injury, burns, perception, inflammation, pain, or redness during neurocranial stimulation comprising using with a neurocranial stimulation device an electrode apparatus detailed in the present invention. The invention is related to any neurocranial stimulation technique, although the invention is also especially useful for transcranial stimulation, and in a particular application is transcranial direct current stimulation. In ideal embodiments, the method comprises using the electrode apparatus described above, including a selected electrode, electrode holder with a gel and containment adapter as described in the invention, and a specific means of attachment of the head as described above.

According to a third aspect of the invention, there are provided compositions for neurocranial stimulation gels that reduce or prevent irritation, sensation, discomfort, injury, burns, perception, inflammation, pain, or redness.

Gels have been used with cranial electrodes in the past, however they have been mainly in monitoring applications such as EEG, or for general low-current stimulation. These types of gels were not designed for the high currents and application times necessary for effective neurocranial stimulation (e.g. up to 2 mA for greater than 20 minutes), and it is generally thought that these gels would not be sufficient to protect the patient from pain or discomfort. However, we unexpectedly observed that gels are able to allow these high currents and long times of stimulation with minimal discomfort. In this invention are provide specific compositions which we found were effective to allow for delivery of the desired current to the scalp with minimal pain or discomfort.

Additionally, while it was has logically been expected that physical changes of the electrode and gel (such as changes in potential, pH, and temperature during electrical stimulation) could be a predictor of pain and sensitivity in the subject undergoing the stimulation, we have discovered that, unexpectedly, pain can be experienced by the subject even in the absence of a pH or temperature change in the gel during stimulation. And limiting the increase in electrode voltage can reduce pH and temperature changes—but does not necessarily preclude pain. For instance, Lectron II gel seems to have the broadest protection against electrode potential buildup and pH change, but leads to greater pain sensation than our CCNY-4 gel. Therefore, properties other than pH and temperature must be considered for a safe and effective gel for the neurocranial applications of this invention.

We have found that the optimal gel to allow for efficient delivery of current while maintaining good protection against pain or discomfort during neurocranial stimulation has certain core components, including: 1) A polymer, which functions includes support properties; 2) surfactants or surface acting agent, functioning to act on the skin to increasing permeability and/or change skin resistivity; 3) humectants, functioning to maintain gel hydration; 4) salts, functioning to increase electrical conductivity; 5) water; and 6) preservatives or other chemicals. These are the general components of a suitable gel, and is understood that the performance of the gel relates to its total properties after fabrication. Each of these components as ingredients may serve the function of another component, for example a surfactant with salt content, or a polymer with hydration properties. As another example, salt may be omitted if conductivity is provided by another substance such as the polymer or surfactant. As such, this list can be interpreted either as key ingredients or as a list of core functions that should be achieved.

However, although examples of formulations with these properties can be found in regards to medical electrodes, we have unexpectedly found that specific formulations are particularly suitable and appropriate for our applications. FIG. 37 shows a sample of gels tested; their general composition features and other physical properties are noted. While these gels all have similar features and can be used with metal electrodes, only the CCNY gels were able to show a minimal pain response for each electrode used (also see FIGS. 34 and 35 of this patent). We have found that common electrode gels can be used as a foundation for the gel, but are not sufficient to prevent pain or discomfort during neurocranial stimulation with high current. Therefore, gels known in the art as conducting gels for electrode applications, such as Signa gel, Spectra 360, Tensive, Redux, 1090 BioGel, and Lectron are suitable as a foundation or base composition for a gel, but require additional specific added components, detailed here, in order to function effectively with minimal pain or discomfort.

| Gel | Composition | Preservative | Viscosity | pH | Manufacturer Electrical Conductivity | Measured Conductivity (see text for additional measurements on thermal conductivity) |
|---|---|---|---|---|---|---|
| CCNY5s2 | Polymer Humectants Reverse Osmosis water Surface active agent Sodium chloride (0.5% Saline Base plus NaCl supplement) Local Anesthetic (Lidocaine/Prilocaine) | Propylparaben and methylparaben in bacteriostatic Concentration | 180,000 TO 260,000 CPS | 5.4-6.4 | | More than 30,200 μmhos/cm |
| CCNY5s1 | Polymer Humectants Reverse Osmosis water Surface active agent Color Sodium chloride | Propylparaben and methylparaben in bacteriostatic Concentration | 180,000 TO 260,000 CPS | 5.4-6.4 | | More than 30,200 μmhos/cm |

-continued

| Gel | Composition | Preservative | Viscosity | pH | Manufacturer Electrical Conductivity | Measured Conductivity (see text for additional measurements on thermal conductivity) |
|---|---|---|---|---|---|---|
| CCNY4 | (0.5% Saline Base plus NaCl supplement) Local Anesthetic (Lanacane) Polymer Humectants Reverse Osmosis water Surface active agent Color Sodium chloride | Propylparaben and methylparaben in bacteriostatic Concentration | 180,000 TO 260,000 CPS | 5.4-6.4 | | More than 30,200 μmhos/cm |
| SIGNAGEL | (0.5% Saline Base plus NaCl supplement) Polymer Humectants Reverse Osmosis water Surface active agent Color Sodium chloride | Propylparaben and methylparaben in bacteriostatic Concentration | 180,000 TO 260,000 CPS | 5.4-6.4 | More than 40,000 μmhos/cm | 30,200 μmhos/cm |
| REDUX | (0.5% Saline Base) Polymer Humectants Reverse osmosis water Quartz Sodium chloride Preservative | Chloroxylenol | 70,000 TO 160,000 CPS | 5.5-6.5 | More than 40,000 μmhos/cm | 18,900 μmhos/cm |
| SPECTRA 360 | Polymer Humectants Reverse osmosis water Preservatives Color | Propyl paraben and Methyl paraben in Bacteriostatic concentration | 175,000 to 260,000 CPS | 6.3-7.0 | Much lower than Redux gel | 1700-1800 μmhos/cm |
| TENSIVE | Polymer Humectants Reverse osmosis water Sodium chloride Preservative Perfume | Propyl paraben and Methyl paraben | 175,000 to 325,000 CPS | 4.5-7.5 | More than 6000 μmhos/cm | 6,300 μmhos/cm |
| LECTRON | Water Humectant Sodium hydroxide Potassium hydroxide Carboxy Polymethylene Hydroxy Ethyl Cellulose Color | Propylene Glycol | 1,250,000 + or − 190,000 CPS | 6-7.5 | Resistance 14 +− 2 OHM Density 1.060 g/mL | 15,140 μmhos/cm |
| ELECTRODE GEL | Water Sodium Chloride Tragacanth Potassium Bitartrate (Cream of Tartar) Glycerin | Propyl paraben and Methyl paraben | | | | 13,720 μmhos/cm |

One special consideration includes the presence of electrical current driven through the system which may alter the properties of the gel in a desirable or undesirable manner. An example of an undesirable change is our discovery of the formation on an encapsulation layer around the electrode during DC stimulation. Another special consideration also includes how the electric current affects the actions and delivery of gel components in a desirable or undesirable fashion. Still another undesirable example includes electrical delivery of toxic substances. On the contrary, a desirable example might include the specific delivery of analgesic substances. Yet another special consideration is synergistic or antagonistic actions of the electricity and gel components on the skin. A synergistic example includes decreased skin resistance by the surfactant and the electrical stimulation. Further examples and illustrations are presented in the embodiments. Based on these findings, it is thus evident that a medical electrode gel must be especially designed for our application. Each of the specific types of ingredients or functions must be optimized.

Gels may use humectants to maintain gel hydration. Humectants include materials such as propylene glycol, and can be formulated with or without ethanol. Propylene glycol may also serve as a preservative. Propylene glycol may result in skin redness and its concentration should be regulated. In one embodiment, propylene glycol is included at a concentration of 1 µM to 10 mM. In a preferred embodiment, propylene glycol is included at a concentration of 1 µM to 1 mM. In a still preferred embodiment, propylene glycol is included at a concentration of 1 µM to 50 µM.

Oil solubilizing surfactants including ionic and non-ionic surfactants may be included in the gel. Agents that solubilize the oil layer on the skin and or penetrate the skin may be used. They may be particularly useful in lowering skin resistance. Examples include sodium hexametaphosphate, trisodium phosphate, and products such as TWEEN and SPAN made by Atlas Chemicals. In one embodiment, the gel contains 0.5 to 5% sodium hexametaphosphate. In a preferred embodiment, a 1% composition of sodium hexametaphosphate in the gel is preferred.

Appropriate gel viscosity must be adjusted relative the specialized plastic holder. The polymer may be formulated using various techniques familiar to those skilled in the art but must be designed to allow current passage. In a particular embodiment, hydroxycellulose may be used at the polymer or polymer agent.

The polymer that is used may be dissolved in a base liquid. Suitable liquids include water, alcohol, acetone, dimethlysulfoxide (DMSO), dimethyl formide (DMF), or a polar solvent. Water, alcohol, and mixtures thereof are preferred. Additional agents, such as cross-linking agents, may be added to adjust gel properties including viscosity. The polymer may be set or cross-linked via photons, thermal treatment or chemical treatment such as, but not limited to, deprotonation, oxidation or reduction. In one embodiment a viscosity of 10,000 to 1,000,000 CPS is used, and more preferably the viscosity is within 150,000 to 200,000 CPS. In another embodiment, the viscosity of the gel changes upon delivery due to dehydration, temperature changes, or skin contact. In a preferred embodiment, the viscosity increases from during a temperate change from approximately 25 degrees Celsius to 37 degrees Celsius. In another preferred embodiment, the viscosity decreases on contact with air, skin, or the holder surface. The changes in viscosity may be mediated or triggered by exposure to the air or to the skin as described in this invention. For example by using an adapter comprising a sealing member affixed to the positioning surface and extending over the orifice of the adaptor, this sealing member being configured to be peeled off or pierced. In one embodiment, the gel contains an alcohol. In another embodiment, the gel solidifies with an increase in temperature, in another with a decrease. In a separate embodiment, a solvent in the gel vaporize with lower pressure, leaving any solids behind, resulting in a change in viscosity. Additional ingredients may also be used to adjust viscosity or other relevant properties of the gel, for example "dilatants" where the viscosity increases with agitation. The resulting high viscosities will restrict the free movement of the seal. Thixotropic fluids which lower gel viscosity with agitation. Addition or presence of plastic fluids which change viscosity.

An electrolyte is key to the formulation of the gel. Here, the electrolyte is any material that will ionize in the liquid. The electrolyte may contain ions that are in the metal electrode or in biological tissue. Examples of suitable materials include ionizable salts, salts of acids or bases, or buffer solutions. Examples of inorganic salts include potassium chloride, sodium sulfate and organic acids or salts such as citric acid potassium citrate, or potassium acetate.

Previously, electrode designs were made to increase the resistivity of the electrode abutting the skin or tissue, since it was considered that an increased conductivity of the electrode/gel relative to the skin/tissue resulted in current concentration at the electrode edges and associated pain/discomfort problems. Modeling studies supporting this including for DC stimulation. However, we have found that, unexpectedly, gels with increased conductivities (for example, increased Cl− conductivity) often resulted in less discomfort.

In a preferred embodiment, added salts include NaCl added as a salt and/or present in a saline base. More than one salt may be used. NaCl supplements may be used including addition of 0.1 to 50 grams of NaCl per 100 grams of base. In a particularly preferred embodiment the electrolyte concentration is 0.01 to 15% by weight in water, and preferably between 0.25 to 4%, and more preferably 0.5 to 2.5%. In the most preferred embodiment, the gel contains NaCl at a concentration of around 2% by weight.

In addition to the core concepts mentioned above, the gel may include various additive agents such as perfumes, colorants, and preservatives. Suitable materials are those conventional in the art. Specialized additional agents which act to protect or restore the skin include potassium bitartrate, coconut oil, sulfated castor oil, Aloe Vera, aloe barbadensis leaf juice, glycerin, synthetic beeswax, cetearyl alcohol, calcium acetate, and vitamins E, A, & D. Local anesthetics may be added to the gel include Lidocaine, Benzocaine, or derivatives thereof. In one embodiment, 6% Benzocaine is incorporated in the gel. In a preferred embodiment, Lanacane, which includes 6% Benzocaine, is diluted in the gel at 1-50% by weight, or more preferred around 2-10%. In another preferred embodiment, 2.5% Lidocaine and/or 2.5% Prilocaine are incorporated in the gel. In another embodiment, Lidocaine/Prilocaine 2.5/2.5% Cream as sold by Fougera is incorporated in the gel at 1-50% by weight. In another embodiment, A mantle as sold by Doak Dematologics is incorporated in the gel at 1-50% by weight.

We have determined key properties, and a specific gel having these properties, that can be used for minimal pain or discomfort during neurocranial stimulation. Therefore, in the most preferred embodiment, the electrode gel of the invention comprises: Polymer, Humectants, Reverse Osmosis water, Surface active agent, Color, Sodium chloride (0.5% Saline Base plus NaCl supplement (CCNY-4). In an alternate preferred embodiment, the gel additionally contains around 2.5% lidocaine or benzocaine as an anesthetic (CCNY-5).

According to a fourth aspect of the invention, there is provided a method to reduce irritation, sensation, discomfort, injury, burns, perception, inflammation, pain, or redness during cranial neurostimulation comprising selecting an appropriate combination of (1) gel and (2) solid conductor which support electrolyte depletion or formation at the cathode or anode.

Accordingly, a fifth aspect of the invention provides specific combinations of (1) gel and (2) solid conductor of the electrode that allow for the reduction or prevention of irritation, sensation, discomfort, injury, burns, perception, inflammation, pain, or redness during cranial neurostimulation.

It is clear from the above discussions of gels, that design of the electrode assembly may require steps beyond simply limiting gel pH or temperature. We have found that a particularly effective strategy is to specifically match the electrode with the gel(s) used for neurocranial stimulation. In the embodiments, the gel/electrode combination used is predicted to support the active electrolyte formation or depletion of the solid conductor based on electrochemical knowledge.

In terms of matching the electrolyte gel to the electrode being used, it is commonly believed that any metal/gel configuration that supports the electrode electrolyte formation or depletion at an electrode will minimize voltage. For a pertinent example of a preferred electrode made of AgCl, it is commonly thought that AgCl formation/depletion will minimize electrode voltage.

However, we have made new discoveries in this regard. We have found that some configurations that supported this reaction "too much" actually worked less to reduce pain than configurations that didn't support the reaction to the same level. For example, using one gel with no Cl− (Lectron II) resulted in reduced potentials (and hence increased run times) compared to other gels with Cl−(Signa), and Lectron II was nominally less supportive of these reactions that need Cl−.

Thus, combined with the findings above on conductance, we have designed gels with an optimized level of electrical conductivity. In a preferred embodiment, the gels have an ideal salt content. In a still more preferred embodiment, the gels were designed with an ideal level of Cl−, discussed below. In the preferred embodiment, the gel electrical conductivity is 0.5 S/m to 10 S/m. In a still preferred embodiment the conductivity is 1 S/m to 6 S/m. In the most preferred embodiment, the electrical conductivity is 4 S/m to 5 S/m. In another embodiment, the gel thermal conductivity is 0.01 W/m.C to 0.05 W/m.C. In the most preferred embodiment the thermal conductivity is 0.025 W/m.C to 0.035 W/m.C.

Further exploration of electrochemical systems intended for use (i.e. the electrodes and gels) informs on specific gel parameters under given electrode systems. In one embodiment, a metal electrolyte MX is converted to M+X− (aq) through the addition of one electron at the "negative" electrode and M is converted to MX by accepting X− (aq) ion and releasing electrons at the "positive electrode". In another embodiment, MX is converted to M++X (aq) through the removal of one electron at the "positive" electrode and M is converted to MX by accepting M+ (aq) ion and accepting electrons at the "negative electrode". In the embodiments, X may be a halide such as chlorine or iodine, and M may be any metal such that MX is any electrical conductive substance and the conversion of M to MX and MX to M is an electrochemically reversible or irreversible reaction. In a preferred embodiment both the positive and negative metal electrodes are AgCl and the ion is Cl. In a particularly preferred embodiment the surface area of AgCl contacting the Cl containing gel is greater than 0.5 $cm^2$ per 40 coulombs of charge transfer. In another particularly preferred embodiment the metal in the positive and negative electrodes is not the same. In one such embodiment, one electrode is Ag and the other is AgCl. The electrode should have a porosity between 0% (fully dense) and 50% with a mean pore size between 1 µm and 100 µm.

In another embodiment, a corrosion resistant metal electrode (such as but not limited to stainless steel alloys, gold, aluminum, nickel, copper) plate or mesh or a conductive carbon pad, weave or mesh acts as a current collector where a neutral salt MX forms M+ and X− when dissolved in water. Upon placing a potential upon the electrodes, $H_2$ gas will evolve at the "negative" electrode and species X will deposit/evolve at the "positive" electrode, where species X may be chlorine or iodine. In one embodiment the metal electrode is platinum. In a particularly preferred embodiment the surface area of Pt contacting containing gel is greater than 0.5 $cm^2$ per 40 coulombs of charge transfer. The electrode should have a porosity between 0% (fully dense) and 50% with a mean pore size between 1 µm and 100 µm.

In some applications, more than one gel or electrolyte layer are used. In one embodiment, charge is transferred such that Xn− is passed through a gel, paste, or hydrated film electrolyte, through the skin and other bodily tissue and re-emerges through the skin to a second gel, paste or hydrated film electrolyte. A counter ion, Mn+, must exist, and may also carry charge. In one preferred embodiment M and X is selected from ions commonly present in biological fluid or tissue.

In a particularly preferred embodiment of the above descriptions of one or more gels, X is Cl and M is Ag. In one preferred embodiment the concentration of X in the gel is selected to approximate the concentration of X present in biological tissue, such as skin, or biological fluid. In one particularly preferred embodiment Ag+Cl− concentration is between 10 mM and 200 mM. In another preferred embodiment, the concentration of X in the gel is selected to exceed the concentration of X normally present in biological tissue. In a still preferred embodiment, the [Ag] and [Cl] concentration in the gel is 200 mM to 2 M. In another preferred embodiment two or more ions commonly found in biological fluid or tissue are present in the gel. In a particularly preferred embodiment, the concentration of ions approximates the concentration of ion normally present in biological fluid or tissue. In a still further preferred embodiment, 5 ions in the gel approximate the concentration of 5 ions in biological tissue or fluid. These ions may correspond to the more dominant or active ions in tissue or more mobile ions. The ions may include: Na, K, Cl, Ca, and Mg. In one preferred embodiment the peak or average current density of X− in the gel is greater than 0.1 mA per $cm^2$ and less than 10 mA per $cm^2$.

In another embodiment, X− is passed through a gel, paste or hydrated film electrolyte, transported to the skin where X− transfers charge through the skin to species Y, where X is deposited or evolved and species Y become Y− through necessary charge balance. Species Y− is then transported through skin and bodily tissue to a second gel, paste or hydrate film electrolyte where species Y is evolved or deposited and species X converters to species X− through necessary charge balance. Species X− is then transported to a second electrode and undergoes an electrochemical reaction as described above. Accordingly, M+ may be passed through a gel, paste or hydrated film electrolyte, transported to the skin where M+ transfers charge through the skin to species N, where M is deposited or evolved and species N becomes N− through necessary charge balance. Species N− is then transported through skin and bodily tissue to a second gel, paste or hydrate film electrolyte where species N is evolved or deposited and species M converters to species M+ through necessary charge balance. Species M+ is then transported to a second electrode and undergoes an electrochemical reaction as described above. In one preferred embodiment X− is selected from ions not normally present in the body at significant concentrations. In a still preferred embodiment X− is chloride ion or iodine ion. In one preferred embodiment the charge transfer density of X and Y is great than 1 coulombs per 0.5 cm2 of gel skin contact area but less than 100 coulombs per 0.5 cm2 of dell skin contact area. In another preferred embodiment, to prevent the above reactions, ions not normally present in significant quantities in biological tissue or fluid are omitted from the gel. In a still preferred embodiment, the activity or ions in the gel that are not present in significant quantities in biological tissue is less than 1 mM. The inclusion or omission of ions normally present in biological tissue is ultimately determined by overall design factors outline above including the reduction of generated voltages, undesired electrochemical products, and irritation. A shown in this invention, the design and selection of gel composition in an appropriate manner is necessary for safe and effective neurocranial stimulation.

In another embodiment the electrolyte medium is a paste consisting of cellulose, any cellulose derivative or modification, or any natural fiber mixed with a brine solution consisting of any concentration of salt MX in water where M is sodium, potassium, magnesium or silver and X is chlorine or iodine where the concentration of salt in the brine is between 10 and 200 mM and the ratio of brine to lotion is such that a minimum viscosity of 100 CPS and a maximum viscosity of 100,000 CPS is maintained while maintaining a conductivity on the order of 10-3 S/cm or greater.

In another embodiment the electrolyte medium is a paste consisting of cellulose, any cellulose derivative or modification, or any natural fiber mixed with a brine solution consisting of any concentration of salt MX in water where M is sodium, potassium, magnesium or silver and X is chlorine or iodine where the concentration of salt in the brine is between 10 and 200 mM and the ratio of brine to lotion is such that a minimum viscosity of 100 CPS and a maximum viscosity of 100,000 CPS is maintained while maintained a conductivity on the order of 10-3 S/cm or greater.

In another embodiment any hydrophilic film or membrane (including but not limited to natural sponge, polyethylene oxide, any fluorinated high molecular weight polymer with a molecular weight exceeding 100,000) hydrated with a brine solution consisting of any concentration of salt MX in water where M is sodium, potassium, magnesium or silver and X is chlorine or iodine where the concentration of salt in the brine is between 10 and 200 mM and the ratio of brine to lotion is such that a minimum viscosity of 100 CPS and a maximum viscosity of 100,000 CPS is maintained while maintained a conductivity on the order of 10-3 S/cm or greater. The film may be set or crosslinked via photons, thermal treatment or chemical treatment such as, but not limited to, deprotonation, oxidation or reduction.

To improve electrochemical performance while maintaining a low level of discomfort, specific additional electrolytes may be used. In one embodiment a supporting electrolyte in the form of ocean or sea water (100 mM to 500 mM solutions) which may be but not limited to NaCl, MgCl2 or KCl in addition to the brine solutions discussed above.

The support material for the electrolyte and electrode is specifically designed for the purposes of the invention. In one embodiment be a non-reactive and non-conductive ceramic such as but not limited to Al2O3 or TiO2 where the holder may or not be porous. If porous the pore size will be between 30 µm and 500 µm. In another embodiment be a non-reactive and non-conductive polymer such as but not limited to PVDF, PVC, Acrylic or ABS where the holder may or not be porous. If porous the pore size will be between 30 µm and 500 µm. In another embodiment be a composite of non-reactive and non-conductive polymers and ceramics, where the polymers may be but are not limited to PVDF, PVC, Acrylic or ABS and the ceramics may be but are not limited to Al2O3 or TiO2 where the holder may or not be porous. If porous the pore size will be between 30 µm and 500 µm Solid conductors suitable for use in the combination include those commonly used in the art for the application or monitoring of current across the skin. Examples of such suitable conductors of the electrode include rubber, Ag, and Ag/AgCl. In a preferred embodiment, the electrode solid conductor is sintered AgCl.

As outlined above, the combination consists of gels and electrolytes that are, when combined, predicted to support the active electrolyte formation or depletion of the solid conductor based on electrochemical knowledge. In a preferred embodiment, the electrodes/gel combination is expected to support the formation and depletion of AgCl at the anode and cathode, respectively. In a particularly preferred embodiment, the combination consists of an Ag or Ag/AgCl solid conductor with CCNY-4 gel.

According to a sixth aspect, there is provided a method to reduce irritation, sensation, discomfort, injury, burns, perception, inflammation, pain, or redness during neurocranial stimulation comprising the steps of:

selecting a suitable electrode-skin contact area;
  selecting a suitable metal electrode material;
  selecting an electrode shape;
  selecting a rigid or semi-rigid holder;
  selecting an appropriate gel;
  selecting a chemical to apply to the gel or the skin;
  selecting a temperature for the gel/skin;
  combining the electrode and gel in the holder, wherein said holder determines the shape and volume of the gel, the position of the electrode relative to the gel, and the portion of skin exposed to the gel;
  preparing the skin;
  attaching the assembly to the head of an individual with suitable attachment means;
  checking the electrode resistance; and/or
  selecting a conditioning electrical waveform to apply to the skin;

In one embodiment according to the invention, the electrode shape is selected from the group consisting of—Pellet, Ring, recessed surface, saw shaped surface, concave surface, convex surface, a horse-shoe shape, a square, a diaphragm, and Disc. In a preferred embodiment, the electrode shape is a ring. In a still preferred embodiment, the ring outer diameter is greater than 3 times the ring thickness. In yet another preferred embodiment, the inner ring diameter is greater than 50% of the outer ring diameter.

In another preferred embodiment, the electrode shape is a pellet. In a more preferred embodiment, the pellet length is greater than 3 times the pellets diameter.

In another embodiment, the gel is selected from the group consisting of modified existing electrode gels, the base existing gel including Signa, Spectra, Tensive, Lectron II and Redux. In a preferred embodiment the gel is either a modified version of Signa containing additional salt, or is CCNY-4. In a particularly preferred embodiment, the gel is CCNY-4.

In another embodiment, the temperature is selected from the range consisting of ~10-45 degrees centigrade. In a preferred embodiment, the temperature is selected from the range of 10 to 37 degrees centigrade.

In another embodiment, the electrical waveform is selected from the group consisting of DC, Interrupted DC, Symmetrical A.C, Asymmetrical A.C, Unbalanced triphasic, ramped, noise. In a preferred embodiment, the current is direct current, applied via the method of transcranial direct current stimulation (tDCS).

In another embodiment, the skin preparation is selected from the group consisting of applying a skin treatment such as a chemical that may be carried is a delivery material such as a gel or cream, or electrically treating the skin, or mechanically altering the skin including through abrasion and scratching, or changing skin temperature.

In another embodiment, the resistance is selected from the group consisting of 100 ohm to 5 mega ohm, or more preferably 200 ohm to 1 mega ohm, or more preferably 300 ohm to 1 mega ohm, or more preferably 200 ohm to 600 ohm, or more preferably 100 ohm to 600 ohm, or more preferably 400 ohm to 600 ohm.

In another embodiment, the shape of the holder is selected from the group consisting of circular, cylindrical, conical, square. In a preferred embodiment, the shape is a cylinder, or a hyperboloid permutation of a cylinder.

According to a seventh aspect, there is provided an apparatus for applying transcranial current through the scalp using a plurality of electrodes, each electrode comprising: at least semi-rigid shell with a distal end contacting the scalp and a proximal end with a portion of the shell encompassing a portion of a gel, at least one electrical stimulation electrode with a proximal end and a distal end, the distal end making contact with a portion of the gel, and gel or paste contacting the scalp and containing no electrolytes or one or more electrolytes, and a cap or mesh positioned on the scalp and connected to the semi-rigid shell.

In an embodiment according to the invention, the apparatus has a semi-rigid shell which is attached to the head by a means provided in the invention, including a banding apparatus, a plate apparatus, a cross apparatus, or a flexible cap or mesh. In another embodiment, said electrode has a cylindrical shape. In yet another embodiment, the electrode has a shape selected from the group consisting of disk or ring shape. In one embodiment, said gel has high-resistivity while in another embodiment the gel has low-resistivity. In one embodiment, said shell has a circular distal end, while in another embodiment said shell has a square distal end. In one embodiment, said electrode is a metal while in another embodiment said electrode is a ceramic. In one embodiment said electrode is silver while in another embodiment, said electrode is silver chloride. In one embodiment, said semi-rigid shell includes a metal component while in another embodiment, said semi-rigid shell includes insulating material obstructing a portion of the distal end. In yet another embodiment, said semi-rigid shell has a distal end with an aperture of least 1 cm2.

In one embodiment according to the invention, said semi-rigid shell has an adjusting and attaching mechanisms for adjusting said semi-rigid shell to an optimal position on the said cap of mesh to suit an individual patient. In another embodiment, said semi-rigid shell has a distal end with an area increased to reduce current density. In another embodiment, the said semi-rigid shell has a distal end with a mesh to reduce current density.

According to an eighth aspect, there is provided an apparatus for applying transcranial current through the scalp using a plurality of electrodes, each electrode comprising:
at least one semi-rigid shell with a distal end contacting the scalp and a proximal end with a portion of the shell encompassing a portion of the secondary gel;
at least one electrical stimulation electrode with a proximal and distal end making contact with a portion of the primary gel containing no electrolytes or one or more electrolytes;
a secondary gel contacting a portion of the primary gel and the scalp; wherein the secondary gel may contain no electrolytes or one or more electrolytes.

In one embodiment according to the invention, said secondary gel has high-resistivity, while in another embodiment said secondary gel has low-resistivity. In one embodiment, said electrical stimulation electrode is in contact with a portion of the secondary gel, while in another embodiment where said electrical stimulation electrode is not in contact with a portion of the secondary gel. In one embodiment, said semi-rigid shell include separate compartments for the primary gel and the secondary gel, while in another embodiment, said semirigid shell include includes a single compartment for the primary gel and the secondary gel.

According to a ninth aspect, there is provided an apparatus for applying transcranial current through the scalp using a plurality of units, each unit comprising:
at least one semi-rigid shell with a distal end contacting the scalp and proximal end;
a electrode mount with one portion contacting the semi-rigid shell and one portion contact the electrical stimulation electrode;
at least one electrical stimulation electrode with a proximal and distal end making contact with a portion of the gel;
and a gel or paste contacting the scalp and containing no electrolytes or one ore more electrolytes.

In one embodiment, said semi-rigid shell encases a portion of said electrode mount while in another embodiment said electrode mount encases entire semi-rigid shell. In one embodiment, said electrode mount is in contact with said gel or paste; while in another embodiment said semi-rigid shell is in contact with said gel or paste. In one embodiment, said semi-electrode mount is circular or tubular. In one embodiment, semi-electrode mount makes contact with said gel or paste on its inner surface while in another embodiment said semi-electrode mount makes contact with said gel or paste on its outer surface. In one embodiment, said matrix is a hydrophobic polymer containing water in the amount of about 10% to 70% of the matrix. In another embodiment, said matrix is substantially free of acid or of a salt of a strong acid. In yet another embodiment, said matrix is substantially free of chloride salt. In one embodiment, said matrix has a high resistivity compared to the scalp; while in another embodiment, said matrix has a low resistivity compared to the scalp. In one embodiment, said matrix contacts the scalp in an area less than 1 cm2.

According to a tenth aspect, there is provided a transcranial stimulation electrode comprising: an electrically conductive backing and an electrically conductive hydrogel matrix coated thereupon, said matrix being adapted to make contact with the skin of the patients and being sufficiently flexible to conform to the contours of the body.

The present invention facilitates non-invasive neurocranial stimulation by reducing or eliminating irritation or discomfort caused during electro-stimulation. There are several mechanisms by which stimulation can lead to irritation or discomfort including but not limited to: 1) heating; 2) electrical stimulation of axons; 3) pH changes; 4) temperature changes; 5) electroporation or electro-permeation; 6) electrolysis. 7) electrophoresis; 8) iontophoresis; 9) electro-osmosis. These mechanisms may be linked or independent. There are other mechanisms that may lead to irritation or discomfort.

We found that there are several methods to reduce discomfort or irritation during NINCS. The methods are: 1) Optimizing gel or solid-conductor properties; 2) Optimizing electrode and electrode holder geometry and physical properties; 3) Chemical pre-treatment; 4) Electrical pre-treatment; and 5) Feed-back monitoring. Each of these methods may be applied independently or in combination with others.

Typical NINCS Setup:

There is provided a device to generate electrical energy which is delivered to electrodes located on the head of a subject via electrically conductive wires. The device may control applied voltage and/or current. The current is in units of amperes (A) and may be on the scale of milli-Amperes (mA). The current travels down the electrical wires to the electrode where it first enters a solid (semi)rigid conductor—for example a silver disk. The current spreads out from the wire into the solid conductor. The current density (in units of A/m2) describes how the current spreads through the solid conductor—this spread is not uniform (i.e. current density is not the same everywhere). The current density in one part of the solid conductor is not the same as the current density in other parts of the solid conductor. Often current tends to concentrates along the edges of the conductor. After reaching up to the conductor, the current (which is spread across the solid conductor) crosses into the conductive gel. There is an interface between the solid conductor and the gel (this interface is elsewhere referred to as the "electrode" but in this document "electrode" refers to the entire head assembly). The current density at this interface is particularly important. Generally it is desired that the current density be as low as possible and as uniform as possible (i.e. no "hot spots")—although it is recognized that this may not always be the case. The current then moves though the gel where it continues to "spread out"; the measure of this spreading is the value of current density in the gel. Again, the current density in the gel is not uniform throughout the gel, as the current density in one part of the gel is different than the current density in another part of the gel. The gel contacts the skin. There is an interface between the gel and the skin. At this interface, it is again important that the current density be as low as possible and not have any "hot spots" where the current density is very high. The current then enters and moves across the skin. There is a specific current density in the skin, which as in the gel, is not necessarily uniform, leading to current density hot spots in the skin. Generally, it is desirable to avoid these current density hotspots in the skin by making the current density in the skin as low and as uniform as possible. The previous text has described the journey that the current makes through the electrode. The specifics on this journey will depend on the shapes of the materials used, the types of materials used, and also the condition of the skin. The important things are how to make the electrode and how to prepare the skin. By controlling these parameters, the current density can be controlled in a manner that decreases or prevents irritation and discomfort. Current density is not the only explanation for that cause irritation and discomfort and it is not the only parameter that needs to be controlled, but it is one parameter that is likely important.

Changing Properties of the Gel, Semi-Rigid Holder, or Solid-Conductor:

The gel is composed of a material with a chemical composition and material properties. The semi-rigid holder is composed of a material with a chemical composition and material properties. The solid-conductor is composed of a material with chemical composition and material properties. These factors may be controlled and selected to reduce skin irritation/discomfort during NINCS.

One can decide and make the materials well before the experiment. In specific cases, it is possible to change the materials or material properties right before NINCS or even during NINCS.

The following material properties of the gel may be changed to reduce irritation or discomfort:

Gel conductivity, specifically between 30,000 to 60,000 or more than 40,000 μmhos/cm. Gel ionic content, specifically NaCl, KCl and CaCl2.

Gel temperature, specifically in the range of 0 and 37 degrees C.

Gel viscosity, specifically in the range of 1,000 to 1,000,0000 or 180,000-260,000 CPS.

Adding the chemicals to the gel like sodium acetate, sodium hydroxide, sodium citrate etc. As described in this invention, the concentration of Cl is important in neurocranial stimulation. Addition of sodium chloride increase chloride as well as sodium concentration. Addition of the above chemicals increases sodium but not chloride concentration.

Gel antioxidant capacity, specifically adding to the gel antioxidants as described in this invention.

Gel analgesic effect, specifically by adding to the gel analgesics such as described in this invention.

The following material properties of the solid conductor may be changed to reduce irritation or discomfort:

Solid-conductor resistance (proximal to distal end) in the range of 1Ω to 1,000 KΩ or 10Ω-1 KΩ.

The solid conductor may be metal, rubber, conductive rubber, Ag/AgCl, Ag, Gold.

In one preferred embodiment the solid-conductor is sintered Ag/AgCl. In another preferred embodiment the solid conductor is conductive rubber. In another preferred embodiment the ratio of the resistivity on the solid conductor and gel is controlled.

Change Electrode Geometry:

The electrode is composed of a metal, a gel, and holder for the solid-conductor and gel. Generally, the holder is an electrical insulator. The holder contacts the scalp or other part the head or neck. The holder generally forms a well or series of wells, in which the gel is inserted, in such a way that the holder defines the shape of the gel. The solid-conductor contacts the gel and generally is held in place by the holder. The holder generally also attached to an electrode cap or band with position the electrode on the head. A couple images show some examples of geometries and preferred embodiments that will reduce irritation or discomfort during NINCS.

Some of these embodiments incorporate a fin design. The fin is part of the holder. The fin design includes one or more planes, the planes are vertical to the surface of the scalp, and serve two inter-related functions: 1) they divide the gel intro compartments; 2) they position the electrode over these compartments in such a manner that a portion of the electrode contacts each of these compartments. The fins may be parallel plains or may be radially symmetrical around the electrode center, or some other pattern. Each fin may be rectangular shaped or may have a different shape.

Some features of these geometries include—One or more ring metal solid-conductors, where the outer diameter ranges from 1 to 1000 mm or 11-12 mm and the inner diameter ranges from 1 to 1000 mm or 6-7 mm. A pellet solid-conductor with diameter ranging from 1 to 1000 mm or 1.5-2.5 mm and depth ranging from 1 to 1000 mm or 2-4 mm. A disk solid-conductor with diameter ranging from 1 to 1000 mms or 11-12 mm.

The holder divides the gel intro compartments, with the number of compartments ranging from 1 to 100, preferably one compartment for a single gel, or between 2 7, or more preferably 2 to 5 for combinations of gels.

The holder divides the gel intro compartments and a different or same gel is applied to each compartment. The holder fixes the distance of the proximal solid-conductor surface to the scalp surface, where the distance ranges from 0.1 to 100 mm or 2-5 mm.

The holder fixes the position of the solid-conductor using a fin design, where the number of fins ranges from 1 to 1000 and from 2 to 7 and from 3 to 5.

The electrode surface is modified with needles, micro-needles, micro-architecture, nano-features, or nanotubes.

In one preferred embodiment, the solid-conductor is a ring, positioned on a 3-fin radially symmetrical electrode holder. In another preferred embodiment, a single holder accommodates two solid-conductors. On another preferred embodiment, the solid-conductor surface area is increased by change the surface shape of the solid conductor including adding indent or extensions including curved extensions.

Chemical Pre-Treatment:

To reduce irritation or discomfort during NINCS, prior to NINC the skin or electrode may be pre-treated by application of a chemical. The chemical may be applied before the treatment for days, hours, or seconds. The chemical may be applied to the skin or to the electrode. The chemical may be applied by a variety of means including brushing, squeezing, injection, or pouring. The chemical may be allowed to permeate the skin or the gel. The chemical may be applied during NINCS. The chemical may be applied after NINCS. The chemical may be dissolved or mixed in a liquid carrier.

In one embodiment, 0.2-2 ml of a pre-conditioning cream is applied below the electrode. In a preferred embodiment, the pre-conditioning cream is applied >5 minutes before the main stimulation phase. In another preferred embodiment, the resistivity of the pre-conditioning cream is selected to be higher than the resistivity of the gel. In this case, the conditioning cream will modify the current spread including increasing the uniformity of current entry. In another preferred embodiment, the resistivity of the pre-conditioning cream is selected to be less than the resistivity of the gel. In this case, the cream will not significantly increase the overall resistance to current flow, thus minimizing the contribution to electrode potential. The cream will form an interface to both the gel and the skin with changes as described below. For these reasons, the appropriate pre-conditioning cream can be matched to the gel used as described in this invention, and based on the design specifications and constraints as described in this invention. For example, in one preferred embodiment, the pre-conditioning cream includes the primary ion carrier in the gel. In another preferred embodiment, the pre-conditioning cream excludes the primary ion carrier in the gel.

The factors will also take into account if the primary ion carrier in the gel has been matched to a primary ion carrier in the tissue or skin.

In another embodiment, the properties of the pretreatment cream are essentially those of the electrode gels described above in this document. Therefore, in the embodiment the pre-treatment creams are the same composition as optimal electrode gels, but are applied to the scalp prior to stimulation.

The chemical may changes the properties of the skin or may changes the properties of the electrode or may change how current moves between different materials and into and through the skin.

Some of the goals of chemical pre-treatment are to alter skin resistance, alter skin resistivity, make the skin more uniform in resistivity, remove resistivity hot spot or cold spots, block skin pores, open skin pores, change the properties of skin pores (including sweat glands and hair follicles), change the properties of blood vessels in the skin including dilation response, change the properties of axons the skin including firing threshold, the properties of muscle cell including firing threshold and mechanical responses. The chemical may be a substance that blocks or opens sweat pores. Chemicals include:

Buffering agents or pH-balancing creams such as Acid Mantle that help restore acid balance of the skin. This cream can be used under the one that produces a basic product, to maintain a balance. Additionally, it may be useful to use different creams or topical solutions under the anode and cathode based on the properties of the creams;

Pain ointments such as Hydrocortisone 1% cream with Zinc Oxide, one of the main ingredients in creams to reduce irritation. A combination of zinc oxide cream (Balmex, Desitin), vaseline, and aluminum acetate (burrow's solution) can also be made to reduce irritation;

Agents such as Aloe Vera that help reduce chronic redness and inflammation;

Burn ointments such as Foille;

Anti-inflammatory agents such as Cellex-C Sunshade SPF 30+;

or anesthetic or analgesic creams or ointments, such as benzocaine, lidocaine, prilocaine, or lanacane.

The chemical may be a pH buffer such as —$NaH_2PO_4$.

The chemical may be penetration enhancer to reduce the skin impedance like stearic acid, propylene glycol, linoleic acid, ethanol, sodium lauryl sulfate, oleic acid, stearic acid.

The chemical may be activated or transported by electricity either during NINCS or during electrical pretreatment. The chemical may have high conductivity ranging from 1 to 1,000,000 or preferably greater than 40,000, or most preferably 40,000-60,000 μmhos/cm or. The chemical may be an anesthetic such as topical solution. The chemical may reduce pain or irritation such as Tronolane. The chemical may be a muscle relaxant such as Relaxaid.

The chemical may induce temperature changes such as BenGay.

In one preferred embodiment, the chemical is applied to the surface of the skin and then the electrode is positioned over that surface.

In another preferred embodiment, the chemical is applied to the electrode on the surface which will contact the skin, and the electrode is then positioned on the skin.

Electrical Pre-Treatment:

To reduce irritation or discomfort during NINCS, electrical current may be applied prior to the actual stimulation protocol, effectively sensitizing the subject. In the simplest embodiment, the current is applied through the same electrode that is subsequently used for stimulation. However, separate electrodes may be used for electrical pre-treatment.

Electrical pre-treatment may be applied before the treatment for days, hours, or seconds. Additionally, electrical pretreatment may be applied during or after NINCS.

The electrical pre-treatment step works by selecting an appropriate waveform for pre-treatment. The pre-treatment electrical waveform may or may not be same as NINCS. Using a pre-treatment waveform different than that of NINCS may be beneficial in the following ways: 1) the pre-treatment waveform does not itself cause any skin irritation or discomfort but changes skin or electrode conditions such that subsequent NINCS does not induced irritation or discomfort; 2) the pre-treatment waveform does not change brain function but rather changes skin properties.

The electrical pre-treatment waveform used may be DC in the amplitude range of 0.1 to 1 mA and applied for 0.1 to 60 minutes. The electrical pre-treatment waveform may be AC in the amplitude range of 0.1 to 1 mA the frequency range of 0.01 to 500 kHz and applied for 0.1 to 60 minutes The electrical pre-treatment waveform may pulsed with frequency range 0.01 to 500 kHz, and pulse width of 0.1 us to 100 seconds, and an inter-pulse interval 0.1 us to 100 seconds.

The electrical pre-treatment waveform may be noise or noisy including white noise, Gaussian noise, 1/f noise, thermal noise, short noise.

The electrical pre-treatment waveform may be a ramp with a slope of 1 mA per minute to 1 mA per ms. The electrical pre-treatment waveform may be Gaussian with standard deviation of value 0 to 10 or 0 to 10000

The electrical pre-treatment waveform may a combination of the above and may involve repetitive pre-stimulation. The electrical pre-treatment waveform may involve getting subject feed-back.

In one preferred embodiment a low level of conditioning DC current is applied prior to stimulation. The conditioning DC current is below 0.5 mA and may be below 0.1 mA. The conditioning DC current is applied for 1 minute to 30 minutes. The conditioning DC current may be ramped up and down slowly including at a rate of 0.1 mA per minute. After this conditioning DC the NINCS therapy current is applied (which may also be DC current but will generally be of higher and more brain effective amplitudes—in this case the conditioning current may be the same polarity or of opposite polarity to the DC electrical therapy current). The interval between the DC conditioning current and the NINCS electrical therapy current can vary between 0 and 10 minutes. In the interval between the conditioning DC current and the NINCS electrical therapy current, the resistance of the electrode may be tested—this resistance reading may inform if another additional conditioning current in necessary prior to NINCS electrical therapy stimulation (see also feed-back monitoring below).

In one preferred embodiment the electrical pre-treatment waveform increased monotonically. In another preferred embodiment, the intensity of the pre-treatment waveform increases and then decreases prior to the main stimulation phase. In a still preferred embodiment the intensity of the pre-treatment electrical waveform returns to zero. In a still preferred embodiment, the waveform is sinusoidal. In one such embodiment, the sinusoidal waveform has a zero average intensity. In another such embodiment, the sinusoidal waveform has a non-zero average intensity where that average intensity may be positive or negative and may be matched to the intensity and polarity of the main electrical treatment stage. In another preferred embodiment the waveform is a sinusoidal with modulated amplitude. In one such embodiment, the sinusoidal frequency is greater that 1000 Hz. In another such embodiment, the sinusoidal frequency is greater than 10000 Hz. In another preferred embodiment the waveform is composed of two or more sign waves. In one such embodiment, the difference in frequencies between the two waveforms is greater than 100 Hz. In another such embodiment, the difference in frequencies between the two waveforms is less than 100 Hz. In another preferred embodiment, the electrical pre-treatment waveform incorporates pulses.

Feed-Back Monitoring:

To prevent or reduce skin irritation or discomfort, the conditions of the electrode and/or skin may be monitored before, during, or after stimulation. The conditions are monitored by sensing a parameter. These readings may be used to turn off NINCS or adjust NINCS properties including all the properties described above.

The device or sensor which monitors a condition or parameter may be integrated into the NINCS device itself, or may be a separate device, or may have some overlapping components.

The parameter monitored may be displayed to the subject/operator for example using a digital display, or indicator lights, or an audio monitor. The parameter may be stored for later retrieval for example of a storage device. The parameter or combination or parameters may be processed using an algorithm or mathematical function. This algorithm or mathematical function could incorporate addition, subtraction, averaging, averaging over time, filter, low-pass filtering, high-pass filtering, liner or non-linear operations, user defined operations. The output of this algorithm and the parameter form a reading that may be used to change NINCS parameters.

For each reading there may be a 'threshold' value which is used to determine if NINCS should begin, stop, be interrupted, be changed, or if a warning should be provided to the subject or operators.

In one preferred embodiment the electrode voltage and electrode current are monitored and stimulation is stopped if either voltage or current exceed a threshold, if the rate of voltage change or current change exceed a threshold, if the current*voltage exceed a threshold, or if the rate of change of the current*voltage exceeds a threshold. The stimulation may stop instantaneously or may be gradually reduced. A warning may be provided to the subject or operator. The stimulation may stop automatically or after the subject or operator activates a manual switch or trigger.

In another preferred embodiment the electrode voltage and electrode current are monitored and stimulation is decreased if either voltage or current exceed a threshold, if the rate of voltage change or current change exceed a threshold, if the current*voltage exceed a threshold, or if the rate of change of the current*voltage exceeds a threshold. The stimulation current and/or voltage are automatically reduced to be maintained below the threshold. A warning may be provided to the subject or operator. The subject or operator may choose to override the otherwise automatic reduction by activation of a manual switch or trigger.

In another preferred embodiment, the resistance of the electrode is monitored. The resistance may be monitored by application of a test voltage or current pulse. The test voltage or current pulse may be sufficiently small such that no brain modulation or skin irritation results. The test voltage or current pulse may be DC or AC. The resistance may act as a threshold for feed-back to determine is NINCS may begin or may continue. The resistance of the electrode may be passed through a mathematical function to determine the resistance quality. The resistance of an electrode may be compared again another value such as the resistance of another electrode.

In another preferred embodiment, the impedance of the electrode is monitored. The impedance may be monitored by application of series of test voltages or current pulses. The series of test voltages or current pulses may be sufficiently small such that not brain modulation or skin irritation results. The series of test voltages or current pulses may be DC or AC of different frequencies. The impedance may act as a threshold for feed-back to determine is NINCS may begin or may continue. The impedance of the electrode may be passed through a mathematical function to determine the impedance quality. The impedance of an electrode may be compared again another value such as the resistance of another electrode.

In another preferred embodiment, a temperature probe is inserted into the gel or portion of the electrode and monitors temperature. The temperature probe may be a thermocouple or a thermistor or optical.

In another preferred embodiment, a pH probe is inserted into the gel or portion of the electrode and monitors pH. The pH probe may be an electrochemical or solid-state or optical. The electrode voltage with a threshold for change ranging from 1 to 1000 V, and 50 to 150 V. The electrode voltage change over time ranging from 0.001 V per hour to 1000 V per second. The electrode current, with a threshold for change ranging from 0.1 to 1000 mA, and 1 mA to 20 mA.

EXAMPLES

Methods
Electrode Configurations: Materials and Geometry

Five types of solid-conductors were tested in the study: 1) "Ag pellet" (2117—Silver Wire; Surepure Chemetals, Florham Park, N.J., USA); 2) "Ag/AgCl sintered pellet" (550015-pellet electrode; A-M systems Inc, Carlsborg, Wash., USA); 3) "Rubber pellet" (116A-GSR-5, rubber electrode; Austin Medical equipment, Westchester, Tex., USA; all pellets were 2 mm(D)×4 mm(L) resulting in ~30±2.5 mm$^2$ solid-conductor-gel contact area); 4) "Ag/AgCl sintered ring" (EL-TP-RNG Sintered; Stens Biofeedback Inc, San Rafael, Calif.; with outer and inner periphery diameter as 12 mm and 6 mm respectively, resulting in a ~140±5 mm$^2$ solid-conductor-gel contact area); and 5) "Ag/AgCl sintered disc" (550025, Disc Electrode A-M Systems; with 8 mm diameter resulting in ~85±5 mm$^2$ electrode-gel contact area). Each electrode-gel configuration was independently evaluated as an anode or cathode. Plastic holders for all electrodes were used to position electrodes over the skin and standardize gel volume used. Plastic holders for all pellet electrodes held ~90±5 mm$^3$ of gel volume with a gel-skin contact area of ~25±2.5 mm$^2$. Customized holders for ring/disc electrodes contained ~280±10 mm$^3$ of gel and provided ~95±5 mm$^2$ gel-skin contact area.

The following gels were tested: 1) "Signa Gel" (Parker Laboratories Inc., Fairfield, N.J., USA), 2) "Spectra 360" (Parker Laboratories Inc.), 3) "Tensive" (Parker Laboratories Inc.), 4) "Redux" (Parker Laboratories Inc.), 5) "1090 BioGel" (UFI Inc., Morro Bay, Calif., USA), 6) "Lectron II" (Pharmaceutical Innovations Inc., Newark, N.J., USA), and 7) "CCNY-4" (custom made). All gels were at room temperature at the time of application. The electrical conductivity values of the gels, measured by a portable digital conductivity meter (Model 2052; VWR International LLC, Bridgeport, N.J., USA), were (in units of μmhos/cm): CCNY4~(45,000±10,000), Signa~(40,000±10,000), Redux~(35,000±10,000), Lectron II~(15,000±7,500), 1090 BioGel~(15,000±7,500), Tensive~(6,000±3,000), and Spectra~(1,500±500). The thermal conductivity values of the gels, measured by a thermal properties meter (Model KD2; Decagon, Pullman Wash., USA), were (in units of W/m° C.): CCNY4~(0.0326±0.0043), Signa~(0.0285±0.0034), Redux~(0.0326±0.0043), Lectron II~(0.0285±0.0008), 1090 BioGel~(0.0280±0.0008), Tensive~(0.0295±0.0024), and Spectra~(0.0274±0.0007).

DC Stimulation and Resistance

A constant current stimulator (CX 6650, Schneider Electronics, Gleichen, Germany) was used to apply direct current for all trials, with a maximum driving voltage capability of 66.7 Volts. A current intensity of 2 mA was used for up to 22 minutes, with automatic on and off ramps of 10 sec to avoid "stimulation break" effects. The stimulator automatically terminates stimulation at an output potential (total potential across both electrodes and agar/tissue) of 66.7 V; which was used as a cut-off point in all trials. Prior to and after stimulation, total cell resistance (see below) of the agar gel or forearm skin was measured using a RMS digital multimeter (FLUKE 177; FLUKE Corporation, Everett, Wash., USA); stimulation was only initiated when the total cell resistance was less than 8 MΩ.

Electrode Potential, pH, and Temperature Studies

For studies measuring electrode potential, pH, and temperature changes, the electrodes were mounted with gel on a flat block of agar made with 150 mM (physiological) NaCl. For these studies, the rationale was to measure changes at only one "active" anode or cathode electrode without contribution from the two return electrodes. The two return electrodes, generally sintered Ag/AgCl disc or ring electrodes, were each immersed in an excess of ~400±10 mm3 Signa Gel. The total cell resistance reflected the resistance between the active electrode and the two return electrodes which are connected in parallel. In this report, "electrode potential" generally refers to the total potential over the entire assembly of electrodes, gel, and skin.

In all experiments, 2 mA of DC current was applied for up to 22 minutes, between one active anode or cathode electrode and the two return electrodes. For experiments quantifying electrode potential, current was passed between the active and return electrodes, and voltage was simultaneously measured. The reference electrode was an 8 mm sintered Ag/AgCl disc electrode immersed in Signa Gel of volume in excess of ~400±10 mm3. Therefore, the total measured voltage is a summation of voltage drops across the active electrode (including electrode, active electrode-gel interface, active electrode gel), agar gel (from the active to reference electrode), and reference electrode (across which current is not passed): it is expected that the only voltage that will change substantially as a result of stimulation is the voltage across the active electrode. Thus the measured voltages in these experiments largely reflect the electrode-gel interface "over-potential" at the active electrode.

A calibrated micro pH electrode (Orion 9810BN; Thermo Scientific, Waltham, Mass., USA) and a digital pH meter (SM100; Milwaukee Instruments Inc., Rocky Mount, N.C., U.S.A.) were used to measure pH in the active electrode's gel at the agar surface, at various exposure durations. To measure the pH, the stimulation was turned off, the solid conductor was removed from the gel, and the micro pH electrode was inserted into the gel within 5 seconds. pH was recorded after exposure durations of 1 min, 5 min, 10 min, 15 min and 20 min. pH studies were conducted on four solid-conductors (Ag pellet, Ag/AgCl sintered pellet, Rubber pellet, Ag/AgCl sintered ring) in combination with three electrolyte gels (Signa Gel, Lectron II Gel, CCNY4 Gel). For temperature experiments, a Type T Thermocouple Thermometer (BAT-10; Physitemp Instruments, Clifton, N.J., USA) was used on the bottom surface of the gel during stimulation.

As indicated above, the stimulator automatically stopped stimulation if a total potential of 66.7 V (cut-off voltage) was achieved. In cases when stimulation was applied for 22 minutes, the "stimulation time" was scored as 22 minutes and the maximum pH and temperature changes during the 22 minutes were noted. In cases when a potential of 66.7 V was reached prior to 22 minutes, the "stimulation time" was scored as the time when the potential reached 66.7V; the maximum pH and temperature at this "stimulation time" was then noted Subjective Sensation: Eight healthy subjects (6 males and 2 females; 19-35 years) participated in each experiment. All gave written informed consent before being included in the study. The study was approved by the IRB board of the City College of New York. Sensation tests were restricted to four solid-conductors (Ag pellet, Ag/AgCl sintered pellet, Rubber pellet, Ag/AgCl sintered ring) and three gels (Signa, Lectron II, and CCNY4). The experiments were conducted on the distal or proximal forearm, as arbitrarily preferred by the subjects. For sensation studies, the rationale was to determine the effect of the "active" electrode (either cathode or anode). Two Ag/AgCl ring electrodes were used as "return" electrodes. Return electrodes were positioned on opposite sides of the active electrode. Each return electrode was immersed in ~280±10 mm$^3$ volume of Signa Gel. Regions of skin with visible irritation or cuts prior to stimulation were avoided. There were no steps taken to otherwise prepare the skin prior to stimulation.

Stimulation was applied for up to 22 minutes with subjects scoring pain (on a 1 to 10 analog scale) every minute beginning two minutes before, every minute during, and ending two minutes after stimulation. In addition, subjects were prompted to describe the sensations ("burning", "prickling" etc.). Prior to stimulation each subject indicated a personal termination value (at or below 5) at which stimulation would be stopped by the operator. In addition, each subject could request to stop the stimulation at any point of the experiment, regardless of the current pain score or nature of perception. If stimulation was stopped prior to 22 minutes of exposure, the pain score at termination was noted. Greater than 1 hour of delay was allowed between experiments, and the stimulation site (e.g. arm) was changed for consecutive experiments. Participants were blinded to the type and combination of solid-conductor and gels tested. After stimulation any skin lesions or redness was noted.

Results Electrode Potential

Electrode potential across conductive agar was recorded during 2 mA DC stimulation. During clinical stimulation it is desirable to minimize electrode potential for several reasons including: 1) voltage limits on constant current stimulators; 2) increased risk for skin injury including through electrochemical reactions (limited by electrode over-potential) and heating. Cathodal stimulation with rubber pellets resulted in variable voltage increases whereas electrode potential remained less than 1V for all other solid-conductors. Anodal stimulation with all solid-conductors resulted in increased and variable electrode potential values.

Electrode potential results for anodal stimulation experiments are summarized; we report both the average potential and variability across trials (5 trials per electrode/gel combination). These potentials can also be interpreted as reflecting changes in the resistance at the electrode site during DC anodal stimulation. When the stimulator potential reached 66.7 V (driving voltage capacity of CX 6650), stimulation was automatically stopped and this was recorded as the maximum exposure duration ("stimulation time") for that trial; otherwise the exposure duration was scored as 22 minutes.

FIGS. 29 and 30 illustrate the electrode potential results for trials employing electrode assemblies having pellet type electrodes.

FIG. 29 illustrates a current-induced polarization of a AG pellet type electrode assembly shown as apparent voltage across anode over time. 2 mA DC current with indicated gels was passed, and the change in voltage with time was measured. Back dotted curves shows five repeats while solid lines shows average. The electrode assembly shown is used only to indicate the general design.

FIG. 30 illustrates a current-induced polarization of a Ag—AgCl pellet type electrode assembly shown as apparent voltage across an anode electrode assembly over time. 2 mA DC current with indicated gels was passed, and the change in voltage with time was measured. Back dotted curves shows five repeats while solid lines shows average. The electrode assembly shown is used only to indicate the general design.

FIG. 31 illustrates the electrode potential results for trials employing electrode assemblies having a rubber type electrodes. A current-induced polarization of a rubber pellet type electrode assembly is shown as apparent voltage across an anode electrode assembly over time. 2 mA DC current with the indicated gels was passed, and the change in voltage with time was measured. Back dotted curves shows five repeats while solid lines shows average. The electrode assembly shown is used only to indicate the general design FIG. 32 illustrates the electrode potential results for trials employing an electrode assembly having a disc type electrode. Current induced polarization of an Ag—AgCl disk type electrode assembly is shown as apparent voltage across anode over time. A 2 mA DC current with indicated gels was passed and the change in voltage with time was measured. Back dotted curves shows five repeats while solid lines show an average. The electrode assembly shown is used only to indicate the general design.

FIG. 33 illustrates the electrode potential results for trials employing an electrode assembly having a ring type electrode. Current induced polarization of an Ag—AgCl ring type electrode assembly is shown as apparent voltage across an anode electrode assembly over time. 2 mA DC current with the indicated gels was passed, and the change in voltage with time was measured. Back dotted curves show five repeats while solid lines show averages. The electrode assembly shown is used only to indicate the general design.

Figure 36:
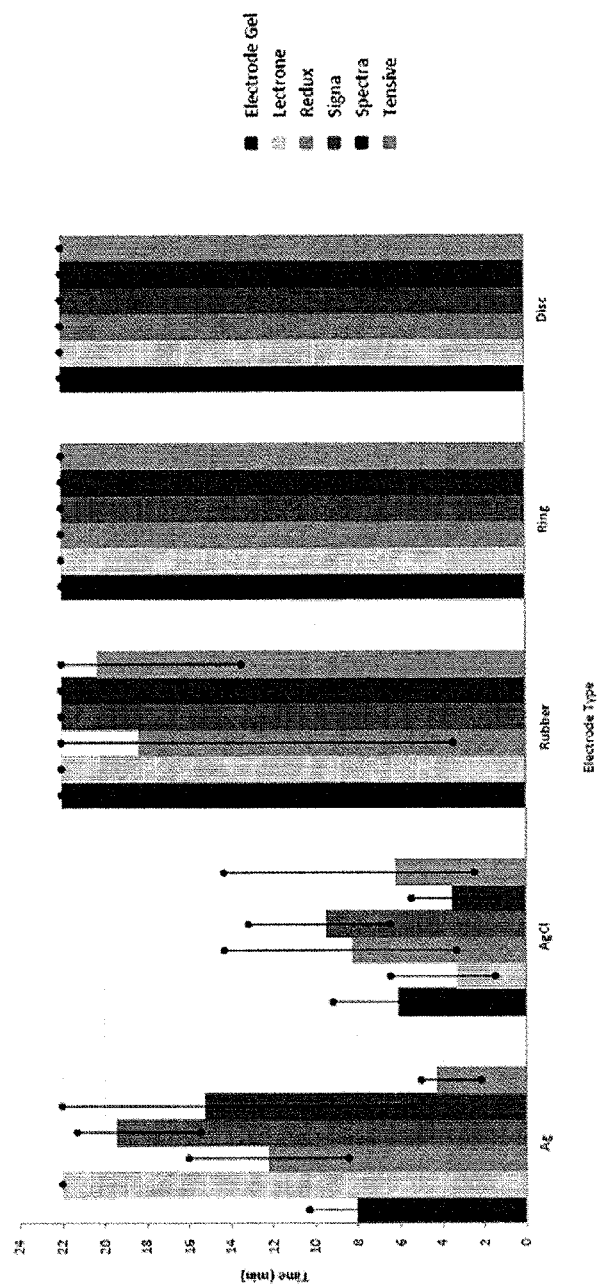
FIG. 36 presents bar graphs showing average run time of different electrodes with different electrolyte gels according to the present invention.

FIG. 36 presents a summary of run times by electrode type according to the trials of FIGS. 31-33 Average potential run time profiles during anodal stimulation for designed electrode assemblies. 22 minutes represents the maximum time tested. For each electrode, the run times are indicated for seven gels from left to right: Electro Gel, Lectron, Redux, Signa, Spectra, Tensive, CCNY4.

FIG. 37 presents a summary of pain and electrochemical performance of designed Neurocranial electrode assemblies. 2 mA of current was used in all cases. A summary of average pain scores (high, and average over stimulation period) across subjects is provided, together with a percentage of subjects electing to stop stimulation prior to 22 minutes, a percentage of subjects with redness under electrodes following stimulation, and indications of peak changes in temperature and in pH of the gel.

Using the Ag/AgCl sintered pellets, the full 22 minutes of anodic stimulation could not be applied in combination with any gel. Using the Ag pellet, 22 minutes of anodic stimulation could be consistently applied only with Lectron II gel and after stimulations a removable, black paste-like residue was observed along the surface of the electrode. Using the Rubber pellet, some variability in exposure time was observed across various trials and gels; in addition, a relatively wide deposition layer was observed on the rubber after stimulation. This layer was easily deterged and an apparently intact and unaffected rubber solid-conductor surface remained. Using both Ag/AgCl sintered ring and Ag/AgCl disk electrodes, 22 minutes of stimulation could be consistently applied, in combination with any gel, with Ag/AgCl disk having the lowest average electrode potentials.

Gel pH and Temperature

For pH and temperature measurements we investigated three gels: two with chloride (Signa and CCNY-4) and one nominally chloride free (Lectron II); each gel was independently tested in combination with four solid-conductors (Ag pellet, Ag/AgCl sintered pellet, Rubber pellet, Ag/AgCl sintered ring). All measurements were conducted on agar gel (150 mM of NaCl). Both Anodal and Cathodal stimulations were tested independently. In the cases where the total cell potential (including electrode potential) exceeded the stimulator cut-off (66.7 V), measurements were limited to the maximum exposure time allowed prior to cut-off.

Cathodal stimulation, which results in minimal electrode potential values did not induce significant temperature increases in the gel under any condition tested. For anodal stimulation, in cases where no electrode potential change occurred (e.g. Ag/AgCl sintered ring with any gel) no temperature changes were observed in the gel. Across all three tested gels, temperature rises were observed under anodal stimulation with both Ag pellet and Ag/AgCl sintered pellet solid conductors, where electrode potential changes were also maximal. During stimulation with Rubber pellet, there was significant trial-to-trial variability in the temperature changes induced; however, as voltage increase was observed, temperature increased monotonically (though not linearly) with voltage and time. Temperature changes in gel under electrode may thus be avoided by limiting changes in electrode potential. For a fixed electrode configuration (pellet), a change in potential was qualitatively related with a change in temperature.

No pH changes were found across all tested electrodes, for either polarity, while using Lectron II gel. In the case of Ag/AgCl sintered pellet and Ag/AgCl ring, no pH changes were observed, under either cathodal or anodal stimulation, for all three gels. Using Ag pellet, no pH changes were observed during anodal stimulation, while pH alkalization was observed with Signa and CCNY-4 gel during cathodal stimulation. Rubber pellets only with Signa and CCNY-4 gel, resulted in acidic gel pH with anodal stimulation and basic gel pH in cathodal stimulation even in the absence of a voltage change. Thus, while increase in temperature is linked to increased electrode potential, pH changes is not directly linked to electrode potential, and are material specific; pH changes can be avoided using appropriate solid-conductor and gel combinations.

Subjective Sensation

Figure 34:
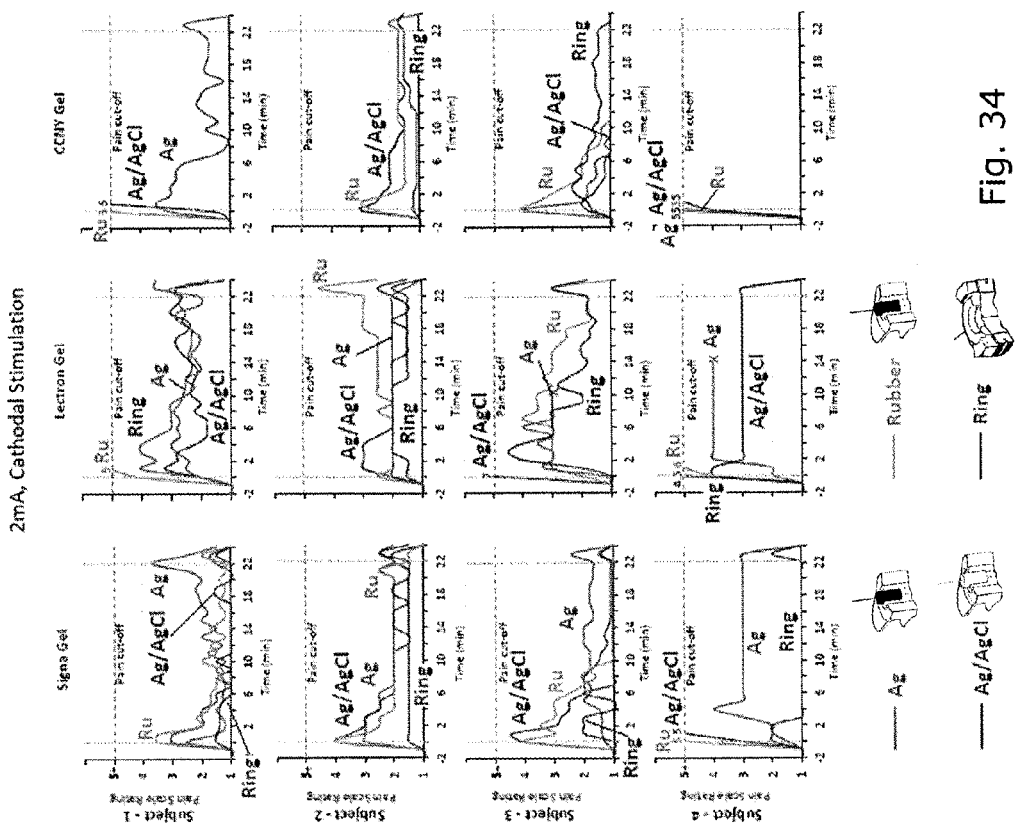
FIG. 34 illustrates pain developed during cathodal stimulation in various subjects when stimulation is applied using variety of gels and variety of electrodes according to the present invention.
Figure 35:
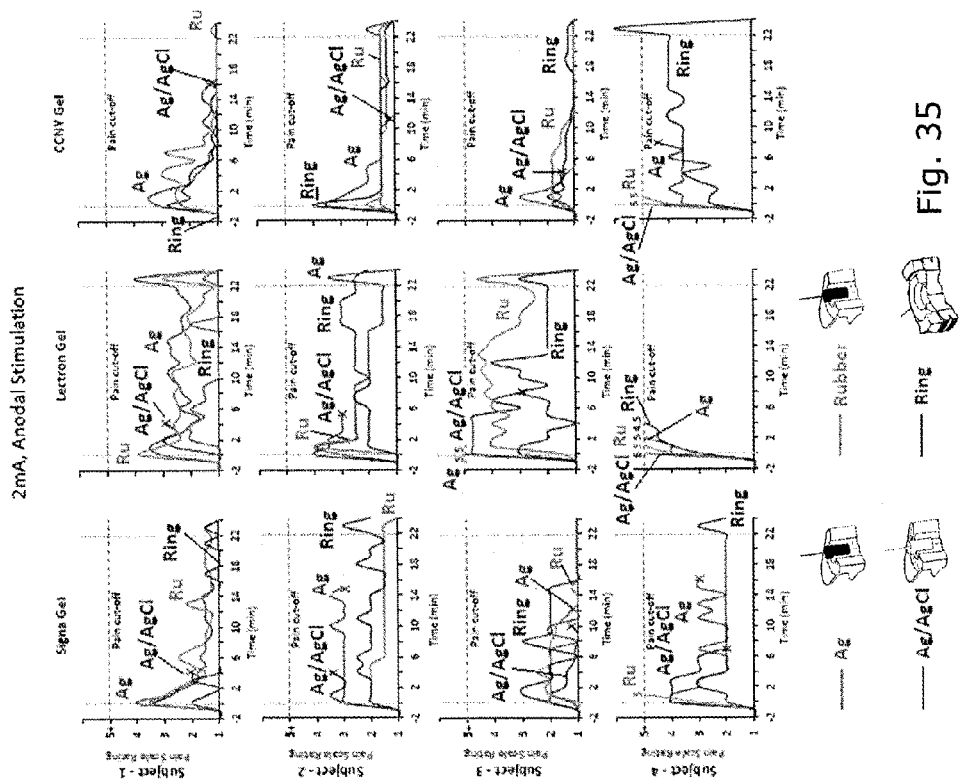
FIG. 35 illustrates pain developed during anodal stimulation in various subjects when stimulation is applied using variety of gels and variety of electrodes according to the present invention.

FIG. 34 illustrates subjective pain results for trials employing cathodal stimulation. Subjective sensation scores of four subjects during 22 minutes of cathodal stimulation (t=0 to 22), for each electrode assembly FIG. 35 illustrates subjective pain results for trials employing anodal stimulation. Subjective sensation scores of four subjects during 22 minutes of anodal stimulation (t=0 to 22), for each electrode assembly N-way (gel, polarity and electrode) ANOVA was applied to the pain ratings. ANOVA revealed a significant effect of gel ($F(1,8)=10.37$, $p=0.0001$) and electrode ($F(1,8)=3.38$, $p=0.019$) on pain ratings. There was no effect of polarity ($F(1,8)=0.05$, $p=0.831$) or interaction effects of gel-polarity ($F(1,8)=0.72$, $p=0.488$), gel-electrode ($F(1,8)=0.33$, $p=0.922$), polarity-electrode ($F(1,8)=0.13$, $p=0.944$) and gel-electrode-polarity ($F(1,8)=0.37$, $p=0.897$). Overall, Signa gel and CCNY-4 were better tolerated than Lectron II. There was no significant difference between anodal verses cathodal stimulation.

Across subjects, stimulation polarity, electrode gel, and configurations, subjective sensation was highest when stimulation was ramped on or off. As expected for any relative individual pain scoring, there were differences in absolute levels between subjects as well as differences in conditions tolerated. A majority of subjects indicated that sensation was restricted only to the "active" test electrode (anode or cathode), but in a few cases subjects indicated sensation under the return electrode(s); this was not an exclusion criteria. There was no evident correlation between pH or temperature changes to that of the subject sensation; for example Ag/AgCl sintered ring electrodes resulted in no temperature or pH changes but did induce discomfort in some subjects.

Examination of the skin after stimulation indicated slight redness. Overall, in cathodal stimulations there are higher chances of observing skin irritation in the form of small bumps or black dots (<1 mm) and apparent roughening of the skin under the electrode. Observation of lesions was not apparently correlated to subjective pain sensation or any physical gel changes. All effects on the skin were reversible and disappeared within few hours. No subject reported a lasting irritation of pain.

In comparing between forearm and agar gel stimulations, the total cell potentials recorded were not significantly different. Therefore results obtained for the forearm and agar gel with respect to total cell potential are comparable. We observed no consistent relationship between the changes in electrode potential and skin sensation during stimulation (or redness post-stimulation). The average resistance of the tissue prior to stimulation with Ag/AgCl ring electrode ranged from 100 k$\Omega$ to 8 M$\Omega$, with an average value of 675.95±1100 k$\Omega$. After the stimulation, the tissue resistance significantly reduced to a range of 3 k$\Omega$ to 800 k$\Omega$, with an average value of 68.62±272.3 k$\Omega$. Therefore, the average percentage drop of resistance post-stimulation was 92.56%±67%.

Electrochemistry of Surface DC Stimulation

We propose the following electrochemical scheme: when electrode/gel conditions exist to support AgCl depletion/formation at the cathode/anode, electrical stimulation can proceed with minimal over-potential and no pH or temperature change. When during the course of stimulation AgCl depletion/formation is no longer supported, electrode over-potential increases which leads to additional chemical reactions, which, in turn, may ultimately lead to heating and pH changes. Over-potentials do not necessarily lead to (or are sufficient for) such changes, but are necessary for additional chemical reactions.

For DC stimulation, a common approach is to use Ag/AgCl non-polarizing electrode. With Ag/AgCl electrodes, as long as faradaic charge-transfer reactions at the electrode interface can proceed, no significant electrochemical processes initiate. At the cathode, dissolution of silver chloride and reduction of the silver ions facilitates faradaic charge delivery across the electrode.

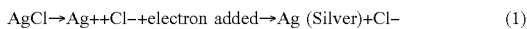

$$AgCl \rightarrow Ag^{++}Cl^{-}+\text{electron added} \rightarrow Ag \text{ (Silver)}+Cl^{-} \quad (1)$$

At the cathode, AgCl is thus depleted from the electrode surface. Under our tested conditions using all Ag/AgCl electrodes (both pellet and ring), the availability of AgCl was apparently sufficient to allow this cathodic reaction for 22 minutes at 2 mA and hence minimal over-potential was generated; this proceeded independent of gel composition (e.g. the baseline concentration of Cl– in the gel being irrelevant, as it is a product). For similar reason, no pH or temperature changes were observed during cathodal stimulation with any AgCl electrodes, independent of gel composition. At the anode electrode site AgCl is formed

$$Ag+Cl^{-} \rightarrow AgCl+e^{-} \quad (2)$$

In contrast to the above described cathodal process; this anodal process requires Cl– availability in the gel and Ag at the solid-conductor surface. One might then predict that anodal stimulation with Ag pellet and Cl– rich gel would produce the least over-potential and longest run times because reaction (2) is supported. However, results show that high over potentials developed during anodal stimulation with Ag pellet and 22 minute run times were achieved only with nominally Cl– free (Lectron II) gels. Our hypothesis in this special case is that due to the rate of reaction (2) there is a rapid formation of AgCl on the metal electrode, which may appear as a black layer on the electrode. This layer may "chemically insulate" the electrode from further reactions, which in turn may explain the increase in the electrode over-potential and decrease in run time. This hypothesis is supported by our observation that after removing this layer, running a second stimulation supports run times comparable to the novel case of the Ag pellet electrode. However, running a second stimulation without removing the AgCl layer, results in run times of less than a minute. The failure of Ag/AgCl pellets to support anodic stimulation may indicate 1) the formation of a similar chemical insulation layer; or 2) insufficient reservoir of available Ag.

Ag/AgCl pellets do not completely support this reaction and hence over-potentials develop. We used micro-temperature and pH sensors to detected physical/chemical changes in the gels under the electrodes during stimulation. We cannot rule out that in during stimulation across skin, hot-spots of temperature or pH changes may occur, for example in sweat glands, which could not be measured in the present study. At the gel, we observed pH changes only with pellet electrodes and specific combination of metal conductor/gel. pH changes reflect for electrochemical reactions at the solid-conductor/gel interface and the ability of the gel to buffer pH changes. When pH changes were observed, the anode site became more acidic and the cathode site more basic; this observation is consistent with oxidation of water at the anode site (formation of H+) and reduction of water at the cathode site (formation of OH–; reviewed in Merrill et al., 2005);

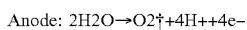

$$\text{Anode: } 2H_2O \rightarrow O_2\uparrow+4H^{+}+4e^{-} \quad (3)$$

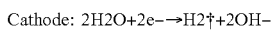

$$\text{Cathode: } 2H_2O+2e^{-} \rightarrow H_2\uparrow+2OH^{-} \quad (4)$$

Acidification at the anode and alkalization at the cathode, are consistent with our observations using un-optimized configurations, and previous pH measurements using various types of electrodes. In all cases where the electrode/gel combination was expected to support AgCl formation or depletion, pH changes were not observed. This is consistent with the reduction/oxidation of water requiring higher electrode over-potential to initiate AgCl formation/depletion. In cases where the respective AgCl reaction was not supported, changes in pH were not necessarily observed, reinforcing the importance of the specific electrode design. Rubber electrodes cannot support either AgCl deletion at the cathode (1) or AgCl formation at the anode (2). The chemical reactions occurring at the rubber-gel interface are poorly defined, and though they may support prolonged stimulation, there was trial-to-trial variability in induced potential and associated temperature and pH changes.

While the invention has been particularly shown and described herein with reference to preferred embodiments thereof, it will be understood by those skilled in the art as described herein that various changes in form and details may be made to the discloses embodiments without departing from the spirit and scope of the invention. Accordingly, the invention is to be limited only by the scope of the claims and their equivalents.

We claim:

1. An electrode assembly for neuro-cranial stimulation comprising:
    an electrode;
    a conductive gel; and
    an adapter comprising an open-ended tube-shaped body, the body defining:
        a first compartment communicating with an opening disposed in a first end of the body for receiving and positioning the electrode relative to the adapter and a second compartment communicating with an orifice disposed in a second end of the body opposite the first end and in fluid communication with the first compartment for receiving and retaining the conductive gel, whereby the conductive gel contacts the electrode along an electrode-gel interface,
        a positioning surface defining the orifice for positioning the electrode assembly against a skin surface of a user, through which orifice the conductive gel is able to contact the skin surface of the user to define a gel-skin interface, and
        a land surface formed in the tube-shaped body between the first and second compartments, the land surface engaging a bottom surface of the electrode to support the electrode at a defined distance from the positioning surface, whereby the electrode is detachably attached to the adapter, and wherein the positioning surface defines a plane that extends laterally across the orifice and the land surface defines a plane displaced parallel to said positioning surface plane so that a minimum distance between the electrode-gel interface and the positioning surface plane during use is fixed between 0.25 cm and 1.3 cm.

2. The electrode assembly of claim 1, wherein an area of the plane within the orifice is between 25 mm² and 95 mm².

3. The electrode assembly of claim 1, wherein a contact area of the electrode-gel interface is between 30 and 1.40 mm².

4. The electrode assembly of claim 1, wherein a ratio of a contact area of the electrode-gel interface and the plane within the orifice is between 0.3 and 5.6.

5. The electrode assembly of claim 1, wherein an area of the plane within the orifice defines a circle or an oval.

6. The electrode assembly of claim 1, wherein one or more surfaces of the electrode define at least one shape selected from the group consisting of rings, thickened rings, discs, pellets, elongated pellets, recessed surfaces, saw-shaped surfaces, concave surfaces, horse shoe-shaped surfaces, helix-shaped surfaces, squares, rectangles, plates, meshes and diaphragms.

7. The electrode assembly of claim 6, wherein the one or more surfaces of the electrode are provided with surface features that increase a surface area of the electrode.

8. The electrode assembly of claim 1, wherein the electrode comprises at least one material selected from the group consisting of metals, alloyed metals, rubber, conductive rubber, Ag/AgCl, Ag, and Au.

9. The electrode assembly of claim 1, wherein the electrode is a ring electrode comprising sintered AgCl.

10. The electrode assembly of claim 9, wherein the sintered AgCl electrode has a porosity of less than 50% with a mean pore size between 1 μm and 100 μm.

11. The electrode assembly of claim 1, wherein the adapter comprises rigid material.

12. The electrode assembly of claim 11, wherein the adapter comprises a non-conductive plastic material.

13. The electrode assembly of claim 1, further comprising a first sealing member affixed to the positioning surface and extending over the orifice of the adapter, the first sealing member being configured to be peeled off or pierced to enable the conductive gel to contact the skin surface of the user to define the gel-skin interface.

14. The electrode assembly of claim 13, wherein an open end of the second compartment of the adapter that is distally positioned relative to the orifice comprises a second sealing member, and the first sealing member and the second sealing member are configured to confine the conductive gel within the second compartment.

15. The electrode assembly of claim 1, wherein the conductive gel has a volume between 0.5 mL and 5 mL.

16. The electrode assembly of claim 1, wherein the conductive gel has a conductivity between 30,000 to 60,000 μohm/cm.

17. The electrode assembly of claim 1, wherein the conductive gel comprises at least one salt selected from the group consisting of NaCl, KCl and $CaCl_2$.

18. The electrode assembly of claim 17, wherein a total gel Cl concentration is greater than 150 mM.

19. The electrode assembly of claim 18, wherein the total gel Cl concentration is greater than 200 mM.

20. The electrode assembly of claim 1, wherein the conductive gel has a viscosity between 180,000 to 260,000 cPs.

21. The electrode assembly of claim 1, wherein the conductive gel further comprises an additive.

22. The electrode assembly of claim 21, wherein the additive comprises an antioxidant.

23. The electrode assembly of claim 21, wherein the additive comprises an analgesic.

24. The electrode assembly of claim 23, wherein the analgesic is selected from the group consisting of Lidocaine, Benzocaine, and Prilocaine.

25. The electrode assembly of claim 21, wherein the additive comprises a pH buffer.

26. The electrode assembly of claim 21, wherein the additive comprises a penetration enhancer selected from the group consisting of stearic acid, propylene glycol, linoleic acid, ethanol, sodium lauryl sulfate, and oleic acid.

27. The electrode assembly of claim 1, wherein the interior compartment comprises one or more locating tabs for positioning the electrode.

28. The electrode assembly of claim 1, wherein the adapter further comprises a cap member configured for enclosing the electrode in the first compartment.

29. The electrode assembly of claim 28, wherein the electrode is fixedly provided to the cap member.

30. The electrode assembly of claim 1, wherein the adapter is further configured for positioning a plurality of electrodes within the first compartment.

31. The electrode assembly of claim 1, wherein the adapter further comprises an accessory piece for holding at least another electrode, the accessory piece being attached to the adapter and in communication with the first compartment of the adapter whereby the conductive gel further extends to contact the other electrode.

32. The electrode assembly of claim 1, wherein the interior compartment comprises one or more fins in proximity to the orifice that extend within the interior compartment.

33. The electrode assembly of claim 32, wherein the one or more fins are configured to position at least a surface of the electrode.

34. The electrode assembly of claim 1, wherein an outer surface of the adapter includes one or more locating features.

35. An apparatus for neuro-cranial stimulation comprising:
one or more electrode assemblies as claimed in claim 1;
one or more bands configured to be secured to the cranium of a user; and
two or more apertures provided in one or more apertured elements each configured to be secured to the one or more hands,
wherein a positioning of the one or more electrode assemblies on the cranium of the user is adjustable by one or more of a repositioning of at least one of the one or more bands or by a movement of the one or more electrode assemblies to alternate ones of the two or more apertures.

36. The apparatus of claim 35, wherein the one or more electrode assemblies comprise a minimum of four electrode assemblies and a maximum of five electrode assemblies.

37. The apparatus of claim 35, wherein the apparatus is configured to adjustably position the electrode assemblies within 1 cm of any target position on the cranium of the user.

38. The apparatus of claim 35, wherein the positioning surfaces of the two or more electrode assemblies are capable of being securely positioned against the skin surface of the user without an adhesive provided to one or more of the positioning surface or the skin surface of the user.

39. The apparatus of claim 35, wherein the one or more apertured elements comprise two or more semicircular plates hingedly joined to form a single circular, articulatable plate.

40. The apparatus of claim 35, wherein the or more apertured elements comprise one or more apertured bands.

41. The electrode assembly of claim 1, wherein the interior compartment is defined by an interior surface having a substantially hyperbolic shape, the interior surface including the land surface.

42. The electrode assembly of claim 41, wherein the electrode has at least two orthogonal surfaces in contact with the conductive gel, and wherein the adapter comprises extrusions for permitting multiple surface contact between the electrode and the conductive gel.

43. The electrode assembly of claim 1, wherein the first compartment has a different diameter than the second compartment, the land surface being disposed at a junction of the first and second compartments.

* * * * *